United States Patent
Ren et al.

(10) Patent No.: US 9,920,331 B2
(45) Date of Patent: Mar. 20, 2018

(54) MAIZE CYTOPLASMIC MALE STERILITY (CMS) S-TYPE RESTORER GENE RF3

(71) Applicant: Dow AgroSciences LLC, Indianapolis, IN (US)

(72) Inventors: Ruihua Ren, Carmel, IN (US); Bruce A. Nagel, Beaver Dam, WI (US); Liang Ye, Carmel, IN (US); Yanxin Star Gao, Waunakee, WI (US); Ryan Gibson, Carmel, IN (US); Sushmitha Paulraj, Sao Paulo (BR); Tyler Mansfield, Indianapolis, IN (US); Jafar Mammadov, Carmel, IN (US); Siva P. Kumpatla, Carmel, IN (US); Steven A. Thompson, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 256 days.

(21) Appl. No.: 14/586,135

(22) Filed: Dec. 30, 2014

(65) Prior Publication Data

US 2015/0307896 A1   Oct. 29, 2015

Related U.S. Application Data

(60) Provisional application No. 61/922,344, filed on Dec. 31, 2013.

(51) Int. Cl.
*C12N 15/82* (2006.01)
*A01H 1/02* (2006.01)
*C07K 14/415* (2006.01)

(52) U.S. Cl.
CPC .......... *C12N 15/8287* (2013.01); *A01H 1/02* (2013.01); *C07K 14/415* (2013.01); *C12N 15/8289* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,695,188 | A | 9/1987 | Pulkkinen |
| 7,135,629 | B2 | 11/2006 | Maves |
| 2005/0064474 | A1 | 3/2005 | Urnov et al. |
| 2007/0083334 | A1 | 4/2007 | Mintz et al. |
| 2009/0087878 | A9 | 4/2009 | La Rosa et al. |
| 2012/0011614 | A1 | 1/2012 | Cigan et al. |
| 2012/0017338 | A1* | 1/2012 | Wu ............... C07K 14/415 800/300 |
| 2012/0090047 | A1 | 4/2012 | Ren et al. |
| 2012/0246748 | A1 | 9/2012 | Guo et al. |

FOREIGN PATENT DOCUMENTS

| | | |
|---|---|---|
| WO | 2003/080809 | 10/2003 |
| WO | 2005/014791 | 2/2005 |
| WO | 2005/084190 | 9/2005 |

OTHER PUBLICATIONS

Kaul, 1988, Male sterility in higher plants, Springer-Verlag, Berlin.
Beckett, 1971, Classification of male sterile cytoplasm in maize (*Zea mays* L), Crop Science, 11: 724-726.
Laughnan and Gabay, 1978, Nuclear and cytoplasmic mutations to fertility in S male-sterile maize, Maize Breeding and Genetics, p. 427-446.
Kamps and Chase, 1997, RFLP mapping of the maize gametophytic restorer-of-fertility locus (rf3) and aberrant pollen transmission of the nonrestoring rf3 allele, Theor Appl Genet, 95: 525-531.
Tie et al, 2006, Genome-wide analysis of maize cytoplasmic male sterility-S based on QTL mapping, Plant Mol Biol, 24: 71-80.
Zhang and Zheng, 2006, AFLP and PCR-based markers linked to Rf3, a fertility restorer gene for S cytoplasmic male sterility in maize, Mol Gen Genomics, 276: 162-169.
Cui et al, 1996, The Rf2 nuclear restorer gene of male-sterile T-cytoplasm maize, Science, 272: 1334-1336.
Bentolila et al, 2002, A pentatricopeptide repeat-containing gene restore fertility to male sterile plants, PNAS, 99: 10887-10892.
Brown et al, 2003, The radish Rf restorer gene of Ogura cytoplasmic male sterility encodes a protein with multiple pentatricopeptide repeats, Plant Journal, 35: 262-272.
Desloire et al, 2003, Identification of the fertility restorer locus, Rfo, in radish, as a member of the pentatricopeptide-repeat protein family, EMBO, Rep, 4: 588-594.
Koizuka et al, 2003, Genetic characterization of a pentatricopeptide repeat protein gene, orf 687, that restores fertility in the cytoplasmic male sterile Kosena radish, Plant Jour, 34: 407-415.
Klein et al, 2005, Fertility restorer locus Rfi of sorghum (*Sorghum bicolor* L.) encodes a pentatricopeptide repeat protein not present in the collinear region of rice chromosome 12, Theor Appl Genet, 111: 994-1012.
Kazama and Toriyama, 2003, A pentatricopeptide repeat-containing gene that promotes the processing of aberrant atp6 RNA of cytoplasmic male-sterile rice, FEBS Lett, 544: 99-102.

(Continued)

*Primary Examiner* — Paul J Holland
(74) *Attorney, Agent, or Firm* — Marcos P. Rivas; Barnes & Thornburg LLP

(57) ABSTRACT

A newly identified protein that is encoded by a polynucleotide sequence associated with cytoplasmic male sterility restorer activity (Rf3) is described. The cytoplasmic male sterility restorer gene can be inserted through breeding introgression into plant genomes to restore cytoplasmic male sterility in plants. Further applications of the newly identified polynucleotide sequence associated with cytoplasmic male sterility restorer activity include a mutation (rf3) which results in cytoplasmic male sterility. The cytoplasmic male sterility restorer gene can be inserted through breeding introgression into plant genomes to result in cytoplasmic male sterility in plants. Methods for detecting the cytoplasmic male sterility restorer (Rf3) and the cytoplasmic male sterility (rf3) gene sequences are further described.

6 Claims, 10 Drawing Sheets

(56) References Cited

OTHER PUBLICATIONS

Akagi et al, 2004, Position cloning of the rice Rf-1 gene, a restorer of BT-type cytoplasmic male sterility that encodes a mitochondria-targeting PPR protein, Theor Appl Genet, 108: 1449-1457.
Komori et al, 2004, Map-based cloning of a fertility restorer gene, Rf-1 in rice (*Oryza sativa* L.), Plant J, 37: 315-325.
Wang et al, 2006, Cytoplasmic male sterility of rice with Boro II cytoplasm is caused by a cytotoxic peptide and is restored by two related PPR motif genes via distinct modes of mRNA silencing, Plant Cell, 18: 676-687.
Sambrook et al. (ed.), Molecular Cloning: A Laboratory Manual, 2nd ed., vol. 1-3, Cold Spring Harbor Laboratory Press, Cold Spring Harbor, New York, 1989.
Van Ooijen et al, 2006, *JoinMap 4: Software for the calculation of genetic linkage maps in experimental populations*, Kyazma BV, Netherlands: Wageningen.
Czechowski et al, 2005, Genome-Wide Identification and Testing of Superior Reference Genes for transcript Normalization in *Arabidopsis*, Plant Physiol, 139(1): 5-17.
Small and Peeters, 2000, The PPR motif—a TPR-related motif prevalent in plant organellar proteins, Trends Biochem Sci, 25: 46-47.
Poehlman, 1995, *Breeding Field Crops*, 4th Edition, AVI Publication Co, Westport, Ct.
Jensen, 1988, *Plant Breeding Methodology*, Wiley, New York, NY.
Pearson, 1981, Nature and mechanism of cytoplasmic male sterility in plants (a review), Hort Sci, 16: 482-487.
MacKenzie et al, 1988, Mitochondrial DNA rearrangement associated with fertility restoration and cytoplasmic reversion to fertility in cytoplasmic maile sterile *Phaseolus vulgaris* L., PNAS, 85: 2714-2717.
Fujii and Toriyama, 2009, Suppressed expression of Retrograde-Regulated Male Sterility restores pollen fertility in cytoplasmic male sterile rice plants, PNAS, 106: 9513-9518.
Barr and Fishman, 2010, The nuclear component of a cytonuclear hybrid incompatibility in Mimulus maps to a cluster of pentatricopeptide repeat genes, Genetics, 184: 455-465.
Itabashi et al, 2011, The Fertility restorer gene, Rf2, for lead Rice-type cytoplasmic male sterility of rice encodes a mitochondrial glycine-rich protein, The Plant Journal, 65: 359-367.
Hu et al, 2012, The Rice pentatricopeptide repeat protein Rf5 restores fertility in Hong-Lian cytoplasmic male-sterile lines via a complex with the glycine-rich protein GRP162, Plant Cell Advance Online Publication.
Lesk, Ed., 1988, *Computational Molecular Biology*, Oxford University, NY.
Smith, Ed., 1993, *Biocomputing: Informatics and Genome Projects*, Academic, NY.
Griffin and Griffin, Ed.,1994, *Computer Analyis of Sequence Data, Part I*, Humanian, NJ, 1994.
Von Heinje, Ed., 1987, *Sequence Analysis in Molecular Biology*, Academic.
Gribskov and Devereux, Eds., 1991, *Sequence analysis PrimerM*, Stockton Press, NY.
Russell and Barton, 1994, Structural Features can be unconserved in proteins with similar fields, J Mol Biol, 244(3): 332-350.
Higgins and Sharp, 1989, Fast and sensitive multiple sequence alignments on a microcomputer, CABIOS, 5: 151-153.
Higgins et al, 1992, CLUSTAL V: improved software for multiple sequence alignment, CABIOS, 8: 189-191.
Altschul et al, 1990, Basic local alignment search tool, J Mol Biol, 215: 403-410.
Pearson, 1994, Comput Methods Genome Res [Proc Int Symp], Meeting Date: 1992, (editors Sandor Shuahi, Plenum, NY, NY), 111-120.
Ausubel et al, 1997, *Short Protocols in Molecular Biology*, Third Edit, p. 2-40.
Yanisch-Perron et al, 1985, Improved M13 phage cloning vectors and host strains: nucleotide sequences of the M13mpl8 and pUC19 vectors, Gene, 33: 103-119.
Knutzon et al, 1992, Modification of *Brassica* seed oil by antisense expression of a stearoyl-acyl carrier protein desaturase gene, PNAS, 89: 2624.
Van Hartingsveldt et al, 1993, Cloning, characterization and overexpression of the phytase-encoding gene (phyA) of Aspergillus niger, Gene, 127: 87.
Raboy et al, 1990, Maydica, 35: 383.
Shiroza and Kuramitsu, 1988, Sequence analysis of the *Streptococcus mutans* fructosyltransferase gene and flanking regions, J Bacteriol, 170(2): 810-816.
Steinmetz et al, 1985, The DNA sequence of the gene for the sectreted Bacillus subtilis enzyme levansucrase and its genetic control sites, Mol Gen Genet, 200: 220.
Pen et al, 1992, Bio/Technology 10: 292.
Elliott et al, 1993, Isolation and characterization of fruit vacuolar invertase genes from two tomato species and temporal differences in mRNA levels during fruit ripening, Plant Mol. Biol., 21: 515.
Sogaard et al, 1993, Site-directed mutagenesis of histidine-93, aspartic acid-180 . . . raw starch binding site in barley α-amylase 1, J Biol. Chem., 268: 22480-22484.
Fisher et al, 1993, Starch Branching Enzyme II from Maize Endosperm, Plant Physiol, 102: 1045.
Fehr et al, 1987, principles of Cultivar Development, p. 261-286.
Kwoh and Kwoh, 1990, Target amplification systems in nucleic acid-based diagnostic approaches, Am Biotechnology Lab, 8: 14-25.
Walker et al, Isothermal in vitro amplification of DNA by a restriction enzyme/DNA polymerase system, 1992, PNAS, 89: 392-396.
Walker et al, 1992, Strand displacement amplification—an isothermal , in vitro DNA amplification technique, , Nucleic Acid res, 20: 1691-1696.
Kwoh et al, 19889, Transcription-based amplification system and detection of amplified human immunodeficiency virus type 1 with a bead-based sandwich hybridization format, PNAS, 86: 1173-1177. 1989.
Guatelli et al, 1990, Isothermal, invitro amplification of nucleic acids by a multienzyme reaction modeled after retroviral replication, PNAS, 87: 1874-1878.
Lizardi et al, 1988, Exponential amplification of recombinant-RNA hybridisation probes, *Biotechnology 6*, 1197-1202.
Lewis, 1992, PCR's Competitors are Alive and Well and Moving Rapidly Towards Commercialization, Genetic Engineering News, 12(9): 1.
Winge, 2000, Innov Pharma Tech, 18-24.
Hood et al, 1997, Commercial Production of Avidin from Transgenic Maize: Characterization of Transformants, Production, processing, extraction, and purification, Molecular Breeding, 3: 291-206.
Towbin et al, 1979, Electrophoretic transfer of proteins from polyacrylamide gels to nitrocellulose sheets: procedure and some applications, PNAS, 76(9): 4350-4354.
Renart et al, Transfer of proteins from gels to diazobenzylmethyl-paper and detection with antisera: a method for studying antibody specificity and antigen structure, PNAS, 76(7): 3116-3120. 1979.
Van Ooijen, 2009, JW: MapQTL 6, Software for the mapping of quantitative trait loci in experimental populations of diploid species, Kyazma BV, Netherlands: Wageningen.
www.maizegbd.org.
Wang et al., "Molecular identification and mapping of a maize gene (Rf3) in S-type CMS using AFLP, RFLP, and SCAR techniques.—PubMed—NCBI", May 28, 2001, https://www.ncbi.nlm.nih.gov/pubmed/11441660.
Zabala et al., "The Nuclear Gene Rf3 Affects the Expression of the Mitochondrial Chimeric Sequence R Implicated in S-Type Male Sterility in Maize", Genetics, vol. 147, Oct. 1, 1997, pp. 847-860.
Database Nucleotide, "*Zea mays* cultivar S-Mo17(Rf3Rf3) PPR-814a mRNA, complete cds", Oct. 1, 2009.
Extended European Search Report, European Application No. 14876104.2-1410 / 3090048, dated Jun. 28, 2017, 7 pages.

\* cited by examiner

FIG. 2

```
                                        1                                        40
SEQ ID NO:12  MBB56       (1) ATGCCGTCATGTGCCCGCATCTCCTCCGCCGTCTCCACCG
SEQ ID NO:8   LH60        (1) ATGCCGTCATGTGCCCGCATCTCCTCCGCCGTCTCCACCG
SEQ ID NO:4   4XP811      (1) ----------------------------------------
SEQ ID NO:10  7SH382ms    (1) ATGCCGTCATGTGCCCGCATCTCCTCCGCCGTCTCCACCG
                                       41                                        80
SEQ ID NO:12  MBB56      (41) CCGCCGCATCCTCCTCCTCGCCGCCGCCGCATCCTCCTCG
SEQ ID NO:8   LH60       (41) CCGCCGCATCCTCCTCCTCGCCGCCGCCGCATCCTCCTCG
SEQ ID NO:4   4XP811      (1) ----------------------------------------
SEQ ID NO:10  7SH382ms   (41) CCGCCGCATCCTCCTCCTCGCCGCCGCCGCATCCTCCTCG
                                       81                                       120
SEQ ID NO:12  MBB56      (81) CTGCCGCCGCCTCGCCGCCGCCACGGCGCGCGTGCGGGAG
SEQ ID NO:8   LH60       (81) CTGCCGCCGCCTCGCCGCCGCCACGGCGCGCGTGCGGGAG
SEQ ID NO:4   4XP811      (1) ----------------------------------------
SEQ ID NO:10  7SH382ms   (81) CTGCCGCCGCCTCGCCGCCGCCACGGCGCGCGTGCGGGAG
                                      121                                       160
SEQ ID NO:12  MBB56     (121) GGGACGCTCCGCCCTGAGGAAGCACACGACCTGCTCGACG
SEQ ID NO:8   LH60      (121) GGGACGCTCCGCCCTGAGGAAGCACACGACCTGCTCGACG
SEQ ID NO:4   4XP811      (1) ----------------------------------------
SEQ ID NO:10  7SH382ms  (121) GGGACGCTCCGCCCTGAGGAAGCACACGACCTGCTCGACG
                                      161                                       200
SEQ ID NO:12  MBB56     (161) AGTTGCAGCGTCGAGGCACGCCCGTTCTCGAGCGCGATCT
SEQ ID NO:8   LH60      (161) AGTTGCAGCGTCGAGGCACGCCCGTTCTCGAGCGCGATCT
SEQ ID NO:4   4XP811      (1) ----------------------------------------
SEQ ID NO:10  7SH382ms  (161) AGTTGCAGCGTCGAGGCACGCCCGTTCTCGAGCGCGATCT
                                      201                                       240
SEQ ID NO:12  MBB56     (201) GAACGGCTTCCTCGCGGCGATCGCGCGTGCGCCGTCCTCC
SEQ ID NO:8   LH60      (201) GAACGGCTTCCTCGCGGCGTTCGCGCGTGCGCCGTCCTCC
SEQ ID NO:4   4XP811      (1) ----------------------------------------
SEQ ID NO:10  7SH382ms  (201) GAACGGCTTCCTCGCGGCGATCGCGCGTGCGCCGTCCTCC
                                      241                                       280
SEQ ID NO:12  MBB56     (241) GCCGCCTGCAGGAGTGGCCCTGCCCTCGCCGTCGCGCTCT
SEQ ID NO:8   LH60      (241) GCCGCCTGCAGGAGTGGCCCTGCCCTCGCCGTCGCGCTCT
SEQ ID NO:4   4XP811      (1) ----------------------------------------
SEQ ID NO:10  7SH382ms  (241) GCCGCCTGCAGGAGTGGCCCTGCCCTCGCCGTCGCGCTCT
                                      281                                       320
SEQ ID NO:12  MBB56     (281) TCAACCGCGCGGCGTCTCGGGCTCAAGGACCGCGGGTGCT
SEQ ID NO:8   LH60      (281) TCAACCGCGCGGCGTCTCGGGCTCAAGGACCGCGGGTGCT
SEQ ID NO:4   4XP811      (1) ----------------------------------------
SEQ ID NO:10  7SH382ms  (281) TCAACCGCGCGGCGTCTCGGGCTCAAGGACCGCGGGTGCT
                                      321                                       360
SEQ ID NO:12  MBB56     (321) GTCCCCACATCCCACACCTACGCCATCCTCATGGACTGC
SEQ ID NO:8   LH60      (321) GTCCCCACATCCCACACCTACGCCATCCTCATGGACTGC
SEQ ID NO:4   4XP811      (1) -------------------------------ATGGACTGC
SEQ ID NO:10  7SH382ms  (321) GTCCCCACATCCCACACCTACGCCATCCTCATGGACTGC
                                      361                                       400
SEQ ID NO:12  MBB56     (361) TGCACCCGCGCGCACCGCCCAGAGCTAGCGCTGGCGTTCT
SEQ ID NO:8   LH60      (361) TGCACCCGCGCGCACCGCCCAGAGCTAGCGCTGGCGTTCT
SEQ ID NO:4   4XP811     (10) TGCACCCGCGCGCACCGCCCAGAGCTAGCGCTGGCCTTCT
SEQ ID NO:10  7SH382ms  (361) TGCACCCGCGCGCACCGCCCAGAGCTAGCGCTGGCGTTCT
                                      401                                       440
SEQ ID NO:12  MBB56     (401) TCGGCCAGCTCCTCAGGACAGGCTTGCGCGTCGATATCAT
SEQ ID NO:8   LH60      (401) TCGGCCAGCTCCTCAGGACAGGCTTGCGCGTCGATATCAT
SEQ ID NO:4   4XP811     (50) TCGGCCAGCTCCTCAGGACAGGCTTGCGCGTCGATATCAT
SEQ ID NO:10  7SH382ms  (401) TCGGCCAGCTCCTCAGGACAGGCTTGCGCGTCGATATCAT
                                      441                                       480
SEQ ID NO:12  MBB56     (441) CATCGCTAACCACCTTCTCAACGGCTTTTGTGAAGCGAAG
```

FIG. 2 continued

```
         SEQ ID NO:8   LH60    (441) CATCGCTAACCACCTTCTCAAGGGCTTTTGTGAAGCGAAG
SEQ ID NO:4   4XP811         (90) CATCGCTAACCACCTTCTCAAGGGCTTTTGTGAAGCGAAG
SEQ ID NO:10  7SH382ms      (441) CATCGCTAACCACCTTCTCAAGGGCTTTTGTGAAGCGAAG
                                   481                                      520
    SEQ ID NO:12  MBB56     (481) CGGACAGACGAGGCTTTGGACATCCTTCTCCACAGAACGC
    SEQ ID NO:8   LH60      (481) CGGACAGACGAGGCTTTGGACATCCTTCTCCACAGAACGC
SEQ ID NO:4   4XP811        (130) CGGACAGACGAGGCTTTGGACATCCTTCTCCACAGAACGC
SEQ ID NO:10  7SH382ms      (481) CGGACAGACGAGGCTTTGGACATCCTTCTCCACAGAACGC
                                   521                                      560
    SEQ ID NO:12  MBB56     (521) CTGAGTTGGGCTGTGTGCCCGATGTTTCTCGTACAGCAT
    SEQ ID NO:8   LH60      (521) CTGAGTTGGGCTGTGTGCCCGATGTTTCTCGTACAGCAT
SEQ ID NO:4   4XP811        (170) CTGAGTTGGGCTGTGTGCCCGATGTTTCTCGTACAGCAT
SEQ ID NO:10  7SH382ms      (521) CTGAGTTGGGCTGTGTGCCCGATGTTTCTCGTACAGCAT
                                   561                                      600
    SEQ ID NO:12  MBB56     (561) ACTTCTGAAGAGCCTCTGCGACCAAGGAAAGAGTGGCCAG
    SEQ ID NO:8   LH60      (561) ACTTCTGAAGAGCCTCTGCGACCAAGGAAAGAGTGGCCAG
SEQ ID NO:4   4XP811        (210) ACTTCTGAAGAGCCTCTGCGACCAAGGAAAGAGTGGCCAG
SEQ ID NO:10  7SH382ms      (561) ACTTCTGAAGAGCCTCTGTGACCAAGGAAAGAGTGGCCAG
                                   601                                      640
    SEQ ID NO:12  MBB56     (601) GCAGATGATTTGCTACGGATGATGTCTGAAGGGGCAGCTG
    SEQ ID NO:8   LH60      (601) GCAGATGATTTGCTACGGATGATGTCTGAAGGGGCAGCTG
SEQ ID NO:4   4XP811        (250) GCAGATGATTTGCTACGGATGATGGCTGAAGGGGCAGCTG
SEQ ID NO:10  7SH382ms      (601) GCAGATGATTTGTTACGGATGATGGCTGAAGGGGCAGCTG
                                   641                                      680
    SEQ ID NO:12  MBB56     (641) TCTGCTCGCCCGACGTGGTTGCCTACAATACAGTAATCGA
    SEQ ID NO:8   LH60      (641) TCTGCTCGCCCGACGTGGTTGCCTACAATACAGTAATCGA
SEQ ID NO:4   4XP811        (290) TCTGCTCGCCCGACGTGGTTGCCTACAATACAGTAATCGA
SEQ ID NO:10  7SH382ms      (641) TCTGCTCGCCCGACGTGGTTGCCTACACTACAGTAATCGA
                                   681                                      720
    SEQ ID NO:12  MBB56     (681) CGGCTTCTTTAAGGAGGGTGACGTAAATAAAGCATGTGAT
    SEQ ID NO:8   LH60      (681) CGGCTTCTTTAAGGAGGGTGACGTAAATAAAGCATGTGAT
SEQ ID NO:4   4XP811        (330) CGGCTTCTTTAAGGAGGGTGACGTAAATAAAGCATGTGAT
SEQ ID NO:10  7SH382ms      (681) CTGCTTCTTTAAGGAGGGTGACGTAAATAAAGCATGTGAT
                                   721                                      760
    SEQ ID NO:12  MBB56     (721) CTATTCAAAGAAATGGTACAGCGGGGCATTCCACCTGATT
    SEQ ID NO:8   LH60      (721) CTATTCAAAGAAATGGTACAGCGGGGCATTCCACCTGATT
SEQ ID NO:4   4XP811        (370) CTATTCAAAGAAATGGTACAGCGGGGCATTCCACCTGATT
SEQ ID NO:10  7SH382ms      (721) CTATTCAAAGAAATGGTACAGCGGGGCATTCCACCTGATT
                                   761                                      800
    SEQ ID NO:12  MBB56     (761) TTGTGACTTATAGCTCTGTGGTTCATGCCCTGTGTAAGGC
    SEQ ID NO:8   LH60      (761) TTGTGACTTATAGCTCTGTGGTTCATGCCCTGTGTAAGGC
SEQ ID NO:4   4XP811        (410) TTGTGACTTATAGCTCTGTGGTTCATGCCCTGTGTAAGGC
SEQ ID NO:10  7SH382ms      (761) TTGTGACTTATAGCTCTGTGGTTCATGCCCTGTGTAAGGC
                                   801                                      840
    SEQ ID NO:12  MBB56     (801) AAGAGCAATGGACAAGGCAGAGGCTTTCCTTCGACAAATG
    SEQ ID NO:8   LH60      (801) AAGAGCAATGGACAAGGCAGAGGCTTTCCTTCGACAAATG
SEQ ID NO:4   4XP811        (450) AAGAGCAATGGACAAGGCAGAGGCTTTCCTTCGACAAATG
SEQ ID NO:10  7SH382ms      (801) AAGAGCAATGGACAAGGCAGAGGCTTTCCTTCGACAAATG
                                   841                                      880
    SEQ ID NO:12  MBB56     (841) GTCAATAAAGGTGTTCTGCCAAATAACTGGACATATAATA
    SEQ ID NO:8   LH60      (841) GTCAATAAAGGTGTTCTGCCAAATAACTGGACATATAATA
SEQ ID NO:4   4XP811        (490) GTCAATAAAGGTGTTCTGCCAAATAACTGGACATATAATA
SEQ ID NO:10  7SH382ms      (841) GTCAATAAAGGTGTTCTGCCAAATAACTGGACATATAATA
                                   881                                      920
    SEQ ID NO:12  MBB56     (881) ACTTGATATATGGATACTCCTCCACAGGACAGTGGAAGGA
    SEQ ID NO:8   LH60      (881) ACTTGATATATGGATACTCCTCCACAGGACAGTGGAAGGA
SEQ ID NO:4   4XP811        (530) ACTTGATATATGGATACTCCTCCACAGGACAGTGGAAGGA
```

FIG. 2 continued

```
SEQ ID NO:10  7SH382ms   (881)  ACTTGATATATGGATACTCCTCCACAGGACAGTGGAAGGA
                                921                                  960
  SEQ ID NO:12  MBB56    (921)  GGCAGTTAGGGTATTTAAAGAAATGAGAAGACATAGCATC
   SEQ ID NO:8  LH60     (921)  GGCAGTTAGGGTATTTAAAGAAATGAGAAGACATAGCATC
SEQ ID NO:4  4XP811      (570)  GGCAGTTAGGGTATTTAAAGAAATGAGAAGACACAGCATC
SEQ ID NO:10  7SH382ms   (921)  GGCAGTTAGGGTATTTAAAGAAATGAGAACACACAGCATC
                                961                                 1000
  SEQ ID NO:12  MBB56    (961)  TTACCAGATGTTGTTACTTTTAACATGTTGATGGGTTCCC
   SEQ ID NO:8  LH60     (961)  TTACCAGATGTTGTTACTTTTAACATGTTGATGGGTTCCC
SEQ ID NO:4  4XP811      (610)  TTACCAGATGTTGTTACTTTGAACATGTTGATGGGTTCCC
SEQ ID NO:10  7SH382ms   (961)  TTACCAGATGTTGTTACTTTGAACATGTTGATGGGTTCCC
                                1001                                1040
  SEQ ID NO:12  MBB56   (1001)  TTTGCAAGTATGGAAAAATCAAGGAAGCTAGAGATGTTTT
   SEQ ID NO:8  LH60    (1001)  TTTGCAAGTATGGAAAAATCAAGGAAGCTAGAGATGTTTT
SEQ ID NO:4  4XP811      (650)  TTTGCAAGTATGGAAAAATCAAGGAAGCTAGAGATGTTTT
SEQ ID NO:10  7SH382ms  (1001)  TTTGCAAGTATGGAAAAATCAAGGAAGCTAGAGATGTTTT
                                1041                                1080
  SEQ ID NO:12  MBB56   (1041)  TGACACAATGGCAATGAACGGGCCAAAATCCTGATGTTTTC
   SEQ ID NO:8  LH60    (1041)  TGACACAATGGCAATGAAGGGCCAAAATCCTGATGTTTTC
SEQ ID NO:4  4XP811      (690)  TGACACAATGGCAATGAAGGGCCAAAATCCTGATGTTTTC
SEQ ID NO:10  7SH382ms  (1041)  TGACACAATGGCAATGAAGGGCCAAAATCCTAATGTTTTC
                                1081                                1120
  SEQ ID NO:12  MBB56   (1081)  TCGTACAATATTATGCTCAACGGGTACGCTACTAAAGGAT
   SEQ ID NO:8  LH60    (1081)  TCGTACAATATTATGCTCAACGGGTACGCTACTAAAGGAT
SEQ ID NO:4  4XP811      (730)  TCGTACAATATTATGCTCAACGGGTACGCTACTAAAGGAT
SEQ ID NO:10  7SH382ms  (1081)  TCCTACAATATTATGCTCAACGGGTACGCTACTAAAGGAT
                                1121                                1160
  SEQ ID NO:12  MBB56   (1121)  GTCTAGTTGATATGACAGATCTCTTCGATTTGATGCTAGG
   SEQ ID NO:8  LH60    (1121)  GTCTAGTTGATATGACAGATCTCTTCGATTTGATGCTAGG
SEQ ID NO:4  4XP811      (770)  GTCTAGTTGATATGACAGATCTCTTCGATTTGATGCTAGG
SEQ ID NO:10  7SH382ms  (1121)  GTCTAGTTGATATGACAGATCTCTTCGATTTGATGCTAGG
                                1161                                1200
  SEQ ID NO:12  MBB56   (1161)  TGACGGTATTGCACCTGTCATTTGTACTTTTAATGTGCTG
   SEQ ID NO:8  LH60    (1161)  TGACGGTATTGCACCTGTCATTTGTACTTTTAATGTGCTG
SEQ ID NO:4  4XP811      (810)  TGACGGTATTGCACCTGTCATTTGTACTTTTAATGTGCTG
SEQ ID NO:10  7SH382ms  (1161)  TGACGGTATTGCACCTGTCATTTGTACTTTTAATGTGCTG
                                1201                                1240
  SEQ ID NO:12  MBB56   (1201)  ATCAAGGCATATGCAAACTGTGGAATGCTAGATAAGGCTA
   SEQ ID NO:8  LH60    (1201)  ATCAAGGCATATGCAAACTGTGGAATGCTAGATAAGGCTA
SEQ ID NO:4  4XP811      (850)  ATCAAGGCATATGCAAACTGTGGAATGCTAGATAAGGCTA
SEQ ID NO:10  7SH382ms  (1201)  ATCAAGGCATATGCAAACTGTGGAATGCTAGATAAGGCTA
                                1241                                1280
  SEQ ID NO:12  MBB56   (1241)  TGATCATCTTCAATGAAATGAGAGACCATGGAGTGAAACC
   SEQ ID NO:8  LH60    (1241)  TGATCATCTTCAATGAAATGAGAGACCATGGAGTGAAACC
SEQ ID NO:4  4XP811      (890)  TGATCATCTTCAATGAAATGAGAGACCATGGAGTGAAACC
SEQ ID NO:10  7SH382ms  (1241)  TGATCATCTTCAATGAAATGAGAGACCATGGAGTGAAACC
                                1281                                1320
  SEQ ID NO:12  MBB56   (1281)  TTATGTGCAACCTATACGACAGTGATTGCTGCCCTCTGC
   SEQ ID NO:8  LH60    (1281)  TTATGTGTAACCTATACGACAGTGATTGCTGCCCTCTGC
SEQ ID NO:4  4XP811      (930)  TTATGTGGAACCTATACGACAGTGATTGCTGCCCTCTGC
SEQ ID NO:10  7SH382ms  (1281)  TTATGTGGAACCTATACGACAGTGATTGCTGCCCTCTGC
                                1321                                1360
  SEQ ID NO:12  MBB56   (1321)  AGAATCGGTAAGATGGATGATGCTATGGAAAAATTTAATC
   SEQ ID NO:8  LH60    (1321)  AGAATCGGTAAGATGGATGATGCTATGGAAAAATTTAATC
SEQ ID NO:4  4XP811      (970)  AGAATCGGTAAGATGGATGATGCTATGGAAAAATTTAATC
SEQ ID NO:10  7SH382ms  (1321)  AGAATCGGTAAGATGGATGATGCTATGGAAAAATTTAATC
                                1361                                1400
```

FIG. 2 continued

```
 SEQ ID NO:12   MBB56    (1361) AGATGATTGATCAAGGAGTAGCACCTGATAAATATGCATA
  SEQ ID NO:8   LH60     (1361) AGATGATTGATCAAGGAGTAGCACCTGATAAATATGCATA
SEQ ID NO:4    4XP811    (1010) AGATGATTGATCAAGCAGTAGCACCTGATAAATATGCATT
SEQ ID NO:10   7SH382ms  (1361) AGATGATTGATCAAGGAGTAGCACCTGATAAATATGCATT
                                1401                                 1440
 SEQ ID NO:12   MBB56    (1401) CCATTGCCTGATTCAAGGTTTTTGTACTCATGGTAGTTTA
  SEQ ID NO:8   LH60     (1401) CCATTGCCTGATTCAAGGTTTTTGTACTCATGGTAGTTTA
SEQ ID NO:4    4XP811    (1050) CCATTGCCTGATTCAAGGTTTTTGTACTCATGGTAGTTTA
SEQ ID NO:10   7SH382ms  (1401) CCATTGCCTGATTCAAGGTTTTTGTACTCATGGTAGTTTA
                                1441                                 1480
 SEQ ID NO:12   MBB56    (1441) CTGAAAGCCAAGGAATTGATTTCGGAAATAATGAATAATG
  SEQ ID NO:8   LH60     (1441) CTGAAAGCCAAGGAATTGATTTCGGAAATAATGAATAATG
SEQ ID NO:4    4XP811    (1090) CTGAAAGCCAAGGAATTGATTTGGAAATAATGAATAATG
SEQ ID NO:10   7SH382ms  (1441) CTGAAAGCCAAGGAATTGATTTTGGAAATAATGAATAATG
                                1481           *                     1520
 SEQ ID NO:12   MBB56    (1481) GCATGCATCTTGACATTGTTTATTCAGTTCGATAATTAA
  SEQ ID NO:8   LH60     (1481) GCATGCATCTTGACATTGTTTATTCAGTTCGATAATTAA
SEQ ID NO:4    4XP811    (1130) GCATGCGTCTTGATATTGTTTTCTTCAGTTCGATAATTAA
SEQ ID NO:10   7SH382ms  (1481) GCATGCGTCTTGATATTGTTTTCTTCAGTTCGATAATTAA
                                1521                                 1560
 SEQ ID NO:12   MBB56    (1521) CAACCTTTGCAAATTGGGAAGGGTAATGGATGCACAAAAT
  SEQ ID NO:8   LH60     (1521) CAACCTTTGCAAATTGGGAAGGGTAATGGATGCACAAAAT
SEQ ID NO:4    4XP811    (1170) CAACCTTTGCAAACTGGGAAGGGTAATGGAGGCACAAAAT
SEQ ID NO:10   7SH382ms  (1521) CAACCTTTGCAAACTGGGAAGGGTAATGGAGGCACAAAAT
                                1561                                 1600
 SEQ ID NO:12   MBB56    (1561) ATATTGACTTAACTGTAAATGTTGGTCTGCATCCTACTG
  SEQ ID NO:8   LH60     (1561) ATATTGACTTAACTGTAAATGTTGGTCTGCATCCTACTG
SEQ ID NO:4    4XP811    (1210) ATATTGACTTAACTGTAAATGTTGGTCTGCATCCTACTG
SEQ ID NO:10   7SH382ms  (1561) ATATTGACTTAACTGTAAATGTTGGTCTGCATCCTACTG
                                1601                                 1640
 SEQ ID NO:12   MBB56    (1601) CTGTGGTGTATAGTATGCTGATGGATGGGTACTGTCTTGT
  SEQ ID NO:8   LH60     (1601) CTGTGGTGTATAGTATGCTGATGGATGGGTACTGTCTTGT
SEQ ID NO:4    4XP811    (1250) CTGTGGTGTATAGTATGCTTATGGATGGGTACTGTCTTGT
SEQ ID NO:10   7SH382ms  (1601) CTGTGGTGTATAGTATGCTTATGGATGGGTACTGTCTTGT
                                1641                                 1680
 SEQ ID NO:12   MBB56    (1641) TGGCAAGATGGAGAATGCATTAAGAGTATTTGATGCTATG
  SEQ ID NO:8   LH60     (1641) TGGCAAGATGGAGAATGCATTAAGAGTATTTGATGCTATG
SEQ ID NO:4    4XP811    (1290) TGGCAAGATGGAGAAAGCATTAAGAGTATTTGATGCTATG
SEQ ID NO:10   7SH382ms  (1641) TGGCAAGATGGAGAAAGCATTAAGAGTATTTGATGCTATG
                                1681                                 1720
 SEQ ID NO:12   MBB56    (1681) GTGTCAGCTGGCATTGAACCATACGATGTAGTGTATGGTA
  SEQ ID NO:8   LH60     (1681) GTGTCAGCTGGCATTGAACCATACGATGTAGTGTATGGTA
SEQ ID NO:4    4XP811    (1330) GTGTCAGCTGGCATTGAACCTACGTTCTAGTGTATGGTA
SEQ ID NO:10   7SH382ms  (1681) GTGTCAGCTGGCATTGAACCAGACGATGTAGTGTATGGTA
                                1721                                 1760
 SEQ ID NO:12   MBB56    (1721) CACTTGTTAATGGCTATTGTAAAATGGAAGGATTGATGA
  SEQ ID NO:8   LH60     (1721) CACTTGTTAATGGCTATTGTAAAATGGAAGGATTGATGA
SEQ ID NO:4    4XP811    (1370) CACTTGTTAATGGCTATTGTAAAATGGAAGGATTGATGA
SEQ ID NO:10   7SH382ms  (1721) CACTTGTTAATGGCTATTGTAAAATGGAAGGATTGATGA
                                1761                                 1800
 SEQ ID NO:12   MBB56    (1761) AGGATTGAGTCTTTTCAGAGAAATGCTGCAAAAGGGAATA
  SEQ ID NO:8   LH60     (1761) AGGATTGAGTCTTTTCAGAGAAATGCTGCAAAATGGAATA
SEQ ID NO:4    4XP811    (1410) AGGATTGAGTCTTTTCAGAGAAATGCTGCAAAAGGGAATA
SEQ ID NO:10   7SH382ms  (1761) AGGATTGAGTCTTTTCAGAGAAATGCTGCAAAAGGGAATA
                                1801                                 1840
 SEQ ID NO:12   MBB56    (1801) AAGCCTTCAACTATTTTATACAACATCATAATTGATGGGT
  SEQ ID NO:8   LH60     (1801) AAGCCTTCAACTATTTTATACAACATCATAATTGATGGGT
```

FIG. 2 continued

```
SEQ ID NO:4   4XP811    (1450) AAGCCTTCAACTATTTTATACAACATCATAATTGATGGGT
SEQ ID NO:10  7SH382ms  (1801) AAGCCTTCAACTATTTTATACAACATCATAATTGATGGGT
                               1841                                 1880

SEQ ID NO:12  MBB56     (1841) TATTTAG---------------------------------
SEQ ID NO:8   LH60      (1841) TATTGAGGCCGGGAGAACAGTTCCTGCAAAGGTGAAATT
SEQ ID NO:4   4XP811    (1490) TATTCAGGCCGGGAGAACAGTTCCTGCAAAGGTGAAATT
SEQ ID NO:10  7SH382ms  (1841) TATTCAGGCCGGGAGAACAGTTCCTGCAAAGGTGAAATT
                               1881                                 1920

SEQ ID NO:12  MBB56     (1849) ----------------------------------------
SEQ ID NO:8   LH60      (1881) CCATGAAATGACAGAAAGTGGTATCGCTATGTACATATGT
SEQ ID NO:4   4XP811    (1530) CCATGAAATGACAGAAAGTGGTATCGCTATCAACAAATGT
SEQ ID NO:10  7SH382ms  (1881) CCATGAAATGACAGAAAGTGGTATCGCTATGAACAAATGT
                               1921                                 1960

SEQ ID NO:12  MBB56     (1849) ----------------------------------------
SEQ ID NO:8   LH60      (1921) ACATACATCATAGTTCTTCGTGGACTTTTTAAAAATAGAT
SEQ ID NO:4   4XP811    (1570) ACATACAACATAGTTCTTCGTGGATTTTTTAAAAATAGAT
SEQ ID NO:10  7SH382ms  (1921) ACATACAACATAGTTCTTCGTGGACTTTTTAAAAATAGAT
                               1961                                 2000

SEQ ID NO:12  MBB56     (1849) ----------------------------------------
SEQ ID NO:8   LH60      (1961) GCTTTGATGAAGCAATCTTTCTTTTCAAAGAATTACGTGC
SEQ ID NO:4   4XP811    (1610) GCTTTGATGAAGCAATCTTTCTTTTCAAAGAATTACGTGC
SEQ ID NO:10  7SH382ms  (1961) GCTTTGATGAAGCAATCTTTCTTTTCAAAGAATTACGTGC
                               2001                                 2040

SEQ ID NO:12  MBB56     (1849) ----------------------------------------
SEQ ID NO:8   LH60      (2001) AATGAATGTAAAGATCGATATCATAACTCTCAATACCATG
SEQ ID NO:4   4XP811    (1650) AATGAATGTAAAGATCGATATCATAACTCTCAATACCATG
SEQ ID NO:10  7SH382ms  (2001) AATGAATGTAAAGATCGATATCATAACTCTCAATACCATG
                               2041                                 2080

SEQ ID NO:12  MBB56     (1849) ----------------------------------------
SEQ ID NO:8   LH60      (2041) ATAGCTGGAATGTTTCAAACCAGGAGAGTTGAAGAAGCTA
SEQ ID NO:4   4XP811    (1690) ATAGCTGGAATGTTTCAAACCAGGAGAGTTGAAGAAGCTA
SEQ ID NO:10  7SH382ms  (2041) ATAGCTGGAATGTTTCAAACCAGGAGAGTTGAAGAAGCTA
                               2081                                 2120

SEQ ID NO:12  MBB56     (1849) ----------------------------------------
SEQ ID NO:8   LH60      (2081) AGGATCTGTTTGCTTCTATCTCGAGAAGTGGGCTGGTGCC
SEQ ID NO:4   4XP811    (1730) AGGATCTGTTTGCTTCTATCTCGAGAAGTGGGCTGGTGCC
SEQ ID NO:10  7SH382ms  (2081) AGGATCTGTTTGCTTCTATCTCGAGAAGTGGGCTGGTGCC
                               2121                                 2160

SEQ ID NO:12  MBB56     (1849) ----------------------------------------
SEQ ID NO:8   LH60      (2121) TTGTGTTGTGACTTACAGTATAATGATCACAAATCTTATA
SEQ ID NO:4   4XP811    (1770) TTGTGTTGTGACTTACAGTATAATGATCACAAATCTTATA
SEQ ID NO:10  7SH382ms  (2121) TTGTGTTGTGACTTACAGTATAATGATCACAAATCTTATA
                               2161                                 2200

SEQ ID NO:12  MBB56     (1849) ----------------------------------------
SEQ ID NO:8   LH60      (2161) AAAGAAGGATTGGTGGAAGAGGCAGAAGATATGTTTTCAT
SEQ ID NO:4   4XP811    (1810) AAAGAAGGATTGGTGGAAGAGGCAGAAGATATGTTTTCAT
SEQ ID NO:10  7SH382ms  (2161) AAAGAAGGATTGGTGGAAGAGGCAGAAGATATGTTTTCAT
                               2201                                 2240

SEQ ID NO:12  MBB56     (1849) ----------------------------------------
SEQ ID NO:8   LH60      (2201) CCATGCAGAATGCTGGCTGTGAGCCCTATTCTCGATTGTT
SEQ ID NO:4   4XP811    (1850) CCATGCAGAATGCTGGCTGTGAGCCCAATTCTCGATTGCT
SEQ ID NO:10  7SH382ms  (2201) CCATGCAGAATGCTGGCTGTGAGCCCGATTCTCGATTGCT
                               2241                                 2280

SEQ ID NO:12  MBB56     (1849) ----------------------------------------
SEQ ID NO:8   LH60      (2241) GAATCATGTAGTCAGGGAATTACTAAAGAAAAATGAAATA
SEQ ID NO:4   4XP811    (1890) GAATCATGTAGTCAGGGAATTACTAAAGAAAAATGAAATA
SEQ ID NO:10  7SH382ms  (2241) GAATCATGTAGTCAGGGAATTACTAAAGAAAAATGAAATA
```

FIG. 2 continued

```
                                  2281                                2320
SEQ ID NO:12   MBB56    (1849)  ----------------------------------------
  SEQ ID NO:8    LH60   (2281)  GTCAGGGCTGGAGCTTACCTGTCCAAGATTGACGAGAGGA
SEQ ID NO:4    4XP811   (1930)  GTCAGGGCTGGAGCTTACCTGTCCAAGATTGACGAGAGGA
SEQ ID NO:10   7SH382ms (2281)  GTCAGGGCTGGAGCTTACCTGTCCAAGATTGACGAGAGGA
                                  2321                                2360
SEQ ID NO:12   MBB56    (1849)  ----------------------------------------
  SEQ ID NO:8    LH60   (2321)  ATTTCTCACTTGAATATTTAACCACAATGTTGCTGGTCGA
SEQ ID NO:4    4XP811   (1970)  ATTTCTCACTTGAACATTTAACCACAATGTTGCTGGTCGA
SEQ ID NO:10   7SH382ms (2321)  ATTTCTCACTTGAACATTTAACCACAATGTTGCTGGTCGA
                                  2361                                2400
SEQ ID NO:12   MBB56    (1849)  ----------------------------------------
  SEQ ID NO:8    LH60   (2361)  TCTCTTCTCAAGCAAAGGAACTTGTAGGGAACACATAAGA
SEQ ID NO:4    4XP811   (2010)  TCTCTTCTCAAGCAAAGGAACTTGTAGGGAACACATAAGA
SEQ ID NO:10   7SH382ms (2361)  TCTCTTCTCAAGCAAAGGAACTTGTAGGGAACACATAAGA
                                  2401                                2440
SEQ ID NO:12   MBB56    (1849)  ----------------------------------------
  SEQ ID NO:8    LH60   (2401)  TTTCTCCCTGCAAAGTATCATTTTCTTGCAGAGGCCAGTC
SEQ ID NO:4    4XP811   (2050)  TTTCTCCCTGCAAAGTATCATTTTCTTGCAGAGGCCAGTC
SEQ ID NO:10   7SH382ms (2401)  TTTCTCCCTGCAAAGTATCATTTTCTTGCAGAGGCCAGTC
                                  2441
SEQ ID NO:12   MBB56    (1849)  -----
  SEQ ID NO:8    LH60   (2441)  CGTGA
SEQ ID NO:4    4XP811   (2090)  CGTGA
SEQ ID NO:10   7SH382ms (2441)  CGTGA
```

FIG. 3

```
                                         1                                        40
SEQ ID NO:9   7SH382ms    (1)  MPSCARISSAVSTAAASSSSPPPHPPRCRRLAAATARVRE
  SEQ ID NO:3    4XP811   (1)  ----------------------------------------
  SEQ ID NO:11   MBB56    (1)  MPSCARISSAVSTAAASSSSPPPHPPRCRRLAAATARVRE
    SEQ ID NO:7    LH60   (1)  MPSCARISSAVSTAAASSSSPPPHPPRCRRLAAATARVRE
                                         41                                       80
SEQ ID NO:9   7SH382ms   (41)  GTLRPEEAHDLLDELQRRGTPVLERDLNGFLAAIARAPSS
  SEQ ID NO:3    4XP811   (1)  ----------------------------------------
  SEQ ID NO:11   MBB56   (41)  GTLRPEEAHDLLDELQRRGTPVLERDLNGFLAAIARAPSS
    SEQ ID NO:7    LH60  (41)  GTLRPEEAHDLLDELQRRGTPVLERDLNGFLAAFARAPSS
                                         81                                       120
SEQ ID NO:9   7SH382ms   (81)  AACRSGPALAVALFNRAASRAQGPRVLSPTSHTYAILMDC
  SEQ ID NO:3    4XP811   (1)  -------------------------------------MDC
  SEQ ID NO:11   MBB56   (81)  AACRSGPALAVALFNRAASRAQGPRVLSPTSHTYAILMDC
    SEQ ID NO:7    LH60  (81)  AACRSGPALAVALFNRAASRAQGPRVLSPTSHTYAILMDC
                                         121                                      160
SEQ ID NO:9   7SH382ms  (121)  CTRAHRPELALAFFGQLLRTGLRVDIIIANHLLKGFCEAK
  SEQ ID NO:3    4XP811   (4)  CTRAHRPELALAFFGQLLRTGLRVDIIIANHLLKGFCEAK
  SEQ ID NO:11   MBB56  (121)  CTRAHRPELALAFFGQLLRTGLRVDIIIANHLLKGFCEAK
    SEQ ID NO:7    LH60 (121)  CTRAHRPELALAFFGQLLRTGLRVDIIIANHLLKGFCEAK
                                         161                                      200
SEQ ID NO:9   7SH382ms  (161)  RTDEALDILLHRTPELGCVPDVFSYSILLKSLCDQGKSGQ
  SEQ ID NO:3    4XP811  (44)  RTDEALDILLHRTPELGCVPDVFSYSILLKSLCDQGKSGQ
  SEQ ID NO:11   MBB56  (161)  RTDEALDILLHRTPELGCVPDVFSYSILLKSLCDQGKSGQ
    SEQ ID NO:7    LH60 (161)  RTDEALDILLHRTPELGCVPDVFSYSILLKSLCDQGKSGQ
                                         201                                      240
SEQ ID NO:9   7SH382ms  (201)  ADDLLRMMAEGGAVCSPDVVAYTVIDCFFKEGDVNKACD
  SEQ ID NO:3    4XP811  (84)  ADDLLRMMAEGGAVCSPDVVAYNTVIDGFFKEGDVNKACD
  SEQ ID NO:11   MBB56  (201)  ADDLLRMMSEGGAVCSPDVVAYNTVIDGFFKEGDVNKACD
    SEQ ID NO:7    LH60 (201)  ADDLLRMMSEGGAVCSPDVVAYNTVIDGFFKEGDVNKACD
                                         241                                      280
SEQ ID NO:9   7SH382ms  (241)  LFKEMVQRGIPPDFVTYSSVVHALCKARAMDKAEAFLRQM
  SEQ ID NO:3    4XP811 (124)  LFKEMVQRGIPPDFVTYSSVVHALCKARAMDKAEAFLRQM
  SEQ ID NO:11   MBB56  (241)  LFKEMVQRGIPPDFVTYSSVVHALCKARAMDKAEAFLRQM
    SEQ ID NO:7    LH60 (241)  LFKEMVQRGIPPDFVTYSSVVHALCKARAMDKAEAFLRQM
                                         281                                      320
SEQ ID NO:9   7SH382ms  (281)  VNKGVLPNNWTYNNLIYGYSSTGQWKEAVRVFKEMRRHSI
  SEQ ID NO:3    4XP811 (164)  VNKGVLPNNWTYNNLIYGYSSTGQWKEAVRVFKEMRRHSI
  SEQ ID NO:11   MBB56  (281)  VNKGVLPNNWTYNNLIYGYSSTGQWKEAVRVFKEMRRHSI
    SEQ ID NO:7    LH60 (281)  VNKGVLPNNWTYNNLIYGYSSTGQWKEAVRVFKEMRRHSI
                                         321                                      360
SEQ ID NO:9   7SH382ms  (321)  LPDVVTLNMLMGSLCKYGKIKEARDVFDTMAMKGQNEVF
  SEQ ID NO:3    4XP811 (204)  LPDVVTLNMLMGSLCKYGKIKEARDVFDTMAMKGQNDVF
  SEQ ID NO:11   MBB56  (321)  LPDVVTFNMLMGSLCKYGKIKEARDVFDTMAMKGQNDVF
    SEQ ID NO:7    LH60 (321)  LPDVVTFNMLMGSLCKYGKIKEARDVFDTMAMKGQNDVF
                                         361                                      400
SEQ ID NO:9   7SH382ms  (361)  SYNIMLNGYATKGCLVDMTDLFDLMLGDGIAPVICTFNVL
  SEQ ID NO:3    4XP811 (244)  SYNIMLNGYATKGCLVDMTDLFDLMLGDGIAPVICTFNVL
  SEQ ID NO:11   MBB56  (361)  SYNIMLNGYATKGCLVDMTDLFDLMLGDGIAPVICTFNVL
    SEQ ID NO:7    LH60 (361)  SYNIMLNGYATKGCLVDMTDLFDLMLGDGIAPVICTFNVL
                                         401                                      440
SEQ ID NO:9   7SH382ms  (401)  IKAYANCGMLDKAMIIFNEMRDHGVKPYVVTYTTVIAALC
  SEQ ID NO:3    4XP811 (284)  IKAYANCGMLDKAMIIFNEMRDHGVKPYVVTYTTVIAALC
  SEQ ID NO:11   MBB56  (401)  IKAYANCGMLDKAMIIFNEMRDHGVKPYVLTYTTVIAALC
    SEQ ID NO:7    LH60 (401)  IKAYANCGMLDKAMIIFNEMRDHGVKPYVLTYTTVIAALC
                                         441                                      480
SEQ ID NO:9   7SH382ms  (441)  RIGKMDDAMEKFNQMIDQGVAPDKYAFHCLIQGFCTHGSL
```

FIG. 3 continued

```
SEQ ID NO:3    4XP811  (324)  RIGKMDDAMEKFNQMIDQGVAPDKYAFHCLIQGFCTHGSL
SEQ ID NO:11   MBB56   (441)  RIGKMDDAMEKFNQMIDQGVAPDKYAYHCLIQGFCTHGSL
SEQ ID NO:7    LH60    (441)  RIGKMDDAMEKFNQMIDQGVAPDKYAYHCLIQGFCTHGSL
                              481                  *               520
SEQ ID NO:9    7SH382ms(481)  LKAKELILEIMNNGMRLDIVFSSIINNLCKLGRVMEAQN
SEQ ID NO:3    4XP811  (364)  LKAKELILEIMNNGMRLDIVFSSIINNLCKLGRVMEAQN
SEQ ID NO:11   MBB56   (481)  LKAKELISEIMNNGMHLDIVLSSIINNLCKLGRVMDAQN
SEQ ID NO:7    LH60    (481)  LKAKELISEIMNNGMHLDIVLSSIINNLCKLGRVMDAQN
                              521                                  560
SEQ ID NO:9    7SH382ms(521)  IFDLTVNVGLHPTAVVYSMLMDGYCLVGRMEKALRVFDAM
SEQ ID NO:3    4XP811  (404)  IFDLTVNVGLHPTAVVYSMLMDGYCLVGRMEKALRVFDAM
SEQ ID NO:11   MBB56   (521)  IFDLTVNVGLHPTAVVYSMLMDGYCLVGKMENALRVFDAM
SEQ ID NO:7    LH60    (521)  IFDLTVNVGLHPTAVVYSMLMDGYCLVGKMENALRVFDAM
                              561                                  600
SEQ ID NO:9    7SH382ms(561)  VSAGIEPDDVVYGTLVNGYCKIGRIDEGLSLFREMLQKGI
SEQ ID NO:3    4XP811  (444)  VSAGIEPYVVVYGTLVNGYCKIGRIDEGLSLFREMLQKGI
SEQ ID NO:11   MBB56   (561)  VSAGIEPYDVVYGTLVNGYCKIGRIDEGLSLFREMLQKGI
SEQ ID NO:7    LH60    (561)  VSAGIEPYDVVYGTLVNGYCKIGRIDEGLSLFREMLQNGI
                              601                                  640
SEQ ID NO:9    7SH382ms(601)  KPSTILYNIIIDGLFQAGRTVPAKVKFHEMTESGIAMNKC
SEQ ID NO:3    4XP811  (484)  KPSTILYNIIIDGLFQAGRTVPAKVKFHEMTESGIAINKC
SEQ ID NO:11   MBB56   (601)  KPSTILYNIIIDGLF------------------------
SEQ ID NO:7    LH60    (601)  KPSTILYNIIIDGLFEAGRTVPAKVKFHEMTESGIAMYIC
                              641                                  680
SEQ ID NO:9    7SH382ms(641)  TYNIVLRGLFKNRCFDEAIFLFKELRAMNVKIDIITLNTM
SEQ ID NO:3    4XP811  (524)  TYNIVLRGFFKNRCFDEAIFLFKELRAMNVKIDIITLNTM
SEQ ID NO:11   MBB56   (616)  ---------------------------------------
SEQ ID NO:7    LH60    (641)  TYIIVLRGLFKNRCFDEAIFLFKELRAMNVKIDIITLNTM
                              681                                  720
SEQ ID NO:9    7SH382ms(681)  IAGMFQTRRVEEAKDLFASISRSGLVPCVVTYSIMITNLI
SEQ ID NO:3    4XP811  (564)  IAGMFQTRRVEEAKDLFASISRSGLVPCVVTYSIMITNLI
SEQ ID NO:11   MBB56   (616)  ---------------------------------------
SEQ ID NO:7    LH60    (681)  IAGMFQTRRVEEAKDLFASISRSGLVPCVVTYSIMITNLI
                              721                                  760
SEQ ID NO:9    7SH382ms(721)  KEGLVEEAEDMFSSMQNAGCEPDSRLLNHVVRELLKKNEI
SEQ ID NO:3    4XP811  (604)  KEGLVEEAEDMFSSMQNAGCEPNSRLLNHVVRELLKKNEI
SEQ ID NO:11   MBB56   (616)  ---------------------------------------
SEQ ID NO:7    LH60    (721)  KEGLVEEAEDMFSSMQNAGCEPYSRLLNHVVRELLKKNEI
                              761                                  800
SEQ ID NO:9    7SH382ms(761)  VRAGAYLSKIDERNFSLEHLTTMLLVDLFSSKGTCREHIR
SEQ ID NO:3    4XP811  (644)  VRAGAYLSKIDERNFSLEHLTTMLLVDLFSSKGTCREHIR
SEQ ID NO:11   MBB56   (616)  ---------------------------------------
SEQ ID NO:7    LH60    (761)  VRAGAYLSKIDERNFSLEYLTTMLLVDLFSSKGTCREHIR
                              801       814
SEQ ID NO:9    7SH382ms(801)  FLPAKYHFLAEASP
SEQ ID NO:3    4XP811  (684)  FLPAKYHFLAEASP
SEQ ID NO:11   MBB56   (616)  --------------
SEQ ID NO:7    LH60    (801)  FLPAKYHFLAEASP
```

MAIZE CYTOPLASMIC MALE STERILITY (CMS) S-TYPE RESTORER GENE RF3

CROSS-REFERENCE TO RELATED APPLICATIONS

This application claims the benefit under 35 USC § 119(e) of U.S. Provisional Application Ser. No. 61/922,344, filed on Dec. 31, 2013, the entire disclosure of which is incorporated herein by reference

REFERENCE TO SEQUENCE LISTING SUBMITTED ELECTRONICALLY

The official copy of the sequence listing is submitted electronically via EFS-Web as an ASCII formatted sequence listing with a file named "74583_ST25.txt", created on Dec. 30, 2014, and having a size of 42 kilobytes and is filed concurrently with the specification. The sequence listing contained in this ASCII formatted document is part of the specification and is herein incorporated by reference in its entirety.

FIELD OF THE DISCLOSURE

The disclosure relates to the isolation and identification of protein sequences that are encoded by the cytoplasmic male sterility restorer (Rf3) and cytoplasmic male sterile (rf3) gene sequences, and for methods of detecting the cytoplasmic male sterility restorer (Rf3) and cytoplasmic male sterile (rf3) gene sequences in plants. Furthermore, the disclosure relates to the field of plant breeding for introducing the cytoplasmic male sterility restorer (Rf3) and cytoplasmic male sterile (rf3) gene sequences into progeny plants.

BACKGROUND OF THE INVENTION

Cytoplasmic male sterility (CMS) is the maternally inherited inability to produce functional pollen and has been successfully used in commercial production of hybrid seed, thus avoiding the drawbacks of hand or mechanical emasculation. (Kaul, M. L. H. 1988. Male sterility in higher plants. Springer-Verlag, Berlin). More than 40 sources of CMS have been identified and classified into three major groups: CMS-T (Texas), CMS-S (USDA) and CMS-C(Charrua) type cytoplasm. (Beckett, J. B., Crop Sci., 11:724-726, 1971).

The Rf restorer genes, which impart and restore fertility to plants that are cytoplasmic male sterile, have been cloned or mapped at high resolution from several plant species. To date, eleven Rf genes have been cloned or mapped to high resolution. Most cloned restorer genes, except Rf2 and Rf4 in maize and Rf17 and Rf2 in rice, encode different pentatricopeptide repeat (PPR) proteins. The PPR proteins contain two to 27 repeats of 35 amino acids, called PPR motifs (Small, I. D. and Peeters, N., Trends Biochem. Sci., 25:46-47, 2000). Many PPR proteins are targeted to mitochondria where the CMS-associated genes and products are located (Lurin, C. et al., Plant Cell, 16:2089-2103, 2004).

In maize, the genes encoding the restorer of the S type cytoplasm of CMS behave as a gametophytic trait. Maize plants with CMS-S type cytoplasm are restored by the single dominant gene, Rf3, which was mapped to genomic fragments of several centimorgans in length on chromosome 2, via marker sequences. (Kamps and Chase, Theor. Appl. Genet., 95:525-531, 1997; Tie, S., Xia, J., Qiu, F. and Zheng, Y. Plant Mol. Biol., 24:71-80, 2006; Zhang, Z. and Zheng Y. Mol. Gen. Genomics., 276:162-169, 2006). Traditional breeding applications deploy the use of markers that are associated at great distance with the Rf3 and rf3 alleles to restore or to provide cytoplasmic male sterility in maize plants, respectively. (Laughnan, J. R. and Gabay, S. J. 1978. Nuclear and cytoplasmic mutations to fertility in S male-sterile maize. pp. 427-446. In: Maize Breeding and Genetics). Furthermore, heterozygous (Rf3/rf3) CMS-S plants are semi-fertile, shedding approximately 50% abortive collapsed pollen containing the rf3 allele and approximately 50% starch-filled fertile pollen containing the Rf3 allele. The rf3 allele in Rf3/rf3 plants cannot be transferred to progeny through sterile pollen, and generate sterile plants in an F2 generation. (Tie et al., Plant Mol. Biol. Rep., 24: 71-80, 2006). This type of inheritance makes it difficult to collect accurate phenotypic data from an F2 mapping population. As such, traditional methods for using or identifying the dominant and recessive alleles of the Rf3 genes are labor and time-intensive.

Therefore, there exists a need exists for compositions and methods that can be utilized to isolate and identify protein sequences that are encoded by the cytoplasmic male sterility restorer (Rf3) and cytoplasmic male sterile (rf3) gene sequences, and for methods of detecting the cytoplasmic male sterility restorer (Rf3) and cytoplasmic male sterile (rf3) gene sequences in plants.

Accordingly, the present disclosure provides an alternative approach for the isolation and identification of polynucleotide and protein sequences encoded by the Rf3 allele that result in the cytoplasmic male sterility restorer phenotype, and subsequent sequence modifications encoded by the rf3 allele that result in the cytoplasmic male sterile phenotype. The discovery of these sequences can be utilized in cytoplasmic male sterile systems for breeding hybrid plants of a number of crop species. Furthermore, the application of this system can result in cost savings and increased efficiency. For example, deployment of a cytoplasmic male sterile system in corn can be used to eliminate the expensive and laborious task of detasselling corn plants to avoid self pollination.

The foregoing examples of the related art and limitations related therewith are intended to be illustrative and not exclusive. Other limitations of the related art will become apparent to those of skill in the art upon a reading of the specification.

BRIEF SUMMARY OF THE INVENTION

The present disclosure provides, an isolated polypeptide comprising an amino acid sequence of SEQ ID NO:1. In a further embodiment the isolated polypeptide of SEQ ID NO:1 comprises an amino acid sequence which has at least 85% sequence identity to SEQ ID NO:3. In aspects of an embodiment, the isolated polypeptides of SEQ ID NO:1 and SEQ ID NO:3 have cytoplasmic male sterile activity.

In other aspects, the present disclosure relates to an isolated polypeptide comprising an amino acid sequence of SEQ ID NO:5. In a further embodiment, the isolated polypeptide of SEQ ID NO:5 comprises an amino acid sequence which has at least 85% sequence identity to SEQ ID NO:7. In aspects of an embodiment, the isolated polypeptides of SEQ ID NO:5 and SEQ ID NO:7 have cytoplasmic male sterile restorer activity.

In additional aspects, the subject disclosure relates to a method for producing a progeny cytoplasmic male sterile plant. In other aspects, the subject disclosure provides methods for restoring fertility to a progeny of a cytoplasmic male sterile plant. In a subsequent aspect, the subject disclosure relates to a method of detecting a plant comprising a cytoplasmic male sterile restorer trait. Furthermore, other aspects of the subject disclosure relate to a method of detecting an expression level of a cytoplasmic male sterile restorer trait In addition to the exemplary aspects and embodiments described above, further aspects and embodiments will become apparent by study of the following descriptions.

BRIEF DESCRIPTION OF THE FIGURES

FIG. 2 illustrates a polynucleotide sequence alignment of the Rf3 coding sequences. The sequences obtained from the 4XP811 and 7SH382 ms plants correspond with the cytoplasmic male sterile plants that are homozygous recessive (rf3/rf3). The sequences obtained from the LH60 and MBB56 plants correspond with the restored cytoplasmic male fertile plants that are homozygous dominant (Rf3/Rf3). The asterisk above the alignment indicates the base pair modification that results in the recessive rf3 allele and encodes the cytoplasmic male sterile trait. This change from SEQ ID NO:6; 5'-ATTGTTTTATTCAGT-3' to SEQ ID NO:2; 5'-ATTGTTTTCTTCAGT-3' (wherein the underlined base pair, indicates the mutated sequence) results in the loss of restorer function and gain of cytoplasmic male sterility phenotype.

FIG. 3 illustrates a protein sequence alignment of the Rf3 coding sequences. The sequences obtained from the 4XP811 and 7SH382 ms plants correspond with the cytoplasmic male sterile plants that are homozygous recessive (rf3/rf3). The sequences obtained from the LH60 and MBB56 plants correspond with the restored cytoplasmic male fertile plants that are homozygous dominant (Rf3/Rf3). The asterisk above the alignment indicates the amino acid residue modification that results in the recessive rf3 allele and encodes the cytoplasmic male sterile trait. This change from SEQ ID NO:5; IVLFS to SEQ ID NO:1; IVFFSS (wherein the underlined amino acid residue, indicates the mutated sequence) results in the loss of restorer function and gain of cytoplasmic male sterility phenotype.

BRIEF DESCRIPTION OF THE SEQUENCES

Figure 1A:
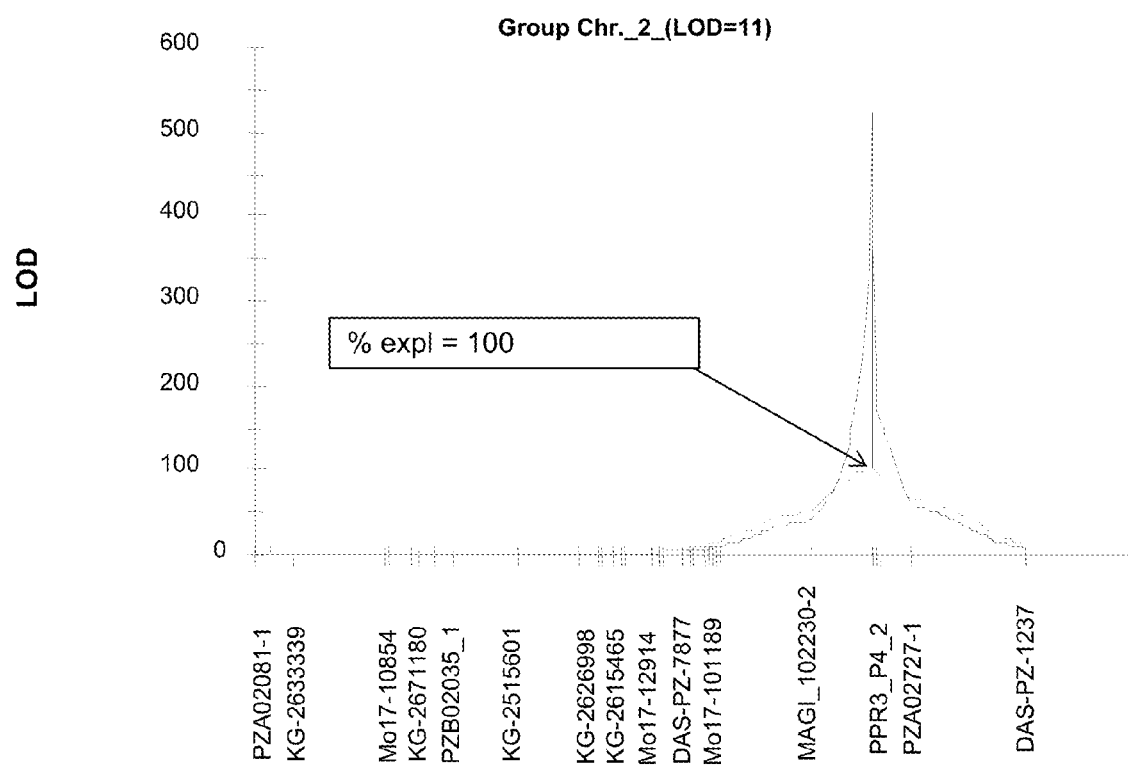
FIG. 1A illustrates the linkage map and QTL position of the Rf3 allele and FIG. 1B illustrates the corresponding trait on chromosome 2.

SEQ ID NO:1 provides the protein motif (IVFFSS) in which Leu is modified to a Phe (underlined), thereby resulting in the loss of restorer function and gain of cytoplasmic male sterility phenotype of the rf3 allele.

SEQ ID NO:2 provides a polynucleotide sequence that encodes for SEQ ID NO:1.

SEQ ID NO:3 provides the protein sequence for the rf3 allele obtained from the cytoplasmic male sterile corn line, Zea mays c.v. 4XP811.

SEQ ID NO:4 provides the cDNA polynucleotide sequence encoding the rf3 allele obtained from the cytoplasmic male sterile corn line, Zea mays c.v. 4XP811.

SEQ ID NO:5 provides the protein motif (IVLFSS) in which conservation of the Leu (underlined) amino acid residue results in a restorer function, male fertile phenotype of the Rf3 allele.

SEQ ID NO:6 provides a polynucleotide sequence that encodes for SEQ ID NO:5.

SEQ ID NO:7 provides the protein sequence for the Rf3 allele obtained from the restored, fertile corn line, Zea mays c.v. LH60.

SEQ ID NO:8 provides the cDNA polynucleotide sequence encoding the Rf3 allele obtained from the restored, fertile corn line, Zea mays c.v. LH60.

SEQ ID NO:9 provides the protein sequence for the rf3 allele obtained from the cytoplasmic male sterile corn line, Zea mays c.v. 7SH382MS.

SEQ ID NO:10 provides the cDNA polynucleotide sequence encoding the rf3 allele obtained from the cytoplasmic male sterile corn line, Zea mays c.v. 7SH382MS.

SEQ ID NO:11 provides the protein sequence for the Rf3 allele obtained from the restored, fertile corn line, Zea mays c.v. MBB56.

SEQ ID NO:12 provides the cDNA polynucleotide sequence encoding the Rf3 allele obtained from the restored, fertile corn line, Zea mays c.v. MBB56.

SEQ ID NO:13 to SEQ ID NO:18 provide primers and probes used for the detection of the dominant and recessive Rf3 alleles.

DETAILED DESCRIPTION

I. Overview

The present disclosure provides, an isolated polypeptide comprising an amino acid sequence of SEQ ID NO:1. In a further embodiment the isolated polypeptide of SEQ ID NO:1 comprises an amino acid sequence which has at least 85% sequence identity to SEQ ID NO:3. In aspects of an embodiment, the isolated polypeptides of SEQ ID NO:1 and SEQ ID NO:3 have cytoplasmic male sterile activity.

In other aspects, the present disclosure relates to an isolated polypeptide comprising an amino acid sequence of SEQ ID NO:5. In a further embodiment, the isolated polypeptide of SEQ ID NO:5 comprises an amino acid sequence which has at least 85% sequence identity to SEQ ID NO:7. In aspects of an embodiment, the isolated polypeptides of SEQ ID NO:5 and SEQ ID NO:7 have cytoplasmic male sterile restorer activity.

In additional aspects, the subject disclosure relates to a method for producing a progeny cytoplasmic male sterile plant. In other aspects, the subject disclosure provides methods for restoring fertility to a progeny of a cytoplasmic male sterile plant. In a subsequent aspect, the subject disclosure relates to a method of detecting a plant comprising a cytoplasmic male sterile restorer trait. Furthermore, other aspects of the subject disclosure relate to a method of detecting an expression level of a cytoplasmic male sterile restorer trait.

II. Clause List

Provided herein are embodiment of the invention, further described by the following enumerated clauses:

1. An isolated polypeptide comprising an amino acid sequence of SEQ ID NO: 1.

2. An isolated polypeptide consisting of an amino acid sequence of SEQ ID NO: 1.

3. An isolated polypeptide consisting essentially of an amino acid sequence of SEQ ID NO: 1.

4. The isolated polypeptide of clause 1 comprising an amino acid sequence which has at least 85% sequence identity to SEQ ID NO: 3.

5. The isolated polypeptide of clause 1 consisting of an amino acid sequence which has at least 85% sequence identity to SEQ ID NO: 3.

6. The isolated polypeptide of clause 1 consisting essentially of an amino acid sequence which has at least 85% sequence identity to SEQ ID NO: 3.

7. The isolated polypeptide sequence of clause 1 or clause 4 wherein the polypeptide has cytoplasmic male sterile activity.

8. A cell comprising the polypeptide of clause 1.

9. The cell of clause 8, wherein the cell is a plant cell.

10. A plant comprising the plant cell of clause 9.

11. The plant of clause 10, wherein the plant is a monocotyledonous plant.

12. The plant of clause 11, wherein the monocotyledonous plant is a maize plant.

13. A seed obtained from the plant of clause 10.

14. A synthetic nucleic acid sequence encoding the polypeptide of clause 1.

15. The synthetic nucleic acid sequence of clause 14 comprising the sequence of SEQ ID NO:2.

16. The synthetic nucleic acid sequence of clause 14 consisting of the sequence of SEQ ID NO:2.

17. The synthetic nucleic acid sequence of clause 14 consisting essentially of the sequence of SEQ ID NO:2.

18. The synthetic nucleic acid sequence of clause 14 comprising at least 90% sequence identity to the sequence of SEQ ID NO:4.

19. The synthetic nucleic acid sequence of clause 14 consisting of the sequence of SEQ ID NO:4.

20. The synthetic nucleic acid sequence of clause 14 consisting essentially of the sequence of SEQ ID NO:4.

21. A polynucleotide comprising the synthetic nucleic acid sequence of clause 14.

22. The polynucleotide of clause 21, wherein the polynucleotide is operably linked to a promoter, wherein the promoter is functional in plants.

23. The polynucleotide of clause 22, wherein the promoter is a plant cytoplasmic male sterile promoter.

24. A cell comprising the polynucleotide of clause 21.

25. A vector comprising the synthetic nucleic acid sequence of clause 14.

26. A cell comprising the vector of clause 25.

27. The isolated polypeptide of clause 1 comprising an amino acid sequence which has at least 85% sequence identity to SEQ ID NO: 9.

28. The isolated polypeptide of clause 1 consisting of an amino acid sequence which has at least 85% sequence identity to SEQ ID NO: 9.

29. The isolated polypeptide of clause 1 consisting essentially of an amino acid sequence which has at least 85% sequence identity to SEQ ID NO: 9.

30. The isolated polypeptide sequence of clause 27, wherein the polypeptide has cytoplasmic male sterile activity.

31. A cell comprising the polypeptide of clause 27.

32. The cell of clause 31, wherein the cell is a plant cell.

33. A plant comprising the plant cell of clause 32.

34. The plant of clause 33, wherein the plant is a monocotyledonous plant.

35. The plant of clause 34, wherein the monocotyledonous plant is a maize plant.

36. A seed obtained from the plant of clause 33.

37. A synthetic nucleic acid sequence encoding the polypeptide of clause 27.

38. The synthetic nucleic acid sequence of clause 37 comprising at least 90% sequence identity to the sequence of SEQ ID NO:10.

39. The synthetic nucleic acid sequence of clause 37 consisting of the sequence of SEQ ID NO:10.

40. The synthetic nucleic acid sequence of clause 37 consisting essentially of the sequence of SEQ ID NO:10.

41. A polynucleotide comprising the synthetic nucleic acid sequence of clause 37.

42. The polynucleotide of clause 41, wherein the polynucleotide is operably linked to a promoter, wherein the promoter is functional in plants.

43. The polynucleotide of clause 42, wherein the promoter is a plant cytoplasmic male sterile promoter.

44. A cell comprising the polynucleotide of clause 41.

45. A vector comprising the synthetic nucleic acid sequence of clause 37.

46. A cell comprising the vector of clause 45.

47. The plant of clause 35, wherein the plant has CMS-S type cytoplasm.

48. A method for producing a progeny cytoplasmic male sterile plant, the method comprising the steps of:
   a) crossing a female parent plant with a male parent plant, wherein the female parent plant is a cytoplasmic male sterile parent plant homozygous for SEQ ID NO:4, and wherein the male parent plant is a fertile parent plant;
   b) harvesting a progeny seed from the cross of step (a), wherein the progeny seed is homozygous for SEQ ID NO:4;
   c) planting the progeny seed; and,
   d) growing the progeny seed, wherein the progeny seed produce the progeny cytoplasmic male sterile plant, wherein the progeny cytoplasmic male sterile plant is homozygous for SEQ ID NO:4.

49. The method for producing a progeny cytoplasmic male sterile plant of clause 48, wherein the female and male parent plants are monocotyledonous plants.

50. The method for producing a progeny cytoplasmic male sterile plant of clause 49, wherein the monocotyledonous plants are maize plants.

51. The method for producing a progeny cytoplasmic male sterile plant of clause 48, wherein the male parent plant is isogenic to the female parent plant.

52. The method for producing a progeny cytoplasmic male sterile plant of clause 48, wherein the male parent plant is homozygous or heterozygous for SEQ ID NO:8.

53. The method for producing a progeny cytoplasmic male sterile plant of clause 48, the method further comprising introducing a desired trait into the progeny cytoplasmic male sterile plant.

54. The method for producing a progeny cytoplasmic male sterile plant of clause 48, the method further comprising the steps of:
   e) crossing the progeny cytoplasmic male sterile plant, with another plant comprising a desired trait to produce F1 progeny plants;
   f) selecting F1 progeny plants that have the desired trait to produce selected F1 progeny plants;
   g) crossing the selected F1 progeny plants with the progeny cytoplasmic male sterile plant to produce backcross progeny plants;
   h) selecting for backcross progeny plants that have the desired trait; and,
   i) repeating steps (g) and (h) three or more times in succession to produce selected fourth or higher backcross progeny plants that comprise the desired trait.

55. The method for producing a progeny cytoplasmic male sterile plant of 53, wherein the desired trait is selected from the group consisting of an insecticidal resistance trait, herbicide tolerant trait, disease resistance trait, yield increase trait, nutritional quality trait, agronomic increase trait, and combinations thereof.

56. A method for producing a progeny cytoplasmic male sterile plant, the method comprising the steps of:
   a) crossing a female parent plant with a male parent plant, wherein the female parent plant is a cytoplasmic male sterile parent plant homozygous for SEQ ID NO:10, and wherein the male parent plant is a fertile parent plant;
   b) harvesting a progeny seed from the cross of step (a), wherein the progeny seed is homozygous for SEQ ID NO:10;
   c) planting the progeny seed; and,
   d) growing the progeny seed, wherein the progeny seed produce the progeny cytoplasmic male sterile plant, wherein the progeny cytoplasmic male sterile plant is homozygous for SEQ ID NO:10.

57. The method for producing a progeny cytoplasmic male sterile plant of clause 56, wherein the female and male parent plants are monocotyledonous plants.

58. The method for producing a progeny cytoplasmic male sterile plant of clause 57, wherein the monocotyledonous plants are maize plants.

59. The method for producing a progeny cytoplasmic male sterile plant of clause 56, wherein the male parent plant is isogenic to the female parent plant.

60. The method for producing a progeny cytoplasmic male sterile plant of clause 56, wherein the male parent plant is homozygous or heterozygous for SEQ ID NO:8.

61. The method for producing a progeny cytoplasmic male sterile plant of clause 56, the method further comprising introducing a desired trait into the progeny cytoplasmic male sterile plant.

62. The method for producing a progeny cytoplasmic male sterile plant of clause 56, the method further comprising the steps of:
   e) crossing the progeny cytoplasmic male sterile plant, with another plant comprising a desired trait to produce F1 progeny plants;
   f) selecting F1 progeny plants that have the desired trait to produce selected F1 progeny plants;
   g) crossing the selected F1 progeny plants with the progeny cytoplasmic male sterile plant to produce backcross progeny plants;
   h) selecting for backcross progeny plants that have the desired trait; and,
   i) repeating steps (g) and (h) three or more times in succession to produce selected fourth or higher backcross progeny plants that comprise the desired trait.

63. The method for producing a progeny cytoplasmic male sterile plant of 61, wherein the desired trait is selected from the group consisting of an insecticidal resistance trait, herbicide tolerant trait, disease resistance trait, yield increase trait, nutritional quality trait, agronomic increase trait, and combinations thereof.

64. A method for restoring fertility to a progeny of a cytoplasmic male sterile parent plant, the method comprising:
   a) crossing a female parent plant with a male parent plant, wherein the female parent plant is a cytoplasmic male sterile parent plant homozygous or heterozygous for SEQ ID NO:8, and wherein the cytoplasmic male sterile plant is a fertile parent plant;
   b) harvesting a progeny seed from the cross of step (a), wherein the progeny seed is homozygous or heterozygous for SEQ ID NO:8;
   c) planting the progeny seed;
   d) growing the progeny seed, wherein the progeny seed produce a progeny cytoplasmic male fertile plant; and,
   e) restoring fertility to the progeny of the cytoplasmic male sterile parent plant, wherein the progeny cytoplasmic male fertile plant is homozygous or heterozygous for SEQ ID NO:8.

65. The method for restoring fertility to a progeny of a cytoplasmic male sterile parent plant of clause 64, wherein the female and male parent plants are monocotyledonous plants.

66. The method for restoring fertility to a progeny of a cytoplasmic male sterile parent plant of clause 65, wherein the monocotyledonous plants are maize plants.

67. The method for restoring fertility to a progeny of a cytoplasmic male sterile parent plant of clause 64, wherein the male parent plant is isogenic to the female parent plant.

68. The method for restoring fertility to a progeny of a cytoplasmic male sterile parent plant of clause 64, wherein the male parent plant is homozygous or heterozygous for SEQ ID NO:8.

69. The method for restoring fertility to a progeny of a cytoplasmic male sterile parent plant of clause 64, the method further comprising introducing a desired trait into the cytoplasmic male sterile plant.

70. The method for restoring fertility to a progeny of a cytoplasmic male sterile parent plant of clause 64, the method further comprising:
   f) crossing the progeny cytoplasmic male sterile plant, with another plant comprising a desired trait to produce F1 progeny plants;
   g) selecting F1 progeny plants that have the desired trait to produce selected F1 progeny plants;
   h) crossing the selected F1 progeny plants with progeny cytoplasmic male sterile plant to produce backcross progeny plants;
   i) selecting for backcross progeny plants that have the desired trait; and,
   j) repeating steps (h) and (i) three or more times in succession to produce selected fourth or higher backcross progeny plants that comprise the desired trait.

71. The method for restoring fertility to a progeny of a cytoplasmic male sterile parent plant of clause 69, wherein the desired trait is selected from the group consisting of an insecticidal resistance trait, herbicide tolerant trait, disease resistance trait, yield increase trait, nutritional quality trait, agronomic increase trait, and combinations thereof.

72. An isolated polypeptide comprising an amino acid sequence of SEQ ID NO: 5.

73. An isolated polypeptide consisting of an amino acid sequence of SEQ ID NO: 5.

74. An isolated polypeptide consisting essentially of an amino acid sequence of SEQ ID NO: 5.

75. The isolated polypeptide of clause 72 comprising an amino acid sequence which has at least 85% sequence identity to SEQ ID NO: 7.

76. The isolated polypeptide of clause 72 consisting of an amino acid sequence which has at least 85% sequence identity to SEQ ID NO: 7.

77. The isolated polypeptide of clause 72 consisting essentially of an amino acid sequence which has at least 85% sequence identity to SEQ ID NO: 7.

78. The isolated polypeptide sequence of clause 72 or clause 75, wherein the polypeptide has cytoplasmic male sterile restorer activity.

79. A cell comprising the polypeptide of clause 72.

80. The cell of clause 79, wherein the cell is a plant cell.

81. A plant comprising the plant cell of clause 80.

82. The plant of clause 81, wherein the plant is a monocotyledonous plant.

83. The plant of clause 82, wherein the monocotyledonous plant is a maize plant.

84. The plant of clause 83, wherein the plant has CMS-S type cytoplasm.

85. A seed obtained from the plant of clause 81.

86. A synthetic nucleic acid sequence encoding the polypeptide of clause 72.

87. The synthetic nucleic acid sequence of clause 86 comprising the sequence of SEQ ID NO:8.

88. The synthetic nucleic acid sequence of clause 86 consisting of the sequence of SEQ ID NO:8.

89. The synthetic nucleic acid sequence of clause 86 consisting essentially of the sequence of SEQ ID NO:8.

90. The synthetic nucleic acid sequence of clause 86 comprising the sequence of SEQ ID NO:6.

91. The synthetic nucleic acid sequence of clause 86 consisting of the sequence of SEQ ID NO:6.

92. The synthetic nucleic acid sequence of clause 86 consisting essentially of the sequence of SEQ ID NO:6.

93. A gene expression cassette comprising the synthetic nucleic acid sequence of clause 86.

94. The gene expression cassette of clause 93, wherein the synthetic nucleic acid sequence is operably linked to a promoter, wherein the promoter is functional in plants.

95. The gene expression cassette of clause 94, wherein the promoter is a plant cytoplasmic male sterile promoter.

96. A cell comprising the gene expression cassette of clause 93.

97. A vector comprising the synthetic nucleic acid sequence of clause 86.

98. A cell comprising the vector of clause 97.

99. A method for restoring fertility to a cytoplasmic male sterile plant, the method comprising the steps of;
a) transforming the cytoplasmic male sterile plant with the synthetic nucleic acid sequence of clause 86;
b) integrating the synthetic nucleic acid sequence into the genome of the cytoplasmic male sterile plant; and,
c) expressing the synthetic nucleic acid sequence, wherein expression of the synthetic nucleic acid sequence restores fertility to the cytoplasmic male sterile plant.

100. A method for altering plant morphology in a cytoplasmic male sterile plant, the method comprising the steps of;
a) transforming the cytoplasmic male sterile plant with the synthetic nucleic acid sequence of clause 86;
b) integrating the synthetic nucleic acid sequence into the genome of the cytoplasmic male sterile plant; and,
c) expressing the synthetic nucleic acid sequence, wherein expression of the synthetic nucleic acid sequence alters plant morphology in the cytoplasmic male sterile plant.

101. A method of detecting a plant comprising a cytoplasmic male sterile restorer trait, the method comprising the steps of:
a) isolating a genomic polynucleotide sample from a plant, plant tissue, plant part, or plant cell;
b) adding a set of oligonucleotide primers to the genomic polynucleotide sample;
c) subjecting the genomic polynucleotide sample and the set of oligonucleotide primers to an amplification process; and,
d) detecting at least one amplified product, wherein the amplified product indicates the presence of the cytoplasmic male sterile restorer trait in the plant.

102. The method of detecting a plant comprising a cytoplasmic male sterile restorer trait of clause 101, wherein the set of oligonucleotide primers are selected from the group consisting of SEQ ID NO:28, SEQ ID NO:29, and SEQ ID NO:30.

103. The method of detecting a plant comprising a cytoplasmic male sterile restorer trait of clause 101, wherein the amplified product comprises SEQ ID NO:6.

104. The method of detecting a plant comprising a cytoplasmic male sterile restorer trait of clause 101, wherein the amplified product consists of SEQ ID NO:6.

105. The method of detecting a plant comprising a cytoplasmic male sterile restorer trait of clause 101, wherein the amplified product consists essentially of SEQ ID NO:6.

106. The method of detecting a plant comprising a cytoplasmic male sterile restorer trait of clause 101, wherein the amplified product comprises a fragment of SEQ ID NO:8.

107. The method of detecting a plant comprising a cytoplasmic male sterile restorer trait of clause 101, wherein the amplified product consists of a fragment of SEQ ID NO:8.

108. The method of detecting a plant comprising a cytoplasmic male sterile restorer trait of clause 101, wherein the amplified product consists essentially of a fragment of SEQ ID NO:8.

109. The method of detecting a plant comprising a cytoplasmic male sterile restorer trait of clause 101, wherein the amplified product comprises a fragment of SEQ ID NO:12.

110. The method of detecting a plant comprising a cytoplasmic male sterile restorer trait of clause 101, wherein the amplified product consists of a fragment of SEQ ID NO:12.

111. The method of detecting a plant comprising a cytoplasmic male sterile restorer trait of clause 101, wherein the amplified product consists essentially of a fragment of SEQ ID NO:12.

112. The method of detecting a plant comprising a cytoplasmic male sterile restorer trait of clause 101, wherein the amplified product is quantitated.

113. The method of detecting an expression level of a cytoplasmic male sterile restorer trait, the method comprising the steps of:
a) performing a first amplification process using a cytoplasmic male sterile restorer trait probe (SEQ ID NO:30), a forward cytoplasmic male sterile restorer trait primer (SEQ ID NO:28) and a reverse cytoplasmic male sterile restorer trait primer (SEQ ID NO:29) on a genomic polynucleotide sample, wherein a first fluorescent dye is released from the cytoplasmic male sterile restorer trait probe (SEQ ID NO:30);
b) performing a second amplification process using a reference probe (SEQ ID NO:36), a forward reference primer (SEQ ID NO:34) and a reverse reference primer (SEQ ID NO:35) on the genomic polynucleotide sample, wherein a second fluorescent dye is released from the reference probe (SEQ ID NO:36); and,
c) quantitating the relative intensity of the first fluorescent dye to the second fluorescent dye to detect the expression level of the cytoplasmic male sterile restorer trait.

114. The method of detecting an expression level of a cytoplasmic male sterile restorer trait of clause 113, wherein the first and second amplification processes are performed in a single PCR assay tube using probes with different fluorescent dyes.

115. The method of detecting an expression level of a cytoplasmic male sterile restorer trait of clause 113, the method further comprising the steps of:
   d) loading a PCR solution in a single PCR assay tube, the PCR solution comprising a polymerase with 5' to 3' nuclease activity, deoxynucleotides, the primers, the probes, a buffer, and the genomic polynucleotide sample;
   e) amplifying the PCR solution, wherein the PCR solution is treated under amplification conditions such that the 5' to 3' nuclease activity of the polymerase cleaves the probes thereby releasing the fluorescent dye that emits light; and,
   f) measuring the light emitted from fluorescent dye, during the amplification.

116. The method of detecting an expression level of a cytoplasmic male sterile restorer trait of clause 113, wherein the cytoplasmic male sterile trait probe comprises the first fluorescent dye and a first quencher.

117. The method of detecting an expression level of a cytoplasmic male sterile restorer trait of clause 116, wherein the first fluorescent dye is selected from the group consisting of a HEX fluorescent dye, a VIC fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, or a ROX fluorescent dye.

118. The method of detecting an expression level of a cytoplasmic male sterile restorer trait of clause 116, wherein the first quencher is selected from the group consisting of a Dabcyl quencher, a Tamra quencher, a Qxl quencher, an Iowa Black FQ quencher, an Iowa Black RQ quencher, an IR Dye QC-1 quencher, a MGB quencher, or a Blackhole quencher.

119. The method of detecting an expression level of a cytoplasmic male sterile restorer trait of clause 113, wherein the reference probe comprises the second fluorescent dye and a second quencher.

120. The method of detecting an expression level of a cytoplasmic male sterile restorer trait of clause 119, wherein the second fluorescent dye is selected from the group consisting of a HEX fluorescent dye, a FAM fluorescent dye, a VIC fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, or a ROX fluorescent dye.

121. The method of detecting an expression level of a cytoplasmic male sterile restorer trait of clause 119, wherein the second quencher is selected from the group consisting of a Dabcyl quencher, a Tamra quencher, a Qxl quencher, an Iowa Black FQ quencher, an Iowa Black RQ quencher, an IR Dye QC-1 quencher, a MGB quencher, or a Blackhole quencher.

122. The method of detecting an expression level of a cytoplasmic male sterile restorer trait of clause 113 or clause 101, wherein the genomic polynucleotide sample comprises cDNA produced from mRNA isolated from a plant, plant tissue, plant part, or plant cell.

123. A cell comprising the polypeptide of clause 4.

124. The cell of clause 123, wherein the cell is a plant cell.

125. A plant comprising the plant cell of clause 124.

126. The plant of clause 125, wherein the plant is a monocotyledonous plant.

127. The plant of clause 126, wherein the monocotyledonous plant is a maize plant.

128. A seed obtained from the plant of clause 125.

129. A synthetic nucleic acid sequence encoding the polypeptide of clause 4.

130. The synthetic nucleic acid sequence of clause 129 comprising a sequence with at least 90% sequence identity to the sequence of SEQ ID NO:4.

131. The synthetic nucleic acid sequence of clause 129 consisting of the sequence of SEQ ID NO:4.

132. The synthetic nucleic acid sequence of clause 129 consisting essentially of the sequence of SEQ ID NO:4.

133. A polynucleotide comprising the synthetic nucleic acid sequence of clause 129.

134. The polynucleotide of clause 133, wherein the polynucleotide is operably linked to a promoter, wherein the promoter is functional in plants.

135. The polynucleotide of clause 134, wherein the promoter is a plant cytoplasmic male sterile promoter.

136. A cell comprising the polynucleotide of clause 133.

137. A vector comprising the synthetic nucleic acid sequence of clause 129.

138. A cell comprising the vector of clause 137.

139. The plant of clause 125, wherein the plant has CMS-S type cytoplasm.

III. Terms

Unless defined otherwise, all technical and scientific terms used herein have the same meaning as commonly understood by one of ordinary skill in the art to which this disclosure relates. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

In order to further clarify this disclosure, the following terms, abbreviations and definitions are provided.

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of an embodiment of the disclosure are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as disclosed in the application.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, and includes protoplast cells without a cell wall and plant cells with a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

As used herein, the term "isolated" refers to a biological component (including a nucleic acid or protein) that has been separated, produced apart from other biological components in the cell of the organism in which the component naturally occurs (i.e., other chromosomal and extra-chromosomal DNA and RNA, and proteins).

As used herein, the term "purified" in reference to nucleic acid molecules does not require absolute purity (such as a homogeneous preparation); instead, it represents an indication that the sequence is relatively more pure than in its native cellular environment (compared to the natural level this level should be at least 2-5 fold greater, e.g., in terms of concentration or gene expression levels). The claimed DNA molecules obtained directly from total DNA or from total RNA. In addition, cDNA clones are not naturally occurring, but rather are preferably obtained via manipulation of a partially purified, naturally occurring substance (messenger RNA). The construction of a cDNA library from mRNA involves the creation of a library. Individual cDNA clones can be produced from the library by clonal selection of the cells carrying the cDNA library. Thus, the process which includes the construction of a cDNA library from mRNA and selection of distinct cDNA clones yields an approximately $10^6$-fold purification of the native message. Likewise, a promoter or gene DNA sequence could be cloned into a plasmid. Such a clone is not naturally occurring, but rather is preferably obtained via manipulation of a partially purified, naturally occurring substance such as a genomic DNA library. Thus, purification of at least one order of magnitude, preferably two or three orders, and more preferably four or five orders of magnitude is favored in these techniques.

Similarly, synthetic represents an indication that a chemical or functional change in the component DNA sequence has occurred. Nucleic acid molecules and proteins that have been "synthesized" include nucleic acid molecules and proteins generated by PCR amplification or by recombinant methods, wherein an isolated polynucleotide is further modified by the incorporation within a plasmid or vector. The term "synthetic" also embraces nucleic acids and proteins prepared by recombinant DNA methods in a host cell (e.g., plant cells), as well as chemically-synthesized nucleic acid molecules, proteins, and peptides.

In engineering a gene for expression in plants, the codon bias of the prospective host plant(s) may be determined, for example, through use of publicly available DNA sequence databases to find information about the codon distribution of plant genomes or the protein coding regions of various plant genes. Once an optimized (e.g., a plant-optimized) DNA sequence has been designed on paper, or in silico, actual DNA molecules may be synthesized in the laboratory to correspond in sequence precisely to the designed sequence. Such synthetic nucleic acid molecule molecules can be cloned and otherwise manipulated exactly as if they were derived from natural or native sources.

As used herein, the terms "polynucleotide," "nucleic acid," and "nucleic acid molecule" are used interchangeably, and may encompass a singular nucleic acid; plural nucleic acids; a nucleic acid fragment, variant, or derivative thereof; and nucleic acid construct (e.g., messenger RNA (mRNA) and plasmid DNA (pDNA)). A polynucleotide or nucleic acid may contain the nucleotide sequence of a full-length cDNA sequence, or a fragment thereof, including untranslated 5' and/or 3' sequences and coding sequence(s). A polynucleotide or nucleic acid may be comprised of any polyribonucleotide or polydeoxyribonucleotide, which may include unmodified ribonucleotides or deoxyribonucleotides or modified ribonucleotides or deoxyribonucleotides. For example, a polynucleotide or nucleic acid may be comprised of single- and double-stranded DNA; DNA that is a mixture of single- and double-stranded regions; single- and double-stranded RNA; and RNA that is mixture of single- and double-stranded regions. Hybrid molecules comprising DNA and RNA may be single-stranded, double-stranded, or a mixture of single- and double-stranded regions. The foregoing terms also include chemically, enzymatically, and metabolically modified forms of a polynucleotide or nucleic acid.

It is understood that a specific DNA refers also to the complement thereof, the sequence of which is determined according to the rules of deoxyribonucleotide base-pairing.

As used herein, the term "gene" refers to a nucleic acid that encodes a functional product (RNA or polypeptide/protein). A gene may include regulatory sequences preceding (5' non-coding sequences) and/or following (3' non-coding sequences) the sequence encoding the functional product.

As used herein, the term "coding sequence" refers to a nucleic acid sequence that encodes a specific amino acid sequence. A "regulatory sequence" refers to a nucleotide sequence located upstream (e.g., 5' non-coding sequences), within, or downstream (e.g., 3' non-coding sequences) of a coding sequence, which influence the transcription, RNA processing or stability, or translation of the associated coding sequence. Regulatory sequences include, for example and without limitation: promoters; translation leader sequences; introns; polyadenylation recognition sequences; RNA processing sites; effector binding sites; and stem-loop structures.

As used herein, the term "polypeptide" includes a singular polypeptide, plural polypeptides, and fragments thereof. This term refers to a molecule comprised of monomers (amino acids) linearly linked by amide bonds (also known as peptide bonds). The term "polypeptide" refers to any chain or chains of two or more amino acids, and does not refer to a specific length or size of the product. Accordingly, peptides, dipeptides, tripeptides, oligopeptides, protein, amino acid chain, and any other term used to refer to a chain or chains of two or more amino acids, are included within the definition of "polypeptide," and the foregoing terms are used interchangeably with "polypeptide" herein. A polypeptide may be isolated from a natural biological source or produced by recombinant technology, but a specific polypeptide is not necessarily translated from a specific nucleic acid. A polypeptide may be generated in any appropriate manner, including for example and without limitation, by chemical synthesis.

As used herein, the term "native" refers to the form of a polynucleotide, gene or polypeptide that is found in nature with its own regulatory sequences, if present. The term "endogenous" refers to the native form of the polynucleotide, gene or polypeptide in its natural location in the organism or in the genome of the organism.

In contrast, the term "heterologous" refers to a polynucleotide, gene or polypeptide that is not normally found at its location in the reference (host) organism. For example, a heterologous nucleic acid may be a nucleic acid that is normally found in the reference organism at a different genomic location. By way of further example, a heterologous nucleic acid may be a nucleic acid that is not normally found in the reference organism. A host organism comprising a hetereologous polynucleotide, gene or polypeptide may be produced by introducing the heterologous polynucleotide, gene or polypeptide into the host organism. In particular examples, a heterologous polynucleotide comprises a native coding sequence, or portion thereof, that is reintroduced into a source organism in a form that is different from the corresponding native polynucleotide. In particular examples, a heterologous gene comprises a native coding sequence, or portion thereof, that is reintroduced into a source organism in a form that is different from the corresponding native gene. For example, a heterologous gene may include a native coding sequence that is a portion of a chimeric gene including non-native regulatory regions that is reintroduced into the native host. In particular examples, a heterologous polypeptide is a native polypeptide that is reintroduced into a source organism in a form that is different from the corresponding native polypeptide.

A heterologous gene or polypeptide may be a gene or polypeptide that comprises a functional polypeptide or nucleic acid sequence encoding a functional polypeptide that is fused to another genes or polypeptide to produce a chimeric or fusion polypeptide, or a gene encoding the same. Genes and proteins of particular embodiments include specifically exemplified full-length sequences and portions, segments, fragments (including contiguous fragments and internal and/or terminal deletions compared to the full-length molecules), variants, mutants, chimerics, and fusions of these sequences.

As used herein, the term "modification" may refer to a change in a particular reference polynucleotide that results in reduced, substantially eliminated, or eliminated activity of a polypeptide encoded by the reference polynucleotide. A modification may also refer to a change in a reference polypeptide that results in reduced, substantially eliminated, or eliminated activity of the reference polypeptide. Alternatively, the term "modification" may refer to a change in a reference polynucleotide that results in increased or enhanced activity of a polypeptide encoded by the reference polynucleotide, as well as a change in a reference polypeptide that results in increased or enhanced activity of the reference polypeptide. Changes such as the foregoing may be made by any of several methods well-known in the art including, for example and without limitation: deleting a portion of the reference molecule; mutating the reference molecule (e.g., via spontaneous mutagenesis, via random mutagenesis, via mutagenesis caused by mutator genes, and via transposon mutagenesis); substituting a portion of the reference molecule; inserting an element into the reference molecule; down-regulating expression of the reference molecule; altering the cellular location of the reference molecule; altering the state of the reference molecule (e.g., via methylation of a reference polynucleotide, and via phosphorylation or ubiquitination of a reference polypeptide); removing a cofactor of the reference molecule; introduction of an antisense RNA/DNA targeting the reference molecule; introduction of an interfering RNA/DNA targeting the reference molecule; chemical modification of the reference molecule; covalent modification of the reference molecule; irradiation of the reference molecule with UV radiation or X-rays; homologous recombination that alters the reference molecule; mitotic recombination that alters the reference molecule; replacement of the promoter of the reference molecule; and/or combinations of any of the foregoing.

Guidance in determining which nucleotides or amino acid residues may be modified in a specific example may be found by comparing the sequence of the reference polynucleotide or polypeptide with that of homologous (e.g., homologous yeast or bacterial) polynucleotides or polypeptides, and maximizing the number of modifications made in regions of high homology (conserved regions) or consensus sequences.

The term "promoter" refers to a DNA sequence capable of controlling the expression of a nucleic acid coding sequence or functional RNA. In examples, the controlled coding sequence is located 3' to a promoter sequence. A promoter may be derived in its entirety from a native gene, a promoter may be comprised of different elements derived from different promoters found in nature, or a promoter may even comprise synthetic DNA segments. It is understood by those skilled in the art that different promoters can direct the expression of a gene in different tissues or cell types, or at different stages of development, or in response to different environmental or physiological conditions. Examples of all of the foregoing promoters are known and used in the art to control the expression of heterologous nucleic acids. Promoters that direct the expression of a gene in most cell types at most times are commonly referred to as "constitutive promoters." Furthermore, while those in the art have (in many cases unsuccessfully) attempted to delineate the exact boundaries of regulatory sequences, it has come to be understood that DNA fragments of different lengths may have identical promoter activity. The promoter activity of a particular nucleic acid may be assayed using techniques familiar to those in the art.

The term "operably linked" refers to an association of nucleic acid sequences on a single nucleic acid, wherein the function of one of the nucleic acid sequences is affected by another. For example, a promoter is operably linked with a coding sequence when the promoter is capable of effecting the expression of that coding sequence (e.g., the coding sequence is under the transcriptional control of the promoter). A coding sequence may be operably linked to a regulatory sequence in a sense or antisense orientation.

The term "expression" or "expressing," as used herein, may refer to the transcription and stable accumulation of sense (mRNA) or antisense RNA derived from a DNA. Expression may also refer to translation of mRNA into a polypeptide. As used herein, the term "overexpression" refers to expression that is higher than endogenous expression of the same gene or a related gene. Thus, a heterologous gene is "overexpressed" if its expression is higher than that of a comparable endogenous gene.

As used herein, the term "transformation" or "transforming" refers to the transfer and integration of a nucleic acid or fragment thereof into a host organism, resulting in genetically stable inheritance. Host organisms containing a transforming nucleic acid are referred to as "transgenic," "recombinant," or "transformed" organisms. Known methods of transformation include, for example: *Agrobacterium tumefaciens-* or *A. rhizogenes*-mediated transformation; calcium phosphate transformation; polybrene transformation; protoplast fusion; electroporation; ultrasonic methods (e.g., sonoporation); liposome transformation; microinjection; transformation with naked DNA; transformation with plasmid vectors; transformation with viral vectors; biolistic transformation (microparticle bombardment); silicon carbide WHISKERS-mediated transformation; aerosol beaming; and PEG-mediated transformation.

As used herein, the term "introduced" (in the context of introducing a nucleic acid into a cell) includes transformation of a cell, as well as crossing a plant comprising the nucleic acid with a second plant, such that the second plant contains the nucleic acid, as may be performed utilizing conventional plant breeding techniques. Such breeding techniques are known in the art. For a discussion of plant breeding techniques, see Poehlman (1995) Breeding Field Crops, 4th Edition, AVI Publication Co., Westport Conn.

Backcrossing methods may be used to introduce a nucleic acid into a plant. This technique has been used for decades to introduce traits into plants. An example of a description of backcrossing (and other plant breeding methodologies) can be found in, for example, Poelman (1995), supra; and Jensen (1988) Plant Breeding Methodology, Wiley, New York, N.Y. In an exemplary backcross protocol, an original plant of interest (the "recurrent parent") is crossed to a second plant (the "non-recurrent parent") that carries the nucleic acid be introduced. The resulting progeny from this cross are then crossed again to the recurrent parent, and the process is repeated until a converted plant is obtained, wherein essentially all of the desired morphological and physiological characteristics of the recurrent parent are recovered in the converted plant, in addition to the nucleic acid from the non-recurrent parent.

As used herein, the term "isogenic" refers to two individual plants (or portions thereof e.g., seeds, cells) having a substantially identical genotype (e.g., not more than 1 gene is different between the individuals).

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

The terms "plasmid" and "vector," as used herein, refer to an extra chromosomal element that may carry one or more gene(s) that are not part of the central metabolism of the cell. Plasmids and vectors typically are circular double-stranded DNA molecules. However, plasmids and vectors may be linear or circular nucleic acids, of a single- or double-stranded DNA or RNA, and may be derived from any source, in which a number of nucleotide sequences have been joined or recombined into a unique construction that is capable of introducing a promoter fragment and a coding DNA sequence along with any appropriate 3' untranslated sequence into a cell. In examples, plasmids and vectors may comprise autonomously replicating sequences, genome integrating sequences, and/or phage or nucleotide sequences.

Polypeptide and "protein" are used interchangeably herein and include a molecular chain of two or more amino acids linked through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be synthesized, or expressed recombinantly using known protein engineering techniques. In addition, inventive fusion proteins can be derivatized as described herein by well-known organic chemistry techniques.

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

IV. Embodiments of the Present Invention

In one embodiment, the subject disclosure relates to an isolated polypeptide comprising an amino acid sequence of SEQ ID NO:1. In a further embodiment, the isolated polypeptide of SEQ ID NO:1 comprises an amino acid sequence which has at least 85% sequence identity to SEQ ID NO:3. In aspects of the embodiment, the isolated polypeptides of SEQ ID NO:1 and SEQ ID NO:3 have cytoplasmic male sterile activity.

In another embodiment, the subject disclosure relates to an isolated polypeptide consisting of an amino acid sequence of SEQ ID NO:1. In another embodiment, the subject disclosure relates to an isolated polypeptide consisting essentially of an amino acid sequence of SEQ ID NO:1.

In a further embodiment, the isolated polypeptide of SEQ ID NO:1 consists of an amino acid sequence which has at least 85% sequence identity to SEQ ID NO:3. In a further embodiment, the isolated polypeptide of SEQ ID NO:1 consists essentially of an amino acid sequence which has at least 85% sequence identity to SEQ ID NO:3.

In another embodiment, the disclosure relates to a cell comprising the isolated polypeptide of SEQ ID NO:1. In an aspect, the cell comprising the isolated polypeptide of SEQ ID NO:1 can be a plant cell. In further aspects, the subject disclosure relates to a plant comprising the plant cell comprising the isolated polypeptide of SEQ ID NO:1. In another embodiment, the plant is a monocotyledonous plant. In further embodiments, the monocotyledonous plant is a maize plant. In another embodiment, the maize plant has CMS-S type cytoplasm. Further aspects of the subject disclosure relate to seed obtained from the plant comprising the plant cell comprising the isolated polypeptide of SEQ ID NO:1.

In an additional embodiment, the disclosure relates to a synthetic nucleic acid sequence encoding the polypeptide of SEQ ID NO:1. In a further embodiment, the polypeptide of SEQ ID NO:1 is encoded by the sequence of SEQ ID NO:2. In another embodiment, a polynucleotide comprises the sequence of SEQ ID NO:2. In another aspect, a polynucleotide consists of the sequence of SEQ ID NO:2. In a further aspect, a polynucleotide consists essentially of the sequence of SEQ ID NO:2. In a further aspect the polynucleotide comprising the sequence of SEQ ID NO:2 is operably linked to a promoter, wherein the promoter is functional in plants. In yet another aspect, the promoter is a plant cytoplasmic male sterile promoter. In another embodiment, the disclosure relates to a cell comprising the polynucleotide that further comprises the sequence of SEQ ID NO:2. In another embodiment, the disclosure relates to a cell consists of the polynucleotide that further comprises the sequence of SEQ ID NO:2. In another embodiment, the disclosure relates to a cell consists essentially of the polynucleotide that further comprises the sequence of SEQ ID NO:2. In a further embodiment, the disclosure relates to a vector comprising the polynucleotide that further comprises the sequence of SEQ ID NO:2. In a further embodiment, the disclosure relates to a vector consisting of the polynucleotide that further comprises the sequence of SEQ ID NO:2. In a further embodiment, the disclosure relates to a vector consisting essentially of the polynucleotide that further comprises the sequence of SEQ ID NO:2.

Furthermore, the subject disclosure relates to a method for producing a progeny cytoplasmic male sterile plant, comprising the steps of:
  a) crossing a female parent plant with a male parent plant, wherein the female parent plant is a cytoplasmic male sterile parent plant homozygous for SEQ ID NO:4, and wherein the male parent plant is a fertile parent plant;
  b) harvesting a progeny seed from the cross of step (a), wherein the progeny seed is homozygous for SEQ ID NO:4;
  c) planting the progeny seed; and,
  d) growing the progeny seed, wherein the progeny seed produce the progeny cytoplasmic male sterile plant, wherein the progeny cytoplasmic male sterile plant is homozygous for SEQ ID NO:4.

In a further aspect, the method relates to producing the progeny cytoplasmic male sterile plant wherein the female and male parent plants are monocotyledonous plants. In another embodiment, the monocotyledonous plants are maize plants. In a further embodiment, the maize plant has CMS-S type cytoplasm. In yet another embodiment, the male parent plant is isogenic to the female parent plant. In a subsequent embodiment, the maize plants are homozygous or heterozygous for SEQ ID NO:8. In another embodiment, the method further comprises introducing a desired trait into the progeny cytoplasmic male sterile plant. In a subsequent embodiment, the desired trait is selected from the group consisting of an insecticidal resistance trait, herbicide tolerant trait, disease resistance trait, yield increase trait, nutritional quality trait, agronomic increase trait, and combinations thereof.

In yet another aspect, the subject disclosure relates to a method for producing a progeny cytoplasmic male sterile plant, the method further comprising the steps of:
  e) crossing the progeny cytoplasmic male sterile plant, with another plant comprising a desired trait to produce F1 progeny plants;
  f) selecting F1 progeny plants that have the desired trait to produce selected F1 progeny plants;
  g) crossing the selected F1 progeny plants with the progeny cytoplasmic male sterile plant to produce backcross progeny plants;
  h) selecting for backcross progeny plants that have the desired trait; and,
  i) repeating steps (g) and (h) three or more times in succession to produce selected fourth or higher backcross progeny plants that comprise the desired trait.

Further aspects of the subject disclosure relate to a method for restoring fertility to a progeny of a cytoplasmic male sterile parent plant, the method comprising:
  a) crossing a female parent plant with a male parent plant, wherein the female parent plant is a cytoplasmic male sterile parent plant homozygous or heterozygous for SEQ ID NO:8, and wherein the cytoplasmic male sterile plant is a fertile parent plant;
  b) harvesting a progeny seed from the cross of step (a), wherein the progeny seed is homozygous or heterozygous for SEQ ID NO:8;
  c) planting the progeny seed;
  d) growing the progeny seed, wherein the progeny seed produce a progeny cytoplasmic male fertile plant; and,
  e) restoring fertility to the progeny of the cytoplasmic male sterile parent plant, wherein the progeny cytoplasmic male fertile plant is homozygous or heterozygous for SEQ ID NO:8.

In a further aspect, the method relates to producing the progeny cytoplasmic male fertile plant wherein the female and male parent plants are monocotyledonous plants. In another embodiment, the monocotyledonous plants are maize plants. In yet another embodiment, the maize plant has CMS-S type cytoplasm. In a further embodiment, the male parent plant is isogenic to the female parent plant. In a subsequent embodiment, the maize plants are homozygous or heterozygous for SEQ ID NO:8. In another embodiment, the method further comprises introducing a desired trait into the progeny cytoplasmic male sterile plant. In another embodiment, the desired trait is selected from the group consisting of an insecticidal resistance trait, herbicide tolerant trait, disease resistance trait, yield increase trait, nutritional quality trait, agronomic increase trait, and combinations thereof.

In yet another aspect, the subject disclosure relates to a method for producing a progeny of a cytoplasmic male sterile parent plant, the method further comprising the steps of:

f) crossing the progeny cytoplasmic male sterile plant, with another plant comprising a desired trait to produce F1 progeny plants;
g) selecting F1 progeny plants that have the desired trait to produce selected F1 progeny plants;
h) crossing the selected F1 progeny plants with the progeny cytoplasmic male sterile plant to produce backcross progeny plants;
i) selecting for backcross progeny plants that have the desired trait; and,
j) repeating steps (g) and (h) three or more times in succession to produce selected fourth or higher backcross progeny plants that comprise the desired trait.

In an embodiment, the subject disclosure relates to an isolated polypeptide comprising an amino acid sequence of SEQ ID NO:5. In a further embodiment, the isolated polypeptide of SEQ ID NO:5 comprises an amino acid sequence which has at least 85% sequence identity to SEQ ID NO:7. In aspects of the embodiment, the isolated polypeptides of SEQ ID NO:5 and SEQ ID NO:7 have cytoplasmic male sterile restorer activity.

In an embodiment, the subject disclosure relates to an isolated polypeptide consisting of an amino acid sequence of SEQ ID NO:5. In an embodiment, the subject disclosure relates to an isolated polypeptide consisting essentially of an amino acid sequence of SEQ ID NO:5. In a further embodiment, the isolated polypeptide of SEQ ID NO:5 consisting of an amino acid sequence which has at least 85% sequence identity to SEQ ID NO:7. In a further embodiment, the isolated polypeptide of SEQ ID NO:5 consisting essentially of an amino acid sequence which has at least 85% sequence identity to SEQ ID NO:7.

In another embodiment, the disclosure relates to a cell comprising the isolated polypeptide of SEQ ID NO:5. In an aspect, the cell comprising the isolated polypeptide of SEQ ID NO:5 can be a plant cell. In further aspects, the subject disclosure relates to a plant comprising the plant cell comprising the isolated polypeptide of SEQ ID NO:5. In another embodiment, the plant is a monocotyledonous plant. In further embodiments, the monocotyledonous plant is a maize plant. In another embodiment, the maize plant has CMS-S type cytoplasm. Further aspects of the subject disclosure relate to seed obtained from the plant comprising the plant cell comprising the isolated polypeptide of SEQ ID NO:5.

In an additional embodiment, the disclosure relates to a synthetic nucleic acid sequence encoding the polypeptide of SEQ ID NO:5. In a further embodiment, the synthetic nucleic acid sequence comprises the sequence of SEQ ID NO:5. In another embodiment, the synthetic nucleic acid sequence consists of the sequence of SEQ ID NO:5. In an additional embodiment, the synthetic nucleic acid sequence consists essentially of the sequence of SEQ ID NO:5. In a further embodiment, the synthetic nucleic acid sequence comprises the sequence of SEQ ID NO:8. In another embodiment, the synthetic nucleic acid sequence consists of the sequence of SEQ ID NO:8. In an additional embodiment, the synthetic nucleic acid sequence consists essentially of the sequence of SEQ ID NO:8. In another embodiment, a gene expression cassette comprises the synthetic sequence of SEQ ID NO:8. In a further aspect, the gene expression cassette comprising the sequence of SEQ ID NO:8 is operably linked to a promoter, wherein the promoter is functional in plants. In yet another aspect, the promoter is a plant cytoplasmic male sterile promoter. In another embodiment, the disclosure relates to a cell comprising the gene expression cassette that further comprises the sequence of SEQ ID NO:8. In an embodiment, the disclosure relates to a cell comprising the gene expression cassette that consists of the sequence of SEQ ID NO:8. In an additional embodiment, the disclosure relates to a cell consisting essentially of the gene expression cassette that further comprises the sequence of SEQ ID NO:8. In a further embodiment, the disclosure relates to a gene expression cassette comprising the polynucleotide that further comprises the sequence of SEQ ID NO:8. In a subsequent embodiment, the disclosure relates to a gene expression cassette consisting of the polynucleotide that consists of the sequence of SEQ ID NO:8. In another embodiment, the disclosure relates to a gene expression cassette comprising the polynucleotide that consists essentially of the sequence of SEQ ID NO:8.

Further aspects of the subject disclosure relate to a method for restoring fertility to a cytoplasmic male sterile plant, the method comprising:
a) transforming the cytoplasmic male sterile plant with the synthetic nucleic acid sequence encoding the polypeptide of SEQ ID NO:5;
b) integrating the synthetic nucleic acid sequence into the genome of the cytoplasmic male sterile plant; and,
c) expressing the synthetic nucleic acid sequence, wherein expression of the synthetic nucleic acid sequence restores fertility to the cytoplasmic male sterile plant.

Other aspects of the subject disclosure relate to a method for altering the morphology of a cytoplasmic male sterile plant, the method comprising:
a) transforming the cytoplasmic male sterile plant with the synthetic nucleic acid sequence encoding the polypeptide of SEQ ID NO:5;
b) integrating the synthetic nucleic acid sequence into the genome of the cytoplasmic male sterile plant; and,
c) expressing the synthetic nucleic acid sequence, wherein expression of the synthetic nucleic acid sequence alters the morphology of the cytoplasmic male sterile plant.

In an embodiment, the subject disclosure relates to a method of detecting a plant comprising a cytoplasmic male sterile restorer trait, the method comprising the steps of:
a) isolating a genomic polynucleotide sample from a plant, plant tissue, plant part, or plant cell;
b) adding a set of oligonucleotide primers to the genomic polynucleotide sample;
c) subjecting the genomic polynucleotide sample and the set of oligonucleotide primers to an amplification process; and,
d) detecting at least one amplified product, wherein the amplified product indicates the presence of the cytoplasmic male sterile trait in the plant.

Further embodiments relate to a method for detecting a plant comprising a cytoplasmic male sterile restorer trait, include the set of oligonucleotide primers that are selected from the group consisting of SEQ ID NO:28, SEQ ID NO:29, and SEQ ID NO:30. In another embodiment, the amplified product comprises SEQ ID NO:6. In an embodiment, the amplified product consists of SEQ ID NO:6. In a further embodiment, the amplified product consists essentially of SEQ ID NO:6. Further embodiments include the quantitation of the amplified product.

Other aspects of the subject disclosure relate to a method of detecting an expression level of a cytoplasmic male sterile restorer trait, the method comprising the steps of:
a) performing a first amplification process using a cytoplasmic male sterile restorer trait probe (SEQ ID NO:30), a forward cytoplasmic male sterile restorer trait primer (SEQ ID NO:28) and a reverse cytoplasmic male sterile restorer trait primer (SEQ ID NO:29) on a genomic polynucleotide sample, wherein a first fluorescent dye is released from the cytoplasmic male sterile restorer trait probe (SEQ ID NO:30);

b) performing a second amplification process using a reference probe (SEQ ID NO:36), a forward reference primer (SEQ ID NO:34) and a reverse reference primer (SEQ ID NO:35) on the genomic polynucleotide sample, wherein a second fluorescent dye is released from the reference probe (SEQ ID NO:36);

c) quantitating the relative intensity of the first fluorescent dye to the second fluorescent dye to detect the expression level of the cytoplasmic male sterile restorer trait.

Further embodiments relate to the method of detecting an expression level of a cytoplasmic male sterile restorer trait, include where the first and second amplification processes are performed in a single PCR assay tube using probes with different fluorescent dyes.

In a further embodiment, the method of detecting an expression level of a cytoplasmic male sterile restorer trait comprises the steps of;

d) loading a PCR solution in a single PCR assay tube, the PCR solution comprising a polymerase with 5' to 3' nuclease activity, deoxynucleotides, the primers, the probes, a buffer, and the genomic polynucleotide sample;

e) amplifying the PCR solution, wherein the PCR solution is treated under amplification conditions such that the 5' to 3' nuclease activity of the polymerase cleaves the probes thereby releasing the fluorescent dye that emits light; and, f) measuring the light emitted from fluorescent dye, during the amplification.

Further embodiments relate to the method of detecting an expression level of a cytoplasmic male sterile restorer trait, include the cytoplasmic male sterile restorer trait probe comprising the first fluorescent dye and a first quencher. In a subsequent embodiment, the first fluorescent dye is selected from the group consisting of a HEX fluorescent dye, a VIC fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, or a ROX fluorescent dye. In a further embodiment, the first quencher is selected from the group consisting of a Dabcyl quencher, a Tamra quencher, a Qxl quencher, an Iowa Black FQ quencher, an Iowa Black RQ quencher, an IR Dye QC-1 quencher, a MGB quencher, or a Blackhole quencher. In yet another embodiment, the reference probe comprises the second fluorescent dye and a second quencher. In a subsequent embodiment, the second fluorescent dye is selected from the group consisting of a HEX fluorescent dye, a FAM fluorescent dye, a VIC fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, or a ROX fluorescent dye. In another embodiment, the second quencher is selected from the group consisting of a Dabcyl quencher, a Tamra quencher, a Qxl quencher, an Iowa Black FQ quencher, an Iowa Black RQ quencher, an IR Dye QC-1 quencher, a MGB quencher, or a Blackhole quencher. In a further embodiment, the genomic polynucleotide sample comprises cDNA produced from mRNA isolated from a plant, plant tissue, plant part, or plant cell.

In one embodiment of the present disclosure, a polynucleotide donor cassette comprising an isolated polypeptide comprising an amino acid sequence of SEQ ID NO: 1 is provided. In a further embodiment, the isolated polypeptide of SEQ ID NO:1 further comprises an amino acid sequence with at least 85% sequence identity to SEQ ID NO:3. In a subsequent embodiment, the isolated polypeptide of SEQ ID NO:1 and a polypeptide with 85% sequence identity to SEQ ID NO:3 have cytoplasmic male sterile activity.

Cytoplasmic male sterile systems have been used to breed hybrids in a number of crop species. The use of such a sterility system can be cost-effective and labor conscious. In maize or corn, for example, the expensive and laborious task of detasselling is avoided when cytoplasmic male sterility is utilized to avoid self-pollinating. The use of the cytoplasmic male sterile system in a breeding program is also advantageous because of its simplicity and cost savings.

Cytoplasmic male sterility, a maternally inherited trait, is most widely used in the hybrid industry to render the male properties of a plant nonfunctional. During fertilization the female contributes a haploid nucleus and virtually all of the cytoplasm from the egg, while the male contributes a haploid nucleus but almost no cytoplasm from the pollen. The result being that the female cytoplasm which confers male sterility is passed from generation to generation. Information carried in the cytoplasm affecting the phenotype, i.e., anther presence or pollen production is contributed exclusively by the female. This type of sterility affects only pollen production; seed set is normal. Generally, all the progeny from a male sterile plant are themselves male sterile. However, in some cases male fertility can be restored. Pearson, O. H. (1981) Hort Sci. 16: 482-487. Fertility can be restored either by cytoplasmic reversion to fertility or by a nuclear restorer gene able to override the effects of cytoplasm. MacKenzie, S. A. et al. (1988) Proc. Natl. Acad. Sci. USA J35: 2714-2717. A specific cytoplasm can be carried along from generation to generation provided the plant possessing the cytoplasm is the maternal parent in each cross.

Typically, upon identification of a source of cytoplasmic male sterility, the "rf" trait is transferred to a desirable "female" or "A" line. A "maintenance" or "B" line lacking both the sterility trait and restoration factor is used to perpetuate and increase the female line. A "restorer" or "Rf" line, carrying a pollen fertility factor is used as a male to pollinate the cytoplasmic male sterile "A" line to create a hybrid variety. The cytoplasmic male sterile plant of the "A" line can be crossed with a plant from a different variety to produce hybrid progeny. This type of breeding program is often referred to as a cytoplasmic male sterile-restorer system.

Various Rf alleles have been sequences or cloned, for example, Rf2 from maize (*Zea mays*) (Cui, X., Wise, R. P., and Schnable, P. S. 1996. The Rf2 nuclear restorer gene of male-sterile T-cytoplasm maize. Science 272:1334-1336), Rf-PPR592 from *Petunia* (*Petunia hybrida*) (Bentolila, S., Alfonso, A. A., and Hanson, M. R. 2002. A pentatricopeptide repeat-containing gene restores fertility to male sterile plants. Proc. Natl. Acad. Sci. USA 99:10887-10892), Rfo from radish (*Raphanus sativus*) (Brown, G. G., Formanova, N., Jin, H., Wargachuk, R., Dendy, C., Patil, P., Laforest, M., Zhang, J. F., Cheung, W. Y., and Landry, B. S. 2003. The radish Rf Restorer gene of Ogura cytoplasmic male sterility encodes a protein with multiple pentatricopeptide repeats. Plant J. 35:262-272; Desloire, S., Gherbi, H., Laloui, W., Marhadour, S., Clouet, V., Cattolico, L., Falentin, C., Giancola, S., Renard, M., Burdar, F., Small, I., Caboche, M., and Bendahmane, A. 2003. Identification of the fertility restorer locus, Rfo, in radish, as a member of the pentatricopeptide-repeat protein family. EMBO Rep. 4:1-7; Koizuka, N., Imai, R., Fujimoto, H., Hayakawa, T., Kimura, Y., Kohno-Murase, J., Sakai, T., Kawasaki, S., Imamura, J. 2003. genetic characterization of a pentatricopeptide repeat protein gene, orf687, that restores fertility in the cytoplasmic male sterile Kosena radish. Plant J. 34:407-415), Rf1 and Rf2 from sorghum (*Sorghum bicolor*) (Klein, R. R., Klein, P. E., Mullet, J. E., Minx, P., Rooney, W. L., and Schertz, K. F. 2005. Fertility restorer locus Rf1 of sorghum (*Sorghum bicolor* L.) encodes a pentatricopeptide repeat protein not present in the collinear region of rice chromosome 12. Theor. A. 1. Genet. 111:994-1012), Rf1a and Rf1b from rice (*Oryza sativa*) for BT-type CMS (Kazama, T., and Toriyama, K. 2003. A pentatricopeptide repeat-containing gene that promotes the processing of aberrant atp6 RNA of cytoplasmic male-sterile rice. FEBS Lett. 544:99-102; Akagi, H., Nakamura, A., Yokozeki-Misono, Y., Inagaki, A., Takahashi, H., Mori, K., and Fujimura, T. 2004. Position cloning of the rice Rf-1 gene, a restorer of BT-type cytoplasmic male sterility that encodes a mitochondria-targeting PPR protein. Theor. Appl. Genet. 108:1449-1457; Komori, T., Ohta, /s., Murai, N., Takakura, Y., Kuraya, Y., Suzuki, S., Hiei, Y., Imaseki, H., and Nitta, N. 2004. Map-based cloning of a fertility restorer gene, Rf-1 in rice (*Oryza sativa* L.). Plant J. 37:315-325; and, Wang, Z., Zou, Y., Li, X., Zhang, Q., Chen, L., Wu, H., Su, D., Chen, Y., Guo, J., Luo, D., Long, Y., Zhong, Y., and Liu, Y. G. 2006b. Cytoplasmic male sterility of rice with Boro II cytoplasm is caused by a cytotoxic peptide and is restored by two related PPR motif genes via distinct modes of mRNA silencing. Plant Cell 18:676-687), Rf17 (RMS) from rice (*Oryza sativa*) for CW-type CMS (Fujii S. & Toriyama K. 2009. Suppressed expression of RETROGRADE-REGULATED MALE STERILITY restores pollen fertility in cytoplasmic male sterile rice plants. PNAS 106:9513-9518), Rf1 & Rf2 from monkey flower (*Mimulus guttatus*) (Barr, C. M., & Fishman L. 2010. The Nuclear component of a cytonuclear hybrid incompatibility in *Mimulus* maps to a cluster of pentatricopeptide repeat genes. Genetics 184:455-465), Rf2 for Lead Rice-type CMS from rice (*Oryza sativa*) (Itabashi, E., Iwata, N., Fujii, S., Kazama, T. and Toriyama, K. 2011. The Fertility restorer gene, Rf2 for lead Rice-type cytoplasmic male sterility of rice encodes a mitochondrial glycine-rich protein. The plant Journal (2011) 65:359-367), Rf5 for Hong-Lian CMS from rice (*Oryza sativa*) (Hu, J., Wang, K., Huang, W., Liu, G., Wang, J., Huang, Q., Ji, Y., Qin, X., Wan, L., Zhu, R., Li, S., Yang, D. and Zhu, Y. 2012. The Rice Pentatricopeptide Repeat Protein Rf5 Restores Fertility in Hong-Lian Cytoplasmic Male-Sterile Lines via a Complex with the Glycine-Rich Protein GRP162. The plant cell advance online publication 2012), and Rf4 for CMS C-type of maize (*Zea mays*) (U.S. Patent Pub. No. 2012/0090047 A1).

In other embodiments the isolated polypeptide of SEQ ID NO:1 further comprises an amino acid sequence with at least 85%, 87.5%, 90%, 92.5%, 95%, 97.5%, or 99% sequence identity to SEQ ID NO:3. In a subsequent embodiment, the isolated polypeptide of SEQ ID NO:1 and a polypeptide with 85%, 87.5%, 90%, 92.5%, 95%, 97.5% or 99% sequence identity to SEQ ID NO:3 have cytoplasmic male sterile activity.

The term "percent identity" (or "% identity"), as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those disclosed in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. See Russell, R., and Barton, G., "Structural Features can be Unconserved in Proteins with Similar Folds," J. Mol. Biol. 244, 332-350 (1994), at p. 337, which is incorporated herein by reference in its entirety.

In addition, methods to determine identity and similarity are codified in publicly available computer programs. Sequence alignments and percent identity calculations can be performed, for example, using the AlignX program of the Vector NTI® suite (Invitrogen, Carlsbad, Calif.) or MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (disclosed by Higgins and Sharp, *CABIOS.* 5:151-153 (1989); Higgins, D. G. et al., *Comput. Appl. Biosci.,* 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191(1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 55%, 60%, 65%, 70%, 75%, 80%, 85%, 90%, or 95%, or any integer percentage from 55% to 100% may be useful in describing embodiments of the present disclosure, such as 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

When referring to hybridization techniques, all or part of a known nucleotide sequence can be used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, plasmid DNA fragments, cDNA fragments, RNA fragments, PCR amplified DNA fragments, oligonucleotides, or other polynucleotides, and may be labeled with a detectable group such as $^{32}$P, or any other detectable marker. Thus, for example, probes for hybridization can be made by labeling synthetic oligonucleotides based on the DNA sequences of embodiments of the disclosure. Methods for preparation of probes for hybridization and for construction of cDNA and genomic libraries are generally known in the art and are disclosed (Sambrook et al., 1989).

The nucleic acid probes and primers of embodiments of the present disclosure hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if the two nucleic acid molecules exhibit complete complementarity. As used herein, molecules are said to exhibit "complete complementarity" when every nucleotide of one of the molecules is complementary to a nucleotide of the other. Molecules that exhibit complete complementarity will generally hybridize to one another with sufficient stability to permit them to remain annealed to one another under conventional "high-stringency" conditions. Conventional high-stringency conditions are described by Sambrook et al., 1989.

Two molecules are said to exhibit "minimal complementarity" if they can hybridize to one another with sufficient stability to permit them to remain annealed to one another under at least conventional "low-stringency" conditions. Conventional low-stringency conditions are described by Sambrook et al., 1989. In order for a nucleic acid molecule to serve as a primer or probe, it need only exhibit the minimal complementarity of sequence to be able to form a stable double-stranded structure under the particular solvent and salt concentrations employed.

Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

The term "stringent condition" or "stringency conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58.

Typically, stringent conditions will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1.0 M NaCl, 0.1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 0.1% SDS at 37° C., and a wash in 0.5× to 1×SSC at 55 to 60° C. Exemplary high stringency conditions include hybridization in 50% formamide, 1.0 M NaCl, 0.1% SDS at 37° C., and a wash in 0.1×SSC at 60 to 65° C.

Specificity is typically a function of post-hybridization washes, the critical factors being the ionic strength and temperature of the final wash solution. For DNA-DNA hybrids, the $T_m$ can be approximated from the equation $T_m = 81.5°$ C. $+ 16.6$ (log M) $+ 0.41$(% GC) $- 0.61$(% form.) $- 500/L$, where M is the molarity of monovalent cations, % GC is the percentage of guanosine and cytosine nucleotides in the DNA, % form. is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found (1997) Ausubel et al, *Short Protocols in Molecular Biology*, pages 2-40, Third Edit. (1997) and Sambrook et al. (1989).

In other embodiments, the subject disclosure provides a cell comprising the polypeptide of SEQ ID NO:1 or SEQ ID NO:3. The term "cell" as referred to herein encompasses a living organism capable of self replication, and may be a eukaryotic or prokaryotic cell. In some embodiments the cell is a plant cell. In some embodiments, the plant cell can be but is not limited to any higher plant, including both dicotyledonous and monocotyledonous plants, and consumable plants, including crop plants and plants used for their oils. Thus, any plant species or plant cell can be selected as described further below.

In some embodiments, plant cells in accordance with the present disclosure includes, but is not limited to, any higher plants, including both dicotyledonous and monocotyledonous plants, and particularly consumable plants, including crop plants. Such plants can include, but are not limited to, for example: alfalfa, soybeans, cotton, rapeseed (also described as canola), linseed, corn, rice, *brachiaria*, wheat, safflowers, *sorghum*, sugarbeet, sunflowers, tobacco and turf grasses. Thus, any plant species or plant cell can be selected. In embodiments, plant cells used herein, and plants grown or derived therefrom, include, but are not limited to, cells obtainable from rapeseed (*Brassica napus*); indian mustard (*Brassica juncea*); Ethiopian mustard (*Brassica carinata*); turnip (*Brassica rapa*); cabbage (*Brassica oleracea*); soybean (*Glycine max*); linseed/flax (*Linum usitatissimum*); maize (also described as corn) (*Zea mays*); safflower (*Carthamus tinctorius*); sunflower (*Helianthus annuus*); tobacco (*Nicotiana tabacum*); *Arabidopsis thaliana*; Brazil nut (*Betholettia excelsa*); castor bean (*Ricinus communis*); coconut (*Cocus nucifera*); coriander (*Coriandrum sativum*); cotton (*Gossypium* spp.); groundnut (*Arachis hypogaea*); jojoba (*Simmondsia chinensis*); oil palm (*Elaeis guineeis*); olive (*Olea eurpaea*); rice (*Oryza sativa*); squash (*Cucurbita maxima*); barley (*Hordeum vulgare*); sugarcane (*Saccharum officinarum*); rice (*Oryza sativa*); wheat (*Triticum* spp. including *Triticum durum* and *Triticum aestivum*); and duckweed (*Lemnaceae* sp.). In some embodiments, the genetic background within a plant species may vary.

In a further embodiment, the subject disclosure provides a seed comprising the polypeptide of SEQ ID NO:1 or SEQ ID NO:3. In subsequent embodiments a seed from maize is provided. A maize seed may be described or referred to as a kernel, and is composed of four structural parts: (1) the pericarp, which is a protective outer covering (also known as bran or hull); (2) the germ (also known as an embryo); (3) the endosperm; and, (4) the tip cap, which is the point of attachment to the cob. Another aspect of the present disclosure is one or more parts of corn seed, such as the pericarp of the corn seed or the germ and/or the endosperm of the corn seed which remain upon removal of the pericarp and adhering remnants of the seed coat.

The subject disclosure also relates to one or more corn plant parts of an rf3 or Rf3 corn line. Corn plant parts include plant cells, plant protoplasts, plant cell tissue cultures from which corn plants can be regenerated, plant DNA, plant calli, plant clumps, and plant cells that are intact in plants or parts of plants, such as embryos, pollen, ovules, flowers, seeds, kernels, ears, cobs, leaves, husks, stalks, roots, root tips, brace roots, lateral tassel branches, anthers, tassels, glumes, silks, tillers, and the like.

In subsequent embodiments, the subject disclosure relates to a cell comprising SEQ ID NO:5. In other embodiments, the cell is a plant cell. Further embodiments include a plant comprising the plant cell. In some embodiments the plant may be a monocotyledonous or dicotyledonous plant. In other embodiments, the monocotyledonous plant is a maize plant. Further embodiments include a maize plant with CMS-S type cytoplasm. Additional embodiments include a plant part, plant tissue, or plant seed.

V. Polynucleotide Sequences Encoding the Isolated Protein

The subject disclosure further provides a synthetic nucleic acid sequence encoding the polypeptide of SEQ ID NO:1 or SEQ ID NO:3. In an embodiment, the synthetic nucleic acid sequence comprising the polypeptide of SEQ ID NO:1 is encoded by SEQ ID NO:2. In further embodiments, the synthetic nucleic acid sequence comprising the polypeptide of SEQ ID NO:3 is encoded by SEQ ID NO:4. In subsequent embodiments, a sequence with 85%, 87.5%, 90%, 92.5%, 95%, 97.5%, or 99% sequence identify of SEQ ID NO:4 is provided. In other embodiments, a polynucleotide comprising the synthetic nucleic acid sequence of SEQ ID NO:2. In an embodiment, the polynucleotide sequences that comprise the synthetic nucleic acid sequence of SEQ ID NO:2, may include a gene expression cassette, a vector, a plasmid, a bacterial artificial chromosome, a DNA fragment, an oligonucleotide, a primer, or a probe.

In further embodiments, the synthetic nucleic acid sequence of SEQ ID NO:2 is operably linked to a promoter, wherein the promoter is functional in plants. In an aspect of the embodiment, the promoter is a plant cytoplasmic male sterile promoter In an embodiment the synthetic nucleic acid sequence of SEQ ID NO:2 is operably linked to a promoter. The promoter used to direct expression of a peptide encoding nucleic acid depends on the particular application. For example, a number of promoters that direct expression of a gene in a plant can be employed. Such promoters can be selected from constitutive, chemically-regulated, inducible, tissue-specific, and seed-preferred promoters.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods. In some embodiments the synthetic nucleic acid sequence that is operably linked to a promoter may further comprise a coding sequence for a transit peptide. Examples of transit peptides are known in the art and include mitochondrial or chloroplast targeting transit peptides.

Subsequent embodiments of the subject disclosure relate to a cell comprising the synthetic nucleic acid sequence of SEQ ID NO:2. Additional embodiments of the subject disclosure relate to a cell comprising the synthetic nucleic acid sequence of SEQ ID NO:4. Further embodiments of the subject disclosure relate to a vector comprising the synthetic nucleic acid sequence of SEQ ID NO:2. Additional embodiments of the subject disclosure relate to a cell comprising the synthetic nucleic acid sequence of SEQ ID NO:4. In other embodiments the subject disclosure provides a cell comprising any previous embodiment of said vector.

In other embodiments the vector comprises a plasmid. A plasmid or vector can be described or referred to as prokaryotic vectors, shuttle vectors, insect vectors, or eukaryotic vectors. Typically, plasmids are extra-chromosomal elements, often circular DNA, that are comprised of an origin of replication and a selectable marker gene. At times, it may be preferable to have a plasmid that is functional in E. coli (e.g., DNA sequence analysis, construction of inserts, obtaining quantities of nucleic acids). The particular plasmid can be selected with regard to the intended use (e.g., expression in plants, animals, bacteria, fungus, and protozoa). Standard bacterial, plant, and animal expression plasmids are known in the art and are described in detail, for example, U.S. Patent Publication 20050064474A1 and International Patent Publications WO 05/084190, WO05/014791 and WO03/080809. Examples of a plasmid include a pUC19 plasmid. pUC19 is a small double stranded DNA circle. The plasmid contains high copy number origin of replication that is capable of bacterial replication and contains a multiple cloning site. See Yanisch-Perron, C., Vieira, J. and Messing, J. (1985). Gene. 33, 103-119. Other plasmids are known and commonly used in the art. For example, pUC18, pBR322, pBR325, pBR328, pACYC184, pAT153, pUC118, and pUC119 are plasmids commonly known in the art.

In further embodiments of the subject disclosure, an isolated polypeptide comprising an amino acid sequence of SEQ ID NO: 5 is provided. In a further embodiment, the isolated polypeptide of SEQ ID NO:5 further comprises an amino acid sequence with at least 85% sequence identity to SEQ ID NO:7. In a subsequent embodiment, the isolated polypeptide of SEQ ID NO:5 and a polypeptide with 85% sequence identity to SEQ ID NO:7 have cytoplasmic male sterile activity.

The subject disclosure further provides a synthetic nucleic acid sequence encoding the polypeptide of SEQ ID NO:5 or SEQ ID NO:7. In an embodiment, the synthetic nucleic acid sequence comprising the polypeptide of SEQ ID NO:5 is encoded by SEQ ID NO:6. In further embodiments, the synthetic nucleic acid sequence comprising the polypeptide of SEQ ID NO:7 is encoded by SEQ ID NO:8. In subsequent embodiments, a sequence with 85%, 87.5%, 90%, 92.5%, 95%, 97.5%, or 99% sequence identify of SEQ ID NO:8 is provided. In other embodiments, a polynucleotide comprising the synthetic nucleic acid sequence of SEQ ID NO:8. In an embodiment, the polynucleotide sequences that comprise the synthetic nucleic acid sequence of SEQ ID NO:8, may include a gene expression cassette, a vector, a plasmid, a bacterial artificial chromosome, a DNA fragment, an oligonucleotide, a primer, or a probe.

In other embodiments, the subject disclosure relates to a synthetic nucleic acid sequence encoding the polypeptide of SEQ ID NO:5. In further embodiments, the synthetic nucleic acid sequence has the sequence of SEQ ID NO:8. In additional embodiments, a gene expression cassette comprising the synthetic nucleic acid sequence of SEQ ID NO:8 is provided. Further embodiments include the gene expression cassette comprising the synthetic nucleic acid sequence of SEQ ID NO:8 operably linked to a promoter, wherein the promoter is functional in plants. In additional embodiments the promoter is a cytoplasmic male sterile promoter. Additional embodiments include a cell comprising the gene expression cassette comprising the synthetic nucleic acid sequence of SEQ ID NO:8. Further embodiments of the subject disclosure relate to a vector comprising the synthetic nucleic acid sequence of SEQ ID NO:8. In other embodiments the subject disclosure provides a cell comprising said vector.

VI. Introgression of RF3 Alleles into Progeny Plants

An embodiment of the subject disclosure provides a method for producing a progeny cytoplasmic male sterile plant, the method comprising the steps of:
 a) crossing a female parent plant with a male parent plant, wherein the female parent plant is a cytoplasmic male sterile parent plant homozygous for SEQ ID NO:4, and wherein the male parent plant is a fertile parent plant;
 b) harvesting a progeny seed from the cross of (a), wherein the progeny seed is homozygous for SEQ ID NO:4;
 c) planting the progeny seed; and,
 d) growing the progeny seed, wherein the progeny seed produce the progeny cytoplasmic male sterile plant, wherein the progeny cytoplasmic male sterile plant is homozygous for SEQ ID NO:4.

In additional embodiments, the subject disclosure relates to female and male parent plants that are monocotyledonous plants. In other embodiments, the monocotyledonous plants are maize plants. In further embodiments the male parent plant is isogenic to the female parent plant. In an aspect of the embodiment, the male parent plant is homozygous or heterozygous for SEQ ID NO:8.

In yet another aspect of the subject disclosure, processes are provided for producing progeny plants, which processes generally comprise crossing a first parent corn plant with a second parent corn plant wherein at least one of the first parent corn plant or the second parent corn plant is a cytoplasmic male sterile plant having CMS-S type cytoplasm. In some embodiments of the present disclosure, the cytoplasmic male sterile plant is a female and in other embodiments the cytoplasmic male restorer plant is a male. These processes may be further exemplified as processes for producing progeny seed or plants, wherein a first corn plant is crossed with a second corn plant.

Any time the cytoplasmic male sterile plant or the cytoplasmic male restorer plant is crossed with another, different corn inbred, a progeny or first generation ($F_1$) corn hybrid plant is produced. As such, a progeny or $F_1$ hybrid corn plant may be produced by crossing the cytoplasmic male sterile plant or the cytoplasmic male restorer plant with any second inbred corn plant. Therefore, any progeny or $F_1$ hybrid corn plant or corn seed which is produced with the cytoplasmic male sterile plant or the cytoplasmic male restorer plant as a parent is an embodiment of the subject disclosure.

When the cytoplasmic male sterile plant or the cytoplasmic male restorer plant is crossed with another inbred plant to yield a progeny or hybrid, the original parent can serve as either the maternal or paternal plant with basically, the same characteristics in the hybrids. Occasionally, maternally inherited characteristics may express differently depending on the decision of which parent to use as the female. However, often one of the parental plants is preferred as the maternal plant because of increased seed yield and preferred production characteristics, such as optimal seed size and quality or ease of tassel removal. Some plants produce tighter ear husks leading to more loss, for example due to rot, or the ear husk may be so tight that the silk cannot completely push out of the tip preventing complete pollination resulting in lower seed yields. There can be delays in silk formation which deleteriously affect timing of the reproductive cycle for a pair of parental inbreds. Seed coat characteristics can be preferable in one plant which may affect shelf life of the hybrid seed product. Pollen can shed better by one plant, thus rendering that plant as the preferred male parent.

In embodiments of the present disclosure, the first step of "crossing" the cytoplasmic male sterile plant or the cytoplasmic male restorer plant comprises planting, preferably in pollinating proximity, seeds of a first inbred corn plant and a second, distinct inbred corn plant.

A further step comprises cultivating or growing the seeds of the cytoplasmic male sterile plant or the cytoplasmic male restorer plant that bear flowers. If the parental plants differ in timing of sexual maturity, techniques may be employed to obtain an appropriate nick, i.e., to ensure the availability of pollen from the parent corn plant designated the male during the time at which silks on the parent corn plant designated the female are receptive to the pollen. Methods that may be employed to obtain the desired nick include delaying the flowering of the faster maturing plant, such as, but not limited to delaying the planting of the faster maturing seed, cutting or burning the top leaves of the faster maturing plant (without killing the plant) or speeding up the flowering of the slower maturing plant, such as by covering the slower maturing plant with film designed to speed germination and growth or by cutting the tip of a young ear shoot to expose silk.

In an embodiment, the male sterile plant or the cytoplasmic male restorer plant are treated with one or more agricultural chemicals as considered appropriate by the grower.

A further step comprises harvesting the seeds, near or at maturity, from the ear of the plant that received the pollen. In a particular embodiment, seed is harvested from the female parent plant, and when desired, the harvested seed can be grown to produce a progeny or first generation ($F_1$) hybrid corn plant.

Yet another step comprises drying and conditioning the seeds, including the treating, sizing (or grading) of seeds, and packaging for sale to growers for the production of grain or forage. As with inbred seed, it may be desirable to treat hybrid seeds with compositions that render the seeds and seedlings grown therefrom more hardy when exposed to adverse conditions. Mention should be made that resulting progeny or hybrid seed may be sold to growers for the production of grain and forage and not for breeding or seed production.

Still further, the subject disclosure provides a progeny corn plant produced by growing the harvested seeds produced on the cytoplasmic male-sterile or restorer plant as well as grain produced by the progeny corn plant.

In a subsequent embodiment, the disclosure related to introducing a desired trait into the progeny cytoplasmic male sterile plant. In an aspect of the embodiment, the desired trait is selected from the group consisting of an insecticidal resistance trait, herbicide tolerant trait, disease resistance trait, yield increase trait, nutritional quality trait, agronomic increase trait, and combinations thereof. Other examples of a desired trait include modified fatty acid metabolism, for example, by transforming a plant with an antisense gene of stearoyl-ACP desaturase to increase stearic acid content of the plant. See Knultzon et al., Proc. Natl. Acad. Sci. USA 89: 2624 (1992). Decreased phytate content: (i) Introduction of a phytase-encoding gene would enhance breakdown of phytate, adding more free phosphate to the transformed plant. For example, see Van Hartingsveldt et al., Gene 127: 87 (1993), for a disclosure of the nucleotide sequence of an *Aspergillus niger* phytase gene. (ii) A gene could be introduced that reduces phytate content. In corn, this, for example, could be accomplished, by cloning and then reintroducing DNA associated with the single allele which is responsible for corn mutants characterized by low levels of phytic acid. See Raboy et al., Maydica 35: 383 (1990). (iii) Modified carbohydrate composition effected, for example, by transforming plants with a gene coding for an enzyme that alters the branching pattern of starch. See Shiroza et al., J. Bacteriol. 170: 810 (1988) (nucleotide sequence of *Streptococcus mutans* fructosyltransferase gene), Steinmetz et al., Mol. Gen. Genet. 200: 220 (1985) (nucleotide sequence of *Bacillus subtillus* levansucrase gene), Pen et al., Bio/Technology 10: 292 (1992) (production of transgenic plants that express *Bacillus licheniformis* α-amylase), Elliot et al., Plant Molec. Biol. 21: 515 (1993) (nucleotide sequences of tomato invertase genes), Sogaard et al., J. Biol. Chem. 268: 22480 (1993) (site-directed mutagenesis of barley α-amylase gene), and Fisher et al., Plant Physiol. 102: 1045 (1993) (corn endosperm starch branching enzyme II). Further examples of potentially desired characteristics include greater yield, better stalks, better roots, reduced time to crop maturity, better agronomic quality, higher nutritional value, higher starch extractability or starch fermentability, resistance and/or tolerance to insecticides, herbicides, pests, heat and drought, and disease, and uniformity in germination times, stand establishment, growth rate, maturity and kernel size.

In an additional embodiment, the subject disclosure relates to a method for producing a progeny cytoplasmic male sterile plant, the method further comprising the steps of:

e) crossing the progeny cytoplasmic male sterile plant, with another plant comprising a desired trait to produce F1 progeny plants;
f) selecting F1 progeny plants that have the desired trait to produce selected F1 progeny plants;
g) crossing the selected F1 progeny plants with the progeny cytoplasmic male sterile plant to produce backcross progeny plants;
h) selecting for backcross progeny plants that have the desired trait; and,
i) repeating steps (g) and (h) three or more times in succession to produce selected fourth or higher backcross progeny plants that comprise the desired trait.

Various breeding schemes may be used to produce progeny plants. In one method, generally referred to as the pedigree method, the parent may be crossed with another different plant such as a second inbred parent corn plant, which either itself exhibits one or more selected desirable characteristic(s) or imparts selected desirable characteristic(s) to a hybrid combination. If the two original parent corn plants do not provide all the desired characteristics, then other sources can be included in the breeding population. Progeny plants, that is, pure breeding, homozygous inbred lines, can also be used as starting materials for breeding or source populations from which to develop progeny plants.

Thereafter, resulting seed is harvested and resulting superior progeny plants are selected and selfed or sib-mated in succeeding generations, such as for about 5 to about 7 or more generations, until a generation is produced that no longer segregates for substantially all factors for which the inbred parents differ, thereby providing a large number of distinct, pure-breeding inbred lines.

In another embodiment for generating progeny plants, generally referred to as backcrossing, one or more desired traits may be introduced into the cytoplasmic male sterile parent or restored fertile parent by crossing the parent plants with another corn plant (referred to as the donor or non-recurrent parent) which carries the gene(s) encoding the particular trait(s) of interest to produce $F_1$ progeny plants. Both dominant and recessive alleles may be transferred by backcrossing. The donor plant may also be an inbred, but in the broadest sense can be a member of any plant variety or population cross-fertile with the recurrent parent. Next, $F_1$ progeny plants that have the desired trait are selected. Then, the selected progeny plants are crossed with the cytoplasmic male sterile parent or restored fertile parent to produce backcross progeny plants. Thereafter, backcross progeny plants comprising the desired trait and the physiological and morphological characteristics of the cytoplasmic male sterile parent or restored fertile parent are selected. This cycle is repeated for about one to about eight cycles, preferably for about 3 or more times in succession to produce selected higher backcross progeny plants that comprise the desired trait and all of the physiological and morphological characteristics of the cytoplasmic male sterile parent or restored fertile parent when grown in the same environmental conditions. Exemplary desired trait(s) include insect resistance, enhanced nutritional quality, waxy starch, herbicide resistance, yield stability, yield enhancement and resistance to bacterial, fungal and viral disease. One of ordinary skill in the art of plant breeding would appreciate that a breeder uses various methods to help determine which plants should be selected from the segregating populations and ultimately which inbred lines will be used to develop hybrids for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which inbred lines and hybrid combinations are significantly better or different for one or more traits of interest. Experimental design methods are used to assess error so that differences between two inbred lines or two hybrid lines can be more accurately determined. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding would know how to evaluate the traits of two plant varieties to determine if there is no significant difference between the two traits expressed by those varieties. For example, see Fehr, Walt, Principles of Cultivar Development, p. 261-286 (1987) which is incorporated herein by reference. Mean trait values may be used to determine whether trait differences are significant, and preferably the traits are measured on plants grown under the same environmental conditions.

This method results in the generation of progeny inbred plants with substantially all of the desired morphological and physiological characteristics of the recurrent parent and the particular transferred trait(s) of interest. Because such progeny inbred plants are heterozygous for loci controlling the transferred trait(s) of interest, the last backcross generation would subsequently be selfed to provide pure breeding progeny for the transferred trait(s).

Backcrossing may be accelerated by the use of genetic markers such as SSR, RFLP, SNP or AFLP markers to identify plants with the greatest genetic complement from the recurrent parent.

Direct selection may be applied where a single locus acts as a dominant trait, such as the herbicide resistance trait. For this selection process, the progeny of the initial cross are sprayed with the herbicide before the backcrossing. The spraying eliminates any plants which do not have the desired herbicide resistance characteristic, and only those plants which have the herbicide resistance gene are used in the subsequent backcross. In the instance where the characteristic being transferred is a recessive allele, it may be necessary to introduce a test of the progeny to determine if the desired characteristic has been successfully transferred. The process of selection, whether direct or indirect, is then repeated for all additional backcross generations.

It should be appreciated by those having ordinary skill in the art that backcrossing can be combined with pedigree breeding as where the cytoplasmic male sterile parent or restored fertile parent is crossed with another corn plant, the resultant progeny are crossed back to the cytoplasmic male sterile parent or restored fertile parent and thereafter, the resulting progeny of this single backcross are subsequently inbred to develop new inbred lines. This combination of backcros sing and pedigree breeding is useful as when recovery of fewer than all of the cytoplasmic male sterile parent or restored fertile parent characteristics than would be obtained by a conventional backcross are desired.

In an additional embodiment, the subject disclosure relates to a method for restoring fertility to a progeny of a cytoplasmic male sterile parent plant, the method comprising:
a) crossing a female parent plant with a male parent plant, wherein the female parent plant is a cytoplasmic male sterile parent plant homozygous or heterozygous for SEQ ID NO:8, and wherein the cytoplasmic male sterile plant is a fertile parent plant;

b) harvesting a progeny seed from the cross of (a), wherein the progeny seed is homozygous or heterozygous for SEQ ID NO:8;

c) planting the progeny seed;

d) growing the progeny seed, wherein the progeny seed produce a progeny cytoplasmic male fertile plant; and, e) restoring fertility to the progeny of the cytoplasmic male sterile parent plant, wherein the progeny cytoplasmic male fertile plant is homozygous or heterozygous for SEQ ID NO:8.

Additional embodiments to the method include.

f) crossing the progeny cytoplasmic male sterile plant, with another plant comprising a desired trait to produce F1 progeny plants;

g) selecting F1 progeny plants that have the desired trait to produce selected F1 progeny plants;

h) crossing the selected F1 progeny plants with progeny cytoplasmic male sterile plant to produce backcross progeny plants;

i) selecting for backcross progeny plants that have the desired trait; and, j) repeating steps (h) and (i) three or more times in succession to produce selected fourth or higher backcross progeny plants that comprise the desired trait.

In additional embodiments, the subject disclosure relates to female and male parent plants that are monocotyledonous plants. In other embodiments, the monocotyledonous plants are maize plants. In further embodiments the male parent plant is isogenic to the female parent plant. In an aspect of the embodiment, the male parent plant is homozygous or heterozygous for SEQ ID NO:8. In a subsequent embodiment, the disclosure related to introducing a desired trait into the progeny cytoplasmic male sterile plant. In an aspect of the embodiment, the desired trait is selected from the group consisting of an insecticidal resistance trait, herbicide tolerant trait, disease resistance trait, yield increase trait, nutritional quality trait, agronomic increase trait, and combinations thereof.

VII. Assays for Detection of the Rf3 and Rf3 Alleles

Various assays can be employed to detect the polynucleotides that encode the Rf3 and rf3 alleles that are described in certain embodiments of the disclosure. The following techniques are useful in a variety of situations, and in one embodiment, are useful in detecting the presence of a nucleic acid molecule and/or the polypeptide encoding an Rf3 or rf3 allele in a plant cell. For example, the presence of the molecule can be determined in a variety of ways, including using a primer or probe of the sequence, ELISA assay to detect the encoded protein, a Western blot to detect the protein, or a Northern or Southern blot to detect RNA or DNA. Enzymatic assays for detecting the polynucleotides that encode the Rf3 and rf3 allele can be employed. Further, an antibody which can detect the presence of the Rf3 or rf3 protein can be generated using art recognized procedures. Additional techniques, such as in situ hybridization, enzyme staining, and immunostaining, also may be used to detect the presence or expression of the polynucleotides that encode the Rf3 and rf3 alleles in specific plant organs and tissues. The polynucleotides that encode the Rf3 and rf3 alleles may be selectively expressed in some tissues of the plant or at some developmental stages, or the polynucleotides that encode the Rf3 and rf3 alleles may be expressed in substantially all plant tissues, substantially along its entire life cycle. However, any combinatorial expression mode is also applicable.

In an embodiment the disclosure relates method of detecting a plant comprising a cytoplasmic male sterile restorer trait via an amplification reaction in which an amplified product or amplicon is generated. The detection of the absence of the amplicon is an indication of whether the plant contains an Rf3 or rf3 allele of gene sequence, respectively.

Various assays can be employed in connection with the amplification reaction and are considered as embodiments of the disclosure. The following techniques are useful in a variety of situations, and in one embodiment, are useful in detecting the presence of the nucleic acid molecule and/or the polypeptide encoded in a plant cell. For example, the presence of the molecule can be determined in a variety of ways, including using a primer or probe of the sequence. The Rf3 or rf3 alleles may be selectively expressed in some tissues of the plant or at some developmental stages, or the Rf3 or rf3 alleles may be expressed in substantially all plant tissues, throughout the entire life cycle of the plant. However, any combinatorial expression mode is also applicable.

Amplification of a nucleic acid sequence may be carried out by any suitable means. See generally, Kwoh et al., Am. Biotechnol. Lab. 8, 14-25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392-396 (1992); G. Walker et al., Nucleic Acids Res. 20, 1691-1696 (1992)), transcription-based amplification (see D. Kwoh et al., Proc. Natl. Acad Sci. USA 86, 1173-1177 (1989)), self-sustained sequence replication (or "3SR") (see J. Guatelli et al., Proc. Natl. Acad. Sci. USA 87, 1874-1878 (1990)), the Qβ replicase system (see P. Lizardi et al., BioTechnology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra). Polymerase chain reaction is generally preferred.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques were designed primarily for this sorting out.

As used herein, the term "polymerase chain reaction" and "PCR" generally refers to the method for increasing the concentration of a segment of a target sequence in a mixture of genomic DNA without cloning or purification (U.S. Pat. Nos. 4,683,195; 4,683,202; and 4,965,188; herein incorporated by reference). This process for amplifying the target sequence comprises introducing an excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule.

Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified.

The term "plurality" is used herein to mean two or more, for example, three, four, five or more, including ten, twenty, fifty or more polynucleotides, nucleic acid probes, and the like.

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

In an embodiment, the amplification reaction is quantified. In other embodiments, the amplification reaction is quantitated using a signature profile, in which the signature profile is selected from the group consisting of a melting temperature or a fluorescence signature profile. In further embodiments the amplification reaction is quantitated the Delta Delta ct method.

The polynucleotides that encode the Rf3 and rf3 genes, or segments thereof, can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject disclosure. Mutations, insertions, and deletions can be produced in a given primer by methods known to an ordinarily skilled artisan.

Another example of method detection is the pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension (this technique is used for initial sequencing, not for detection of a specific gene when it is known).

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization.

Hydrolysis probe assay, otherwise known as Taqman® (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

The ELISA or enzyme linked immunoassay has been known since 1971. In general, antigens solubilised in a buffer are coated on a plastic surface. When serum is added, antibodies can attach to the antigen on the solid phase. The presence or absence of these antibodies can be demonstrated when conjugated to an enzyme. Adding the appropriate substrate will detect the amount of bound conjugate which can be quantified. A common ELISA assay is one which uses biotinylated anti-(protein) polyclonal antibodies and an alkaline phosphatase conjugate. For example, an ELISA used for quantitative determination of laccase levels can be an antibody sandwich assay, which utilizes polyclonal rabbit antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate.

KASPar® assays are a method of detecting and quantifying the presence of a DNA sequence. Briefly, the genomic DNA sample comprising the targeted genomic locus is screened using a polymerase chain reaction (PCR) based assay known as a KASPar® assay system. The KASPar® assay used in the practice of the subject disclosure can utilize a KASPar® PCR assay mixture which contains multiple primers. The primers used in the PCR assay mixture can comprise at least one forward primers and at least one reverse primer. The forward primer contains a sequence corresponding to a specific region of the DNA polynucleotide sequence, and the reverse primer contains a sequence corresponding to a specific region of a second DNA polynucleotide sequence. In addition, the primers used in the PCR assay mixture can comprise at least one forward primers and at least one reverse primer. For example, the KASPar® PCR assay mixture can use two forward primers corresponding to two different alleles and one reverse primer. One of the forward primers contains a sequence corresponding to specific region of the endogenous genomic sequence. The second forward primer contains a sequence corresponding to a specific region of the donor DNA polynucleotide. The reverse primer contains a sequence corresponding to a specific region of the genomic sequence. Such a KASPar® assay for detection of an amplification reaction is an embodiment of the subject disclosure.

In some embodiments the fluorescent signal or fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

In other embodiments the quencher is selected from the group consisting of a Dabcyl quencher, a Tamra quencher, a Qxl quencher, an Iowa Black FQ quencher, an Iowa Black RQ quencher, an IR Dye QC-1 quencher, a MGB quencher, or a Blackhole quencher.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX Green®, SYBR Green I®, SYTO11®, SYTO12®, SYTO13®, BOBO®, YOYO®, and TOTO®. in one embodiment, a second fluorescent DNA dye is SYTO13® used at less than 10 µM, less than 4 µM, or less than 2.7 µM.

In various embodiments, other known detection methods are performed to detect the Rf3 or rf3 alleles.

Southern analysis is a commonly used detection method, wherein DNA is cut with restriction endonucleases and fractionated on an agarose gel to separate the DNA by molecular weight and then transferring to nylon membranes. It is then hybridized with the probe fragment which was radioactively labeled with 32P (or other probe labels) and washed in an SDS solution.

Likewise, Northern analysis deploys a similar protocol, wherein RNA is cut with restriction endonucleases and fractionated on an agarose gel to separate the RNA by molecular weight and then transferring to nylon membranes. It is then hybridized with the probe fragment which was radioactively labeled with 32P (or other probe labels) and washed in an SDS solution. Analysis of the RNA (e.g., mRNA) isolated from the tissues of interest can indicate relative expression levels. Typically, if the mRNA is present or the amount of mRNA has increased, it can be assumed that the corresponding transgene is being expressed. Northern analysis, or other mRNA analytical protocols, can be used to determine expression levels of an introduced transgene or native gene.

In the Western analysis, instead of isolating DNA/RNA, the protein of interest is extracted and placed on an acrylamide gel. The protein is then blotted onto a membrane and contacted with a labeling substance. See e.g., Hood et al., "Commercial Production of Avidin from Transgenic Maize; Characterization of Transformants, Production, Processing, Extraction and Purification" Molecular Breeding 3:291-306 (1997); Towbin et al, (1979) "Electrophoretic transfer of proteins from polyacrylamide gels to nitrocellulose sheets: procedure and some applications" Proc Natl Acad Sci USA 76(9): 4350-4354; Renart et al. "Transfer of proteins from gels to diazobenzyloxymethyl-paper and detection with antisera: a method for studying antibody specificity and antigen structure" Proc Natl Acad Sci USA 76(7): 3116-3120.

Embodiments of the subject disclosure are further exemplified in the following Examples. It should be understood that these Examples are given by way of illustration only. From the above embodiments and the following Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims. The following is provided by way of illustration and not intended to limit the scope of the invention.

EXAMPLES

Example 1: Development of a Backcross 1 Population for Mapping and Fine Resolution of the Rf3 Alleles A backcross 1 (BC1) population was produced and utilized via linkage map analysis with developed molecular markers to map the Rf3 coding sequence. The mapping population was created by crossing a maize cytoplasmic male sterile line, *Zea mays* c.v. 4XP811 (U.S. Pat. No. 7,135,629; that contained homozygous recessive rf3 alleles) with a maize restoring line *Zea mays* c.v. MBB56 (that contained at least one dominant Rf3 allele), and then backcrossing progeny with the maize cytoplasmic male sterile line, *Zea mays* c.v. 4XP811. The resultant population of maize progeny contained 275 individuals with varying degrees of zygosity for the Rf3 (dominant) and rf3 (recessive) alleles.

Resulting maize plants were phenotypically classified according to two methods. The first method involved observation of the shedding pollen from the maize plants in the field. Fertile plants were observed for the growth and development of anthers that were physically exposed before silk development and the start of pollen shedding. Cytoplasmic male sterile plants were observed for delayed growth and development of anthers. By the middle of silk development (e.g., around 7 days after the silks begin to develop) the anthers were not physically exposed.

The second method involved determination of the vitality of pollen grain by using 1% KI-I$_2$ stain. When the pollen of fertile plants was stained with a KI-I$_2$ stain, the pollen absorbed the KI-I$_2$ stain thereby resulting in uniformly stained pollen. It is well known that the pollen from fertile plants is filled with starch to which the KI-I$_2$ stain adheres. When the pollen from cytoplasmic male sterile plants was stained, the pollen did not absorb the KI-I$_2$ stain thereby resulting in unstained pollen. The pollen of the cytoplasmic male sterile plants contain collapsed pollen that contains low levels of starch, and the KI-I$_2$ stain cannot bind to the minimal amounts of starch present in the pollen. Table 1 provides the detailed segregation information from the BC1 mapping population.

TABLE 1

Phenotype data of the BC1 mapping population.

| BC1 Population | Fertile (heterozygous) restorer plants | Sterile (homozygous recessive, rf3/rf3) cytoplasmic male sterile plants | Broken plants |
|---|---|---|---|
| 4XP811 × BMM56 | 139 | 120 | 16 |

The resulting data indicated that fertility segregation of the BC1 population fit a theoretical 1:1 ratio of fertile plants:sterile plants using the one-gene segregation model ($X^2$=1.39 [a (0.05)=3.84]). The data further suggested that the germplasm of the MBB56 line carried one restorer gene, Rf3, and the germplasm of the 4XP811 was homozygous for the rf3 gene.

Example 2: Marker Assisted Genome Mapping of RF3

Figure 1B:
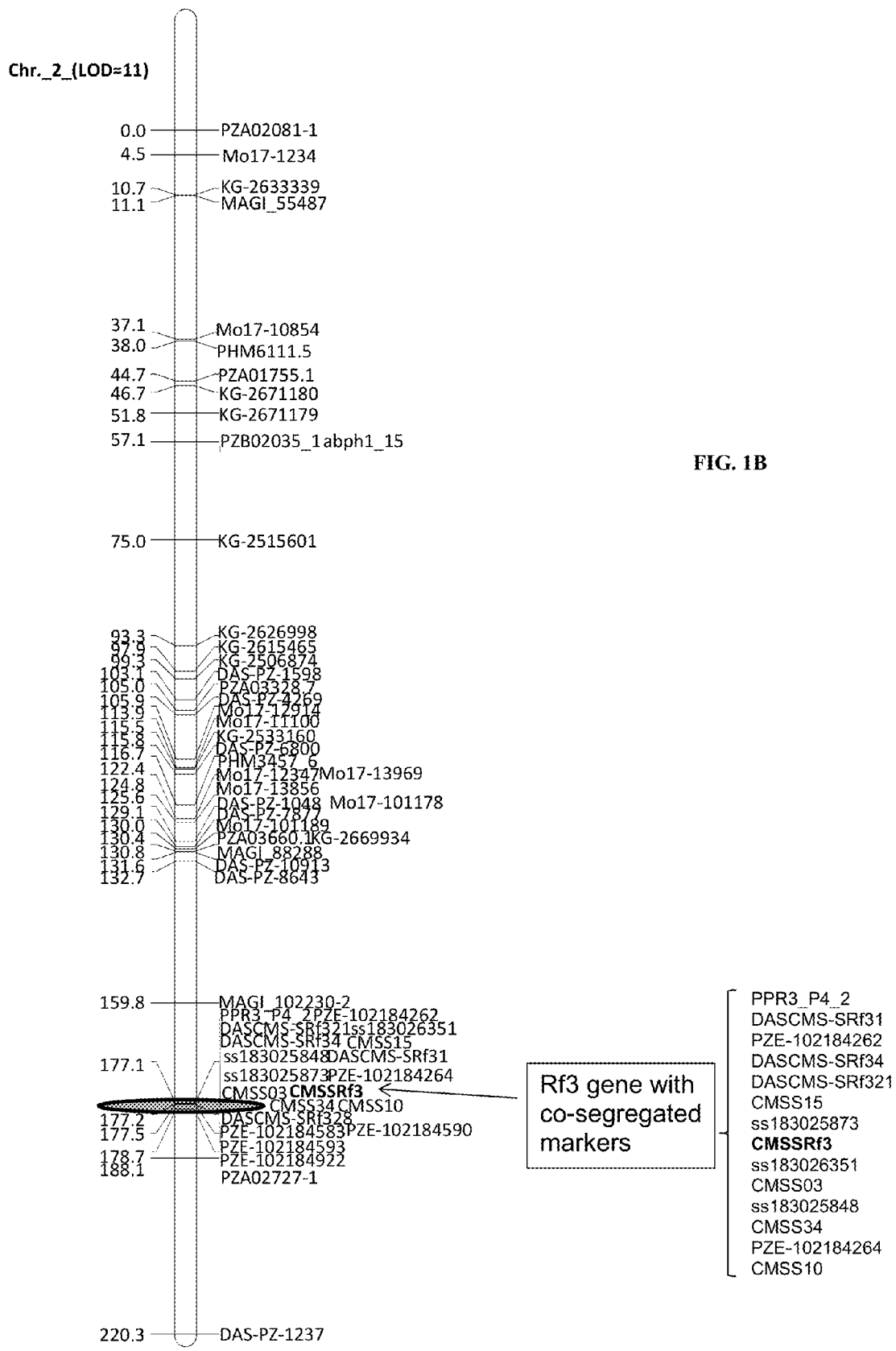

The BC1 populations were screened with molecular markers to identify the locus corresponding with the RF3 allele to high resolution. A panel of 482 SNP markers (evenly distributed on the whole genome) was selected to genotype the BC1 mapping population. From this assay, 437 SNP markers (including four PCR-based markers from PPR2, 432 SNP based markers from across the genome, and one marker based on sterile-fertile phenotype of the BC1 mapping population) were used to create a genetic linkage with JoinMap 4.0 Software™ (Van Ooijen J W: *JoinMap 4. Software for the calculation of genetic linkage maps in experimental populations Kyazma BV*. Netherlands: Wageningen; 2006). Utilizing the genetic linkage map, the phenotypic data, and the genotypic data, a whole genome QTL analysis was performed using Map QTL 6.0™ software (Van Ooijen J W: *Map QTL 6*. Wageningen, Netherlands: Software for the mapping of quantitative trait loci in experimental populations of diploid species Kyazma BV; 2009). The results showed that all the PPR2 gene specific markers co-segregated with the RF3 locus. The genomic location of RF3 locus was determined to lie on chromosome 2 in a 1.3 Mb genomic interval of the corn genome (see FIG. 1B).

Example 3: Whole Genome Sequencing to Identify the RF3 Gene Sequence

To further identify the specific Rf3 restorer gene sequence and the gene sequence of the rf3 modification which results in cytoplasmic male sterility, Next Generation Sequencing (NGS) technology was utilized to further investigate the Rf3 locus. The genomic sequences of two maize CMS-S lines and two maize restorer lines were determined using NGS sequencing. The two CMS-S lines (4XP811 and 7SH382 ms) and the two restorer lines (LH60 and MBB56) were used for whole genome sequencing analysis.

A total of 10 PPR genes (annotated sequentially as PPR 1-10) were identified on chromosome 2 within a 1.3 Mb genomic interval after comparison of the sequenced genomic regions with annotated sequence of the reference genome from *Zea mays* c.v. B73 (available at www.maizegdb.org). A full length coding sequence that corresponds with PPR2 did not exist in the annotated *Zea mays* c.v. B73 genome and could not be predicted as a full length, functional gene. As a result, the full gene sequence for PPR2 was obtained from a sequence comparison to the reference genome of *Zea mays* c.v. Mo17 (available at www.maizegdb.org). The resulting sequences for the 10 PPR genes (PPR2 had two sequences, the first sequence from line *Zea mays* c.v. B73 and the second sequence from line *Zea mays* c.v. Mo17) were assembled for reference sequence information based on whole genome sequencing data of the two CMS-S lines and two restorer lines.

Next, the sequences were aligned between CMS-S lines, restorer lines, and the reference genomic sequences for all of the PPR genes. Coding sequence prediction (e.g., cDNA wherein the intron sequences were removed) of the PPR genomic sequences was completed using Softberry™ software (Softberry Inc., Mount Kisco, N.Y.), and the predicted cDNA and corresponding protein sequences were obtained and aligned. Genomic sequence variations were identified from the aligned genomic sequences of the PPR genes and noted. When the cDNA and the protein sequences were aligned between CMS-S and restorer lines with reference sequences, it was observed that the majority of the variations within the PPR2 sequences resulted in silent mutations (see FIG. 2 and FIG. 3). Variations in the PPR2 sequences that resulted in amino acid residue modifications were identified, and RT-PCR assays were developed to detect and amplify these modifications (e.g., mutations).

The results of the genetic linkage mapping and NGS indicated that the Rf3 allele and the subsequent CMS phenotype was the result of a single gene located on chromosome 2 Like the majority of the cloned Rf genes, Rf3 is most likely a PPR gene. The restorer Rf3-PPR gene from *Zea mays* c.v. LH60 (SEQ ID NO:8) was identified to be present in restorer, fertile plant phenotypes and encodes an 814-amino acid protein (SEQ ID NO: 7). In addition, a partial polynucleotide fragment of the restorer Rf3-PPR gene from *Zea mays* c.v. MBB56 (SEQ ID NO:12) was identified to be present in restorer, fertile plant phenotypes and encodes the amino acid protein fragment (SEQ ID NO: 11). An amino acid motif, SEQ ID NO:5 (IVLFSS), which is encoded by SEQ ID NO:6 (5'-ATTGTTTTATTCAGT-3'), was found to be common for both of the wild type Rf3-PPR genes from *Zea mays* c.v. LH60 and *Zea mays* c.v. MBB56.

The mutated, cytoplasmic male sterile rf3-PPR gene from *Zea mays* c.v. 4XP811 (SEQ ID NO:4) was identified to be present in cytoplasmic male sterile plant phenotypes and encodes an 814-amino acid protein (SEQ ID NO:3). In addition, a cytoplasmic male sterile rf3-PPR gene from *Zea mays* c.v. 7SH382 ms (SEQ ID NO:10) was identified to be present in cytoplasmic male sterile plant phenotypes and encodes an 814-amino acid protein (SEQ ID NO:9). An amino acid motif, SEQ ID NO:1 (IVFFSS), which is encoded by SEQ ID NO:2 (5'-ATTGTTTTCTTCAGT-3'), was found to be common for both of the Rf3-PPR genes from *Zea mays* c.v. 4XP811 and *Zea mays* c.v. 7SH382 ms.

Example 4: Expression Analysis of RF3-PPR2 by Real-Time PCR

To validate whether the expression of the Rf3-PPR2 protein correlated with fertility restoration of S-CMS maize, a real-time PCR (RT-PCR) assay was performed to quantitatively determine the expression pattern of the Rf3-PPR2 gene in fertile plants and the rf3-PPR2 gene in CMS plants. Several specific primer pairs and probes were designed based on portions of the polynucleotide sequences that contained amino acids with variations in the Rf3-PPR2 protein coding gene (Table 2). Total RNA was extracted from the various plant lines. These samples were extracted from two lines; 4XP811 (cytoplasmic male sterile) and LH60 (restorer lines), F3 individuals derived from an F2 ear segregating for the 1.3-Mb region of long arm chromosome 2, and three commercial maize lines. Taqman® assays to quantitate the expression of the Rf3-PPR2 gene were completed. The expression levels were quantitated by comparison to a maize internal control gene, EF α1. (Czechowski T, et al., Plant Physiol., September; 139(1):5-17, 2005).

TABLE 2

Primers and probes used for RT-PCR of the RF3 maize plants.

| Reaction | Primer Name | Primer Sequence | SEQ ID NO: |
|---|---|---|---|
| CMS-S1 | Forward Primer | GATTGATCAAGGAG TAGCACCTGA | 13 |
|  | Reverse Primer | CTTGGCTTTCAGTA AACTACCATGAGT | 14 |
|  | Probe | CATACCATTGCCTG ATTC | 15 |
| CMS-S2 | Forward Primer | GGTAGTTTACTGAA AGCCAAGGAATT | 16 |
|  | Reverse Primer | TTGCAAAGGTTGTT AATTATCGAACT | 17 |
|  | Probe | ATGGCATGCATCTT GACAT | 18 |
| CMS-S3 | Forward Primer | GGGTACTGTCTTGT TGGCAAGAT | 19 |
|  | Reverse Primer | TGGTTCAATGCCAG CTGACA | 20 |
|  | Probe | AGAATGCATTAAGA GTATTTGATGC | 21 |
| CMS-S7 | Forward Primer | GGACAGTGGAAGGA GGCAGTTA | 22 |
|  | Reverse Primer | CCATACTTGCAAAG GGAACCC | 23 |
|  | Probe | CCAGATGTTGTTAC TTTTAACATG | 24 |
| CMS-S8 | Forward Primer | GAATAATGGCATGC GTCTTGATATT | 25 |
|  | Reverse Primer | GTAGGATGCAGACC AACATTTACAGT | 26 |
|  | Probe | CCTTTGCAAATTGG GAAG | 27 |
| RF3 allele specific: CMS-S9 | Forward Primer | GTACTCATGGTAGT TTACTGAAAGCCA | 28 |
|  | Reverse Primer | GCATCCATTACCCT TCCCAAT | 29 |
|  | Probe | ATCTTGACATTGTT TTATTCAGTTCG | 30 |
| CMS-S10 | Forward Primer | GTTCCTGCAAAGGT GAAATTCC | 31 |
|  | Reverse Primer | GAAAGATTGCTTCA TCAAAGCATC | 32 |
|  | Probe | GGTATCGCTATGTA CATATG | 33 |
| Internal Control: Elongation Factor α-1 | Forward Primer | ATAACGTGCCTTGG AGTATTTGG | 34 |
|  | Reverse Primer | TGGAGTGAAGCAGA TGATTTGC | 35 |
|  | Probe | TTGCATCCATCTTG TTGC | 36 |

The plants to be analyzed via the Taqman® assay were grown in a greenhouse. Leaf tissues were collected from 7-week old (just before tasselling) and 10-week old plants (after pollination). Tassel tissues with developing anthers/pollens and shed pollens (in fertile plants) were also collected. Total RNA was extracted using Qiagen RNeasy Plant Mini Kit™ and cDNA was synthesized using Qiagen QuantiTect Reverse Transcription Kit™ (Qiagen, Carlsbad, Calif.). For RT-PCR, the expression of elongation factor α-1 (EF α1) of maize was used as an internal control. Primers for Rf3-PPR2 and EF α1 and dual labeled probes with FAM or VIC dyes and Minor Groove Binding Non Fluorescence Quencher™ I (MGBNFQ) quencher were synthesized by Applied Biosystems (Foster City, Calif.). Taqman® genotyping master mix (Applied Biosystems, Foster City, Calif.) was used to set up 10 µl PCR reactions and the PCR was performed on Roche LightCycler 480™ thermocycler (Roche, Indianapolis, Ind.). The PCR program was initiated with 10 minutes activation of the Taq enzyme at 95° C., followed by 50 cycles of 95° C. for 10 seconds and 58° C. for 38 seconds. Fluorescence signals were recorded at the end of each cycle. Relative expression levels of Rf3-PPR2 to EF α1 was calculated using the Delta Delta CT method.

Seven Taqman® assays were designed based on modifications that resulted in amino acid changes within the Rf3-PPR2 gene (see Table 2). Surprisingly, only the CMS-S9 assay amplified an amplicon that corresponded with the presence of Rf3 or rf3 gene sequence in the fertile restorer lines and cytoplasmic male sterile lines, respectively. This assay was able to identify a single base pair modification (e.g., mutation) that resulted in the rf3 cytoplasmic male sterile phenotype. As such, this single base pair modification could be used to discern between the rf3 cytoplasmic male sterile and the Rf3 restored fertile plants. Despite the numerous amino acid mutation present in the rf3 lines, only plants containing the SEQ ID NO:1 motif resulted in the observation of rf3 cytoplasmic male sterile plants.

The results of the quantitative RT-PCR showed that plants containing the SEQ ID NO:5 motif expressed in Rf3 the restorer parent LH60 and F3 plants that were homozygous or heterozygous for the restorer allele in all tested growing stages. However, Rf3 did not express in CMS-S parents, F3s homozygous for the rf3 allele and the commercial maize lines. Notably, Rf3 expression levels were distinguishable between Rf3 homozygous (Rf3/Rf3) and heterozygous (Rf3/rf3) F3 individuals, which could explain why homozygous (Rf3/Rf3) plants shed 100% starched-filled fertile pollen while heterozygous (Rf3/rf3) plants shed approximately 50% starch-filled fertile pollen. Finally, the Rf3-PPR2 gene, which restores S-type CMS cytoplasm, expressed in both tassel tissue containing immature pollen, and leaf tissue.

While aspects of this invention have been described in certain embodiments, they can be further modified within the spirit and scope of this disclosure. This application is therefore intended to cover any variations, uses, or adaptations of embodiments of the invention using its general principles. Further, this application is intended to cover such departures from the present disclosure as come within known or customary practice in the art to which these embodiments pertains and which fall within the limits of the appended claims.

What is claimed is:

1. A fusion polypeptide comprising an amino acid sequence having at least 97.5% sequence to the amino acid sequence of SEQ ID NO: 3, wherein said fusion polypeptide comprises an amino acid motif comprising the amino acid sequence of SEQ ID NO: 1; and wherein said fusion polypeptide comprises cytoplasmic male sterile activity.

2. The fusion polypeptide of claim 1, wherein said fusion polypeptide is comprised by a cell.

3. The fusion polypeptide of claim 1, wherein said fusion polypeptide is encoded by a synthetic nucleic acid sequence.

4. The fusion polypeptide of claim 3, wherein said synthetic nucleic acid sequence is operably linked to a promoter.

5. The fusion polypeptide of claim 4, wherein said promoter is functional in plants.

6. The fusion polypeptide of claim 5, wherein said promoter is a cytoplasmic male sterile gene promoter.

* * * * *

SEQUENCE LISTING

<160> NUMBER OF SEQ ID NOS: 36

<210> SEQ ID NO 1
<211> LENGTH: 6
<212> TYPE: PRT
<213> ORGANISM: zea mays

<400> SEQUENCE: 1

Ile Val Phe Phe Ser Ser
1               5

<210> SEQ ID NO 2
<211> LENGTH: 15
<212> TYPE: DNA
<213> ORGANISM: zea mays

<400> SEQUENCE: 2
attgttttct tcagt                                                      15

<210> SEQ ID NO 3
<211> LENGTH: 697
<212> TYPE: PRT
<213> ORGANISM: zea mays

<400> SEQUENCE: 3

Met Asp Cys Cys Thr Arg Ala His Arg Pro Glu Leu Ala Leu Ala Phe
1               5                   10                  15

Phe Gly Gln Leu Leu Arg Thr Gly Leu Arg Val Asp Ile Ile Ala
            20                  25                  30

Asn His Leu Leu Lys Gly Phe Cys Glu Ala Lys Arg Thr Asp Glu Ala
        35                  40                  45

Leu Asp Ile Leu Leu His Arg Thr Pro Glu Leu Gly Cys Val Pro Asp
    50                  55                  60

Val Phe Ser Tyr Ser Ile Leu Leu Lys Ser Leu Cys Asp Gln Gly Lys
65                  70                  75                  80

Ser Gly Gln Ala Asp Asp Leu Leu Arg Met Met Ala Glu Gly Gly Ala
                85                  90                  95

Val Cys Ser Pro Asp Val Val Ala Tyr Asn Thr Val Ile Asp Gly Phe
            100                 105                 110

Phe Lys Glu Gly Asp Val Asn Lys Ala Cys Asp Leu Phe Lys Glu Met
        115                 120                 125

Val Gln Arg Gly Ile Pro Pro Asp Phe Val Thr Tyr Ser Ser Val Val
    130                 135                 140

His Ala Leu Cys Lys Ala Arg Ala Met Asp Lys Ala Glu Ala Phe Leu
145                 150                 155                 160

Arg Gln Met Val Asn Lys Gly Val Leu Pro Asn Asn Trp Thr Tyr Asn
                165                 170                 175

Asn Leu Ile Tyr Gly Tyr Ser Ser Thr Gly Gln Trp Lys Glu Ala Val
            180                 185                 190

Arg Val Phe Lys Glu Met Arg Arg His Ser Ile Leu Pro Asp Val Val
        195                 200                 205

Thr Leu Asn Met Leu Met Gly Ser Leu Cys Lys Tyr Gly Lys Ile Lys
    210                 215                 220

Glu Ala Arg Asp Val Phe Asp Thr Met Ala Met Lys Gly Gln Asn Pro
225                 230                 235                 240

Asp Val Phe Ser Tyr Asn Ile Met Leu Asn Gly Tyr Ala Thr Lys Gly
                245                 250                 255

Cys Leu Val Asp Met Thr Asp Leu Phe Asp Leu Met Leu Gly Asp Gly
            260                 265                 270

Ile Ala Pro Val Ile Cys Thr Phe Asn Val Leu Ile Lys Ala Tyr Ala
        275                 280                 285

Asn Cys Gly Met Leu Asp Lys Ala Met Ile Ile Phe Asn Glu Met Arg

```
            290                 295                 300
Asp His Gly Val Lys Pro Tyr Val Val Thr Tyr Thr Val Ile Ala
305                 310                 315                 320

Ala Leu Cys Arg Ile Gly Lys Met Asp Asp Ala Met Glu Lys Phe Asn
                325                 330                 335

Gln Met Ile Asp Gln Gly Val Ala Pro Asp Lys Tyr Ala Phe His Cys
                340                 345                 350

Leu Ile Gln Gly Phe Cys Thr His Gly Ser Leu Leu Lys Ala Lys Glu
                355                 360                 365

Leu Ile Leu Glu Ile Met Asn Asn Gly Met Arg Leu Asp Ile Val Phe
            370                 375                 380

Phe Ser Ser Ile Ile Asn Asn Leu Cys Lys Leu Gly Arg Val Met Glu
385                 390                 395                 400

Ala Gln Asn Ile Phe Asp Leu Thr Val Asn Val Gly Leu His Pro Thr
                405                 410                 415

Ala Val Val Tyr Ser Met Leu Met Asp Gly Tyr Cys Leu Val Gly Lys
                420                 425                 430

Met Glu Lys Ala Leu Arg Val Phe Asp Ala Met Val Ser Ala Gly Ile
            435                 440                 445

Glu Pro Tyr Val Val Tyr Gly Thr Leu Val Asn Gly Tyr Cys Lys
            450                 455             460

Ile Gly Arg Ile Asp Glu Gly Leu Ser Leu Phe Arg Glu Met Leu Gln
465                 470                 475                 480

Lys Gly Ile Lys Pro Ser Thr Ile Leu Tyr Asn Ile Ile Asp Gly
                485                 490                 495

Leu Phe Gln Ala Gly Arg Thr Val Pro Ala Lys Val Lys Phe His Glu
                500                 505                 510

Met Thr Glu Ser Gly Ile Ala Ile Asn Lys Cys Thr Tyr Asn Ile Val
            515                 520                 525

Leu Arg Gly Phe Phe Lys Asn Arg Cys Phe Asp Glu Ala Ile Phe Leu
            530                 535                 540

Phe Lys Glu Leu Arg Ala Met Asn Val Lys Ile Asp Ile Ile Thr Leu
545                 550                 555                 560

Asn Thr Met Ile Ala Gly Met Phe Gln Thr Arg Arg Val Glu Glu Ala
                565                 570                 575

Lys Asp Leu Phe Ala Ser Ile Ser Arg Ser Gly Leu Val Pro Cys Val
                580                 585                 590

Val Thr Tyr Ser Ile Met Ile Thr Asn Leu Ile Lys Glu Gly Leu Val
            595                 600                 605

Glu Glu Ala Glu Asp Met Phe Ser Ser Met Gln Asn Ala Gly Cys Glu
610                 615                 620

Pro Asn Ser Arg Leu Leu Asn His Val Val Arg Glu Leu Leu Lys Lys
625                 630                 635                 640

Asn Glu Ile Val Arg Ala Gly Ala Tyr Leu Ser Lys Ile Asp Glu Arg
                645                 650                 655

Asn Phe Ser Leu Glu His Leu Thr Thr Met Leu Leu Val Asp Leu Phe
                660                 665                 670

Ser Ser Lys Gly Thr Cys Arg Glu His Ile Arg Phe Leu Pro Ala Lys
                675                 680                 685

Tyr His Phe Leu Ala Glu Ala Ser Pro
            690                 695

<210> SEQ ID NO 4
```

```
<211> LENGTH: 2094
<212> TYPE: DNA
<213> ORGANISM: zea mays

<400> SEQUENCE: 4
atggactgct gcacccgcgc gcaccgccca gagctagcgc tggccttctt cggccagctc      60
ctcaggacag gcttgcgcgt cgatatcatc atcgctaacc accttctcaa gggcttttgt     120
gaagcgaagc ggacagacga ggctttggac atccttctcc acagaacgcc tgagttgggc     180
tgtgtgcccg atgttttctc gtacagcata cttctgaaga gcctctgcga ccaaggaaag     240
agtggccagg cagatgattt gctacgcgat gatggctgaag gggagctgt ctgctcgccc     300
gacgtggttg cctacaatac agtaatcgac ggcttcttta aggagggtga cgtaaataaa     360
gcatgtgatc tattcaaaga aatggtacag cggggcattc cacctgattt tgtgacttat     420
agctctgtgg ttcatgccct gtgtaaggca agagcaatgg acaaggcaga ggctttcctt     480
cgacaaatgg tcaataaagg tgttctgcca ataactgga catataataa cttgatatat     540
ggatactcct ccacaggaca gtggaaggag gcagttaggg tatttaaaga aatgagaaga     600
cacagcatct taccagatgt tgttactttg aacatgttga tgggttccct ttgcaagtat     660
ggaaaaatca aggaagctag agatgttttt gacacaatgg caatgaaggg ccaaaatcct     720
gatgttttct cgtacaatat tatgctcaac gggtacgcta ctaaaggatg tctagttgat     780
atgacagatc tcttcgattt gatgctaggt acggtattca cctgtcat ttgtactttt     840
aatgtgctga tcaaggcata tgcaaactgt ggaatgctag ataaggctat gatcatcttc     900
aatgaaatga gagaccatgg agtgaaacct tatgtggtaa cctatacgac agtgattgct     960
gccctctgca gaatcggtaa gatggatgat gctatggaaa aatttaatca gatgattgat    1020
caaggagtag cacctgataa atatgcattc cattgcctga ttcaaggttt ttgtactcat    1080
ggtagtttac tgaaagccaa ggaattgatt ttggaaataa tgaataatgg catgcgtctt    1140
gatattgttt tcttcagttc gataattaac aaccttgca aactgggaag ggtaatggag    1200
gcacaaaata tatttgactt aactgtaaat gttggtctgc atcctactgc tgtggtgtat    1260
agtatgctta tggatgggta ctgtcttgtt ggcaagatgg agaaagcatt aagagtattt    1320
gatgctatgg tgtcagctgg cattgaacca tacgttgtag tgtatggtac acttgttaat    1380
ggctattgta aaattggaag gattgatgaa ggattgagtc ttttcagaga aatgctgcaa    1440
aagggaataa agccttcaac tatttttatac aacatcataa ttgatgggtt atttcaggcc    1500
gggagaacag ttcctgcaaa ggtgaaattc catgaaatga cagaaagtgg tatcgctatc    1560
aacaaatgta catacaacat agttcttcgt ggatttttta aaaatagatg ctttgatgaa    1620
gcaatctttc ttttcaaaga attacgtgca atgaatgtaa agatcgatat cataactctc    1680
ataccatga tagctggaat gtttcaaacc aggagagttg aagaagctaa ggatctgttt    1740
gcttctatct cgagaagtgg gctggtgcct tgtgttgtga cttacagtat aatgatcaca    1800
aatcttataa aagaaggatt ggtggaagag gcagaagata tgttttcatc catgcagaat    1860
gctggctgtg agcccaattc tcgattgctg aatcatgtag tcaggggaatt actaaagaaa    1920
aatgaaatag tcagggctgg agcttacctg tccaagattg acgagaggaa tttctcactt    1980
gaacatttaa ccacaatgtt gctggtcgat ctcttctcaa gcaaaggaac ttgtagggaa    2040
cacataagat ttctccctgc aaagtatcat tttcttgcag aggccagtcc gtga          2094

<210> SEQ ID NO 5
<211> LENGTH: 5
```

-continued

```
<212> TYPE: PRT
<213> ORGANISM: zea mays

<400> SEQUENCE: 5

Ile Val Leu Phe Ser
1               5

<210> SEQ ID NO 6
<211> LENGTH: 15
<212> TYPE: DNA
<213> ORGANISM: zea mays

<400> SEQUENCE: 6
attgttttat tcagt                                                      15

<210> SEQ ID NO 7
<211> LENGTH: 814
<212> TYPE: PRT
<213> ORGANISM: zea mays

<400> SEQUENCE: 7

Met Pro Ser Cys Ala Arg Ile Ser Ser Ala Val Ser Thr Ala Ala Ala
1               5                   10                  15

Ser Ser Ser Ser Pro Pro His Pro Pro Arg Cys Arg Arg Leu Ala
            20                  25                  30

Ala Ala Thr Ala Arg Val Arg Glu Gly Thr Leu Arg Pro Glu Glu Ala
        35                  40                  45

His Asp Leu Leu Asp Glu Leu Gln Arg Arg Gly Thr Pro Val Leu Glu
    50                  55                  60

Arg Asp Leu Asn Gly Phe Leu Ala Ala Phe Ala Arg Ala Pro Ser Ser
65                  70                  75                  80

Ala Ala Cys Arg Ser Gly Pro Ala Leu Ala Val Ala Leu Phe Asn Arg
                85                  90                  95

Ala Ala Ser Arg Ala Gln Gly Pro Arg Val Leu Ser Pro Thr Ser His
            100                 105                 110

Thr Tyr Ala Ile Leu Met Asp Cys Cys Thr Arg Ala His Arg Pro Glu
        115                 120                 125

Leu Ala Leu Ala Phe Phe Gly Gln Leu Leu Arg Thr Gly Leu Arg Val
    130                 135                 140

Asp Ile Ile Ile Ala Asn His Leu Leu Lys Gly Phe Cys Glu Ala Lys
145                 150                 155                 160

Arg Thr Asp Glu Ala Leu Asp Ile Leu Leu His Arg Thr Pro Glu Leu
                165                 170                 175

Gly Cys Val Pro Asp Val Phe Ser Tyr Ser Ile Leu Leu Lys Ser Leu
            180                 185                 190

Cys Asp Gln Gly Lys Ser Gly Gln Ala Asp Asp Leu Leu Arg Met Met
        195                 200                 205

Ser Glu Gly Gly Ala Val Cys Ser Pro Asp Val Ala Tyr Asn Thr
    210                 215                 220

Val Ile Asp Gly Phe Phe Lys Glu Gly Asp Val Asn Lys Ala Cys Asp
225                 230                 235                 240

Leu Phe Lys Glu Met Val Gln Arg Gly Ile Pro Pro Asp Phe Val Thr
                245                 250                 255

Tyr Ser Ser Val Val His Ala Leu Cys Lys Ala Arg Ala Met Asp Lys
            260                 265                 270

Ala Glu Ala Phe Leu Arg Gln Met Val Asn Lys Gly Val Leu Pro Asn
        275                 280                 285
```

```
Asn Trp Thr Tyr Asn Asn Leu Ile Tyr Gly Tyr Ser Ser Thr Gly Gln
    290                 295                 300

Trp Lys Glu Ala Val Arg Val Phe Lys Glu Met Arg Arg His Ser Ile
305                 310                 315                 320

Leu Pro Asp Val Val Thr Phe Asn Met Leu Met Gly Ser Leu Cys Lys
                325                 330                 335

Tyr Gly Lys Ile Lys Glu Ala Arg Asp Val Phe Asp Thr Met Ala Met
                340                 345                 350

Lys Gly Gln Asn Pro Asp Val Phe Ser Tyr Asn Ile Met Leu Asn Gly
                355                 360                 365

Tyr Ala Thr Lys Gly Cys Leu Val Asp Met Thr Asp Leu Phe Asp Leu
    370                 375                 380

Met Leu Gly Asp Gly Ile Ala Pro Val Ile Cys Thr Phe Asn Val Leu
385                 390                 395                 400

Ile Lys Ala Tyr Ala Asn Cys Gly Met Leu Asp Lys Ala Met Ile Ile
                405                 410                 415

Phe Asn Glu Met Arg Asp His Gly Val Lys Pro Tyr Val Leu Thr Tyr
                420                 425                 430

Thr Thr Val Ile Ala Ala Leu Cys Arg Ile Gly Lys Met Asp Asp Ala
                435                 440                 445

Met Glu Lys Phe Asn Gln Met Ile Asp Gln Gly Val Ala Pro Asp Lys
450                 455                 460

Tyr Ala Tyr His Cys Leu Ile Gln Gly Phe Cys Thr His Gly Ser Leu
465                 470                 475                 480

Leu Lys Ala Lys Glu Leu Ile Ser Glu Ile Met Asn Asn Gly Met His
                485                 490                 495

Leu Asp Ile Val Leu Phe Ser Ser Ile Ile Asn Asn Leu Cys Lys Leu
                500                 505                 510

Gly Arg Val Met Asp Ala Gln Asn Ile Phe Asp Leu Thr Val Asn Val
                515                 520                 525

Gly Leu His Pro Thr Ala Val Val Tyr Ser Met Leu Met Asp Gly Tyr
                530                 535                 540

Cys Leu Val Gly Lys Met Glu Asn Ala Leu Arg Val Phe Asp Ala Met
545                 550                 555                 560

Val Ser Ala Gly Ile Glu Pro Tyr Asp Val Val Tyr Gly Thr Leu Val
                565                 570                 575

Asn Gly Tyr Cys Lys Ile Gly Arg Ile Asp Glu Gly Leu Ser Leu Phe
                580                 585                 590

Arg Glu Met Leu Gln Asn Gly Ile Lys Pro Ser Thr Ile Leu Tyr Asn
                595                 600                 605

Ile Ile Ile Asp Gly Leu Phe Glu Ala Gly Arg Thr Val Pro Ala Lys
                610                 615                 620

Val Lys Phe His Glu Met Thr Glu Ser Gly Ile Ala Met Tyr Ile Cys
625                 630                 635                 640

Thr Tyr Ile Ile Val Leu Arg Gly Leu Phe Lys Asn Arg Cys Phe Asp
                645                 650                 655

Glu Ala Ile Phe Leu Phe Lys Glu Leu Arg Ala Met Asn Val Lys Ile
                660                 665                 670

Asp Ile Ile Thr Leu Asn Thr Met Ile Ala Gly Met Phe Gln Thr Arg
                675                 680                 685

Arg Val Glu Glu Ala Lys Asp Leu Phe Ala Ser Ile Ser Arg Ser Gly
    690                 695                 700
```

-continued

| | | | | | | | | | | | | |
|---|---|---|---|---|---|---|---|---|---|---|---|---|
|Leu|Val|Pro|Cys|Val|Val|Thr|Tyr|Ser|Ile|Met|Ile|Thr|Asn|Leu|Ile|
|705| | | |710| | | |715| | | |720|

Lys Glu Gly Leu Val Glu Glu Ala Glu Asp Met Phe Ser Ser Met Gln
            725                 730                 735

Asn Ala Gly Cys Glu Pro Tyr Ser Arg Leu Leu Asn His Val Val Arg
        740                 745                 750

Glu Leu Leu Lys Lys Asn Glu Ile Val Arg Ala Gly Ala Tyr Leu Ser
    755                 760                 765

Lys Ile Asp Glu Arg Asn Phe Ser Leu Glu Tyr Leu Thr Thr Met Leu
770                 775                 780

Leu Val Asp Leu Phe Ser Ser Lys Gly Thr Cys Arg Glu His Ile Arg
785                 790                 795                 800

Phe Leu Pro Ala Lys Tyr His Phe Leu Ala Glu Ala Ser Pro
            805                 810

<210> SEQ ID NO 8
<211> LENGTH: 2445
<212> TYPE: DNA
<213> ORGANISM: zea mays

<400> SEQUENCE: 8

```
atgccgtcat gtgcccgcat ctcctccgcc gtctccaccg ccgccgcatc ctcctcctcg    60
ccgccgccgc atcctcctcg ctgccgccgc ctcgccgccg ccacggcgcg cgtgcgggag   120
gggacgctcc gccctgagga agcacacgac ctgctcgacg agttgcagcg tcgaggcacg   180
cccgttctcg agcgcgatct gaacggcttc ctcgcggcgt tcgcgcgtgc gccgtcctcc   240
gccgcctgca ggagtggccc tgccctcgcc gtcgcgctct caaccgcgc ggcgtctcgg    300 gctcaaggac cgcgggtgct gtcccccaca tcccacacct acgccatcct catggactgc   360
tgcacccgcg cgcaccgccc agagctagcg ctggcgttct tcggccagct cctcaggaca   420
ggcttgcgcg tcgatatcat catcgctaac caccttctca agggcttttg tgaagcgaag   480
cggacagacg aggctttgga catccttctc cacagaacgc ctgagttggg ctgtgtgccc   540
gatgttttct cgtacagcat acttctgaag agcctctgcg accaaggaaa gagtggccag   600
gcagatgatt tgctacggat gatgtctgaa ggggagctg tctgctcgcc cgacgtggtt   660
gcctacaata cagtaatcga cggcttcttt aaggagggtg acgtaaataa agcatgtgat   720
ctattcaaag aaatggtaca gcggggcatt ccacctgatt tgtgacttta agctctgtg   780 gttcatgccc tgtgtaaggc aagagcaatg acaaggcag aggctttcct tcgacaaatg   840
gtcaataaag gtgttctgcc aaataactgg acatataata acttgatata tggatactcc   900
tccacaggac agtggaagga ggcagttagg gtatttaaag aaatgagaag acatagcatc   960
ttaccagatg ttgttacttt taacatgttg atgggttccc tttgcaagta tggaaaaatc  1020
aaggaagcta gagatgtttt tgacacaatg gcaatgaagg gccaaaatcc tgatgttttc  1080
tcgtacaata ttatgctcaa cgggtacgct actaaaggat gtctagttga tatgacagat  1140
ctcttcgatt tgatgctagg tgacggtatt gcacctgtca tttgtacttt taatgtgctg  1200
atcaaggcat atgcaaactg tggaatgcta gataaggcta tgatcatctt caatgaaatg  1260
agagaccatg gagtgaaacc ttatgtgtta acctatacga cagtgattgc tgccctctgc  1320
agaatcggta gatggatga tgctatggaa aaatttaatc agatgattga tcaaggagta  1380
gcacctgata aatatgcata ccattgcctg attcaaggtt tttgtactca tggtagttta  1440
ctgaaagcca aggaattgat ttcggaaata atgaataatg gcatgcatct tgacattgtt  1500
```

```
ttattcagtt cgataattaa caacctttgc aaattgggaa gggtaatgga tgcacaaaat   1560
atatttgact taactgtaaa tgttggtctg catcctactg ctgtggtgta tagtatgctg   1620
atggatgggt actgtcttgt tggcaagatg gagaatgcat taagagtatt tgatgctatg   1680
gtgtcagctg gcattgaacc atacgatgta gtgtatggta cacttgttaa tggctattgt   1740
aaaattggaa ggattgatga aggattgagt cttttcagag aaatgctgca aaatggaata   1800
aagccttcaa ctattttata caacatcata attgatgggt tatttgaggc gggagaaca    1860
gttcctgcaa aggtgaaatt ccatgaaatg acagaaagtg tatcgctat gtacatatgt    1920
acatacatca tagttcttcg tggactttt aaaaatagat ctttgatga agcaatcttt     1980
cttttcaaag aattacgtgc aatgaatgta aagatcgata tcataactct caataccatg   2040
atagctggaa tgtttcaaac caggagagtt gaagaagcta aggatctgtt tgcttctatc   2100
tcgagaagtg ggctggtgcc ttgtgttgtg acttacagta taatgatcac aaatcttata   2160
aaagaaggat tggtggaaga ggcagaagat atgttttcat ccatgcagaa tgctggctgt   2220
gagccctatt ctcgattgtt gaatcatgta gtcaggaat tactaaagaa aaatgaaata    2280
gtcagggctg gagcttacct gtccaagatt gacgagagga atttctcact tgaatattta   2340
accacaatgt tgctggtcga tctcttctca agcaaaggaa cttgtaggga acacataaga   2400
tttctccctg caaagtatca ttttcttgca gaggccagtc cgtga                   2445
```

```
<210> SEQ ID NO 9
<211> LENGTH: 814
<212> TYPE: PRT
<213> ORGANISM: zea mays

<400> SEQUENCE: 9
```

```
Met Pro Ser Cys Ala Arg Ile Ser Ser Ala Val Ser Thr Ala Ala Ala
1               5                   10                  15

Ser Ser Ser Ser Pro Pro Pro His Pro Pro Arg Cys Arg Arg Leu Ala
                20                  25                  30

Ala Ala Thr Ala Arg Val Arg Glu Gly Thr Leu Arg Pro Glu Glu Ala
            35                  40                  45

His Asp Leu Leu Asp Glu Leu Gln Arg Arg Gly Thr Pro Val Leu Glu
    50                  55                  60

Arg Asp Leu Asn Gly Phe Leu Ala Ala Ile Ala Arg Ala Pro Ser Ser
65                  70                  75                  80

Ala Ala Cys Arg Ser Gly Pro Ala Leu Ala Val Ala Leu Phe Asn Arg
                85                  90                  95

Ala Ala Ser Arg Ala Gln Gly Pro Arg Val Leu Ser Pro Thr Ser His
            100                 105                 110

Thr Tyr Ala Ile Leu Met Asp Cys Cys Thr Arg Ala His Arg Pro Glu
    115                 120                 125

Leu Ala Leu Ala Phe Phe Gly Gln Leu Leu Arg Thr Gly Leu Arg Val
130                 135                 140

Asp Ile Ile Ile Ala Asn His Leu Leu Lys Gly Phe Cys Glu Ala Lys
145                 150                 155                 160

Arg Thr Asp Glu Ala Leu Asp Ile Leu Leu His Arg Thr Pro Glu Leu
                165                 170                 175

Gly Cys Val Pro Asp Val Phe Ser Tyr Ser Ile Leu Leu Lys Ser Leu
            180                 185                 190

Cys Asp Gln Gly Lys Ser Gly Gln Ala Asp Asp Leu Leu Arg Met Met
    195                 200                 205
```

```
Ala Glu Gly Gly Ala Val Cys Ser Pro Asp Val Val Ala Tyr Thr Thr
210                 215                 220

Val Ile Asp Cys Phe Phe Lys Glu Gly Asp Val Asn Lys Ala Cys Asp
225                 230                 235                 240

Leu Phe Lys Glu Met Val Gln Arg Gly Ile Pro Pro Asp Phe Val Thr
                245                 250                 255

Tyr Ser Ser Val Val His Ala Leu Cys Lys Ala Arg Ala Met Asp Lys
            260                 265                 270

Ala Glu Ala Phe Leu Arg Gln Met Val Asn Lys Gly Val Leu Pro Asn
        275                 280                 285

Asn Trp Thr Tyr Asn Asn Leu Ile Tyr Gly Tyr Ser Ser Thr Gly Gln
290                 295                 300

Trp Lys Glu Ala Val Arg Val Phe Lys Glu Met Arg Arg His Ser Ile
305                 310                 315                 320

Leu Pro Asp Val Val Thr Leu Asn Met Leu Met Gly Ser Leu Cys Lys
                325                 330                 335

Tyr Gly Lys Ile Lys Glu Ala Arg Asp Val Phe Asp Thr Met Ala Met
            340                 345                 350

Lys Gly Gln Asn Pro Asn Val Phe Ser Tyr Asn Ile Met Leu Asn Gly
        355                 360                 365

Tyr Ala Thr Lys Gly Cys Leu Val Asp Met Thr Asp Leu Phe Asp Leu
370                 375                 380

Met Leu Gly Asp Gly Ile Ala Pro Val Ile Cys Thr Phe Asn Val Leu
385                 390                 395                 400

Ile Lys Ala Tyr Ala Asn Cys Gly Met Leu Asp Lys Ala Met Ile Ile
                405                 410                 415

Phe Asn Glu Met Arg Asp His Gly Val Lys Pro Tyr Val Val Thr Tyr
            420                 425                 430

Thr Thr Val Ile Ala Ala Leu Cys Arg Ile Gly Lys Met Asp Asp Ala
        435                 440                 445

Met Glu Lys Phe Asn Gln Met Ile Asp Gln Gly Val Ala Pro Asp Lys
450                 455                 460

Tyr Ala Phe His Cys Leu Ile Gln Gly Phe Cys Thr His Gly Ser Leu
465                 470                 475                 480

Leu Lys Ala Lys Glu Leu Ile Leu Glu Ile Met Asn Asn Gly Met Arg
                485                 490                 495

Leu Asp Ile Val Phe Phe Ser Ser Ile Ile Asn Asn Leu Cys Lys Leu
            500                 505                 510

Gly Arg Val Met Glu Ala Gln Asn Ile Phe Asp Leu Thr Val Asn Val
        515                 520                 525

Gly Leu His Pro Thr Ala Val Val Tyr Ser Met Leu Met Asp Gly Tyr
530                 535                 540

Cys Leu Val Gly Lys Met Glu Lys Ala Leu Arg Val Phe Asp Ala Met
545                 550                 555                 560

Val Ser Ala Gly Ile Glu Pro Asp Val Val Tyr Gly Thr Leu Val
                565                 570                 575

Asn Gly Tyr Cys Lys Ile Gly Arg Ile Asp Glu Gly Leu Ser Leu Phe
            580                 585                 590

Arg Glu Met Leu Gln Lys Gly Ile Lys Pro Ser Thr Ile Leu Tyr Asn
        595                 600                 605

Ile Ile Ile Asp Gly Leu Phe Gln Ala Gly Arg Thr Val Pro Ala Lys
610                 615                 620

Val Lys Phe His Glu Met Thr Glu Ser Gly Ile Ala Met Asn Lys Cys
```

Thr Tyr Asn Ile Val Leu Arg Gly Leu Phe Lys Asn Arg Cys Phe Asp
625                 630                 635                 640
                        645                       650                       655

Glu Ala Ile Phe Leu Phe Lys Glu Leu Arg Ala Met Asn Val Lys Ile
            660                       665                       670

Asp Ile Ile Thr Leu Asn Thr Met Ile Ala Gly Met Phe Gln Thr Arg
                675                       680                       685

Arg Val Glu Glu Ala Lys Asp Leu Phe Ala Ser Ile Ser Arg Ser Gly
            690                       695                       700

Leu Val Pro Cys Val Val Thr Tyr Ser Ile Met Ile Thr Asn Leu Ile
705                 710                       715                       720

Lys Glu Gly Leu Val Glu Ala Glu Asp Met Phe Ser Ser Met Gln
                        725                       730                       735

Asn Ala Gly Cys Glu Pro Asp Ser Arg Leu Leu Asn His Val Val Arg
                740                       745                       750

Glu Leu Leu Lys Lys Asn Glu Ile Val Arg Ala Gly Ala Tyr Leu Ser
                    755                       760                       765

Lys Ile Asp Glu Arg Asn Phe Ser Leu Glu His Leu Thr Thr Met Leu
        770                       775                       780

Leu Val Asp Leu Phe Ser Ser Lys Gly Thr Cys Arg Glu His Ile Arg
785                 790                       795                       800

Phe Leu Pro Ala Lys Tyr His Phe Leu Ala Glu Ala Ser Pro
                    805                       810

<210> SEQ ID NO 10
<211> LENGTH: 2445
<212> TYPE: DNA
<213> ORGANISM: zea mays

<400> SEQUENCE: 10
atgccgtcat gtgcccgcat ctcctccgcc gtctccaccg ccgccgcatc ctcctcctcg    60
ccgccgccgc atcctcctcg ctgccgccgc ctcgccgccg ccacggcgcg cgtgcgggag   120
gggacgctcc gccctgagga agcacacgac ctgctcgacg agttgcagcg tcgaggcacg   180
cccgttctcg agcgcgatct gaacggcttc ctcgcggcga tcgcgcgtgc gccgtcctcc   240
gccgcctgca ggagtggccc tgccctcgcc gtcgcgctct tcaaccgcgc ggcgtctcgg   300
gctcaaggac cgcgggtgct gtcccccaca tcccacacct acgccatcct catggactgc   360
tgcacccgcg cgcaccgccc agagctagcg ctggcgttct tcggccagct cctcaggaca   420
ggcttgcgcg tcgatatcat catcgctaac caccttctca agggcttttg tgaagcgaag   480
cggacagacg aggctttgga catccttctc cacagaacgc ctgagttggg ctgtgtgccc   540
gatgttttct cgtacagcat acttctgaag agcctctgtg accaaggaaa gagtggccag   600
gcagatgatt tgttacggat gatggctgaa gggggagctg tctgctcgcc cgacgtggtt   660
gcctacacta cagtaatcga ctgcttcttt aaggagggtg acgtaaataa agcatgtgat   720
ctattcaaag aaatggtaca gcgggcatt ccacctgatt tgtgacttga agctctgtg     780 gttcatgccc tgtgtaaggc aagagcaatg gacaaggcag aggctttcct tcgacaaatg   840
gtcaataaag gtgttctgcc aaataactgg acatataata acttgatata tggatactcc   900
tccacaggac agtggaagga ggcagttagg gtatttaaag aaatgagaag acacagcatc   960
ttaccagatg ttgttacttt gaacatgttg atgggttccc tttgcaagta tggaaaaatc  1020
aaggaagcta gagatgtttt tgacacaatg gcaatgaagg gccaaaatcc taatgttttc  1080

```
tcctacaata ttatgctcaa cgggtacgct actaaaggat gtctagttga tatgacagat    1140
ctcttcgatt tgatgctagg tgacggtatt gcacctgtca tttgtacttt taatgtgctg    1200
atcaaggcat atgcaaactg tggaatgcta gataaggcta tgatcatctt caatgaaatg    1260
agagaccatg gagtgaaacc ttatgtggta acctatacga cagtgattgc tgccctctgc    1320
agaatcggta agatggatga tgctatggaa aaatttaatc agatgattga tcaaggagta    1380
gcacctgata aatatgcatt ccattgcctg attcaaggtt tttgtactca tggtagttta    1440
ctgaaagcca aggaattgat tttggaaata atgaataatg gcatgcgtct tgatattgtt    1500
ttcttcagtt cgataattaa caacctttgc aaactgggaa gggtaatgga ggcacaaaat    1560
atatttgact taactgtaaa tgttggtctg catcctactg ctgtggtgta tagtatgctt    1620
atggatgggt actgtcttgt tggcaagatg gagaaagcat taagagtatt tgatgctatg    1680
gtgtcagctg gcattgaacc agacgatgta gtgtatggta cacttgttaa tggctattgt    1740
aaaattggaa ggattgatga aggattgagt cttttcagag aaatgctgca aaagggaata    1800
aagccttcaa ctattttata caacatcata attgatgggt tatttcaggc cgggagaaca    1860
gttcctgcaa aggtgaaatt ccatgaaatg acagaaagtg gtatcgctat gaacaaatgt    1920
acatacaaca tagttcttcg tggacttttt aaaaatagat gctttgatga agcaatcttt    1980
cttttcaaag aattacgtgc aatgaatgta aagatcgata tcataactct caataccatg    2040
atagctggaa tgtttcaaac caggagagtt gaagaagcta aggatctgtt tgcttctatc    2100
tcgagaagtg ggctggtgcc ttgtgttgtg acttacagta taatgatcac aaatcttata    2160
aaagaaggat tggtggaaga ggcagaagat atgtttttcat ccatgcagaa tgctggctgt    2220
gagcccgatt ctcgattgct gaatcatgta gtcagggaat tactaaagaa aaatgaaata    2280
gtcagggctg gagcttacct gtccaagatt gacgagagga atttctcact tgaacattta    2340
accacaatgt tgctggtcga tctcttctca agcaaaggaa cttgtaggga acacataaga    2400
tttctccctg caaagtatca ttttcttgca gaggccagtc cgtga                   2445
```

<210> SEQ ID NO 11
<211> LENGTH: 615
<212> TYPE: PRT
<213> ORGANISM: zea mays

<400> SEQUENCE: 11

```
Met Pro Ser Cys Ala Arg Ile Ser Ser Ala Val Ser Thr Ala Ala
1               5                   10                  15

Ser Ser Ser Ser Pro Pro His Pro Pro Arg Cys Arg Arg Leu Ala
                20                  25                  30

Ala Ala Thr Ala Arg Val Arg Glu Gly Thr Leu Arg Pro Glu Glu Ala
            35                  40                  45

His Asp Leu Leu Asp Glu Leu Gln Arg Arg Gly Thr Pro Val Leu Glu
    50                  55                  60

Arg Asp Leu Asn Gly Phe Leu Ala Ala Ile Ala Arg Ala Pro Ser Ser
65                  70                  75                  80

Ala Ala Cys Arg Ser Gly Pro Ala Leu Ala Val Ala Leu Phe Asn Arg
                85                  90                  95

Ala Ala Ser Arg Ala Gln Gly Pro Arg Val Leu Ser Pro Thr Ser His
                100                 105                 110

Thr Tyr Ala Ile Leu Met Asp Cys Cys Thr Arg Ala His Arg Pro Glu
            115                 120                 125

Leu Ala Leu Ala Phe Phe Gly Gln Leu Leu Arg Thr Gly Leu Arg Val
```

```
              130                 135                 140
Asp Ile Ile Ile Ala Asn His Leu Leu Lys Gly Phe Cys Glu Ala Lys
145                 150                 155                 160

Arg Thr Asp Glu Ala Leu Asp Ile Leu Leu His Arg Thr Pro Glu Leu
                165                 170                 175

Gly Cys Val Pro Asp Val Phe Ser Tyr Ser Ile Leu Leu Lys Ser Leu
                180                 185                 190

Cys Asp Gln Gly Lys Ser Gly Gln Ala Asp Asp Leu Leu Arg Met Met
            195                 200                 205

Ser Glu Gly Gly Ala Val Cys Ser Pro Asp Val Val Ala Tyr Asn Thr
210                 215                 220

Val Ile Asp Gly Phe Phe Lys Glu Gly Asp Val Asn Lys Ala Cys Asp
225                 230                 235                 240

Leu Phe Lys Glu Met Val Gln Arg Gly Ile Pro Pro Asp Phe Val Thr
                245                 250                 255

Tyr Ser Ser Val Val His Ala Leu Cys Lys Ala Arg Ala Met Asp Lys
                260                 265                 270

Ala Glu Ala Phe Leu Arg Gln Met Val Asn Lys Gly Val Leu Pro Asn
            275                 280                 285

Asn Trp Thr Tyr Asn Asn Leu Ile Tyr Gly Tyr Ser Ser Thr Gly Gln
290                 295                 300

Trp Lys Glu Ala Val Arg Val Phe Lys Glu Met Arg Arg His Ser Ile
305                 310                 315                 320

Leu Pro Asp Val Val Thr Phe Asn Met Leu Met Gly Ser Leu Cys Lys
                325                 330                 335

Tyr Gly Lys Ile Lys Glu Ala Arg Asp Val Phe Asp Thr Met Ala Met
                340                 345                 350

Lys Gly Gln Asn Pro Asp Val Phe Ser Tyr Asn Ile Met Leu Asn Gly
            355                 360                 365

Tyr Ala Thr Lys Gly Cys Leu Val Asp Met Thr Asp Leu Phe Asp Leu
370                 375                 380

Met Leu Gly Asp Gly Ile Ala Pro Val Ile Cys Thr Phe Asn Val Leu
385                 390                 395                 400

Ile Lys Ala Tyr Ala Asn Cys Gly Met Leu Asp Lys Ala Met Ile Ile
                405                 410                 415

Phe Asn Glu Met Arg Asp His Gly Val Lys Pro Tyr Val Leu Thr Tyr
                420                 425                 430

Thr Thr Val Ile Ala Ala Leu Cys Arg Ile Gly Lys Met Asp Asp Ala
            435                 440                 445

Met Glu Lys Phe Asn Gln Met Ile Asp Gln Gly Val Ala Pro Asp Lys
450                 455                 460

Tyr Ala Tyr His Cys Leu Ile Gln Gly Phe Cys Thr His Gly Ser Leu
465                 470                 475                 480

Leu Lys Ala Lys Glu Leu Ile Ser Glu Ile Met Asn Asn Gly Met His
                485                 490                 495

Leu Asp Ile Val Leu Phe Ser Ser Ile Ile Asn Asn Leu Cys Lys Leu
                500                 505                 510

Gly Arg Val Met Asp Ala Gln Asn Ile Phe Asp Leu Thr Val Asn Val
            515                 520                 525

Gly Leu His Pro Thr Ala Val Val Tyr Ser Met Leu Met Asp Gly Tyr
530                 535                 540

Cys Leu Val Gly Lys Met Glu Asn Ala Leu Arg Val Phe Asp Ala Met
545                 550                 555                 560
```

| | | |
|---|---|---|
| Val Ser Ala Gly Ile Glu Pro Tyr Asp Val Val Tyr Gly Thr Leu Val | | |
| 565 570 575 | | |

Asn Gly Tyr Cys Lys Ile Gly Arg Ile Asp Glu Gly Leu Ser Leu Phe
            580                 585                 590

Arg Glu Met Leu Gln Lys Gly Ile Lys Pro Ser Thr Ile Leu Tyr Asn
        595                 600                 605

Ile Ile Ile Asp Gly Leu Phe
    610             615

<210> SEQ ID NO 12
<211> LENGTH: 1848
<212> TYPE: DNA
<213> ORGANISM: zea mays

<400> SEQUENCE: 12

```
atgccgtcat gtgcccgcat ctcctccgcc gtctccaccg ccgccgcatc ctcctcctcg      60
ccgccgccgc atcctcctcg ctgccgccgc ctcgccgccg ccacggcgcg cgtgcgggag     120
gggacgctcc gccctgagga agcacacgac ctgctcgacg agttgcagcg tcgaggcacg     180
cccgttctcg agcgcgatct gaacggcttc ctcgcggcga tcgcgcgtgc gccgtcctcc     240
gccgcctgca ggagtggccc tgccctcgcc gtcgcgctct caaccgcgc ggcgtctcgg      300
gctcaaggac cgcgggtgct gtcccccaca tcccacacct acgccatcct catggactgc     360
tgcacccgcg cgcaccgccc agagctagcg ctggcgttct tcggccagct cctcaggaca     420
ggcttgcgcg tcgatatcat catcgctaac caccttctca agggcttttg tgaagcgaag     480
cggacagacg aggctttgga catccttctc cacagaacgc ctgagttggg ctgtgtgccc     540
gatgttttct cgtacagcat acttctgaag agcctctgcg accaaggaaa gagtggccag     600
gcagatgatt tgctacggat gatgtctgaa ggggagctg tctgctcgcc cgacgtggtt      660
gcctacaata cagtaatcga cggcttcttt aaggagggtg acgtaaataa agcatgtgat     720
ctattcaaag aaatggtaca gcggggcatt ccacctgatt ttgtgactta tagctctgtg     780
gttcatgccc tgtgtaaggc aagagcaatg acaaggcag aggcttttcct tcgacaaatg     840
gtcaataaag gtgttctgcc aaataactgg acatataata acttgatata tggatactcc     900
tccacaggac agtggaagga ggcagttagg gtatttaaag aaatgagaag acatagcatc     960
ttaccagatg ttgttacttt taacatgttg atgggttccc tttgcaagta tggaaaaatc    1020
aaggaagcta gagatgtttt tgacacaatg gcaatgaagg gccaaaatcc tgatgttttc    1080
tcgtacaata ttatgctcaa cgggtacgct actaaaggat gtctagttga tatgacagat    1140
ctcttcgatt tgatgctagg tgacggtatt gcacctgtca tttgtacttt taatgtgctg    1200
atcaaggcat atgcaaactg tggaatgcta gataaggcta tgatcatctt caatgaaatg    1260
agagaccatg gagtgaaacc ttatgtgcta acctatcga cagtgattgc tgccctctgc    1320
agaatcggta gatggatga tgctatggaa aaatttaatc agatgattga tcaaggagta    1380
gcacctgata aatatgcata ccattgcctg attcaaggtt tttgtactca tggtagttta    1440
ctgaaagcca aggaattgat ttcggaaata atgaataatg gcatgcatct tgacattgtt    1500
ttattcagtt cgataattaa caacctttgc aaattgggaa gggtaatgga tgcacaaaat    1560
atatttgact taactgtaaa tgttggtctg catcctactg ctgtggtgta gtatgctg      1620
atggatgggt actgtcttgt tggcaagatg gagaatgcat taagagtatt tgatgctatg    1680
gtgtcagctg gcattgaacc atacgatgta gtgtatggta cacttgttaa tggctattgt    1740
```

-continued

```
aaaattggaa ggattgatga aggattgagt cttttcagag aaatgctgca aaagggaata      1800
aagccttcaa ctattttata caacatcata attgatgggt tattttag                  1848

<210> SEQ ID NO 13
<211> LENGTH: 24
<212> TYPE: DNA
<213> ORGANISM: artificial sequence
<220> FEATURE:
<223> OTHER INFORMATION: primer sequence

<400> SEQUENCE: 13
gattgatcaa ggagtagcac ctga                                            24

<210> SEQ ID NO 14
<211> LENGTH: 27
<212> TYPE: DNA
<213> ORGANISM: artificial sequence
<220> FEATURE:
<223> OTHER INFORMATION: primer sequence

<400> SEQUENCE: 14
cttggctttc agtaaactac catgagt                                         27

<210> SEQ ID NO 15
<211> LENGTH: 18
<212> TYPE: DNA
<213> ORGANISM: artificial sequence
<220> FEATURE:
<223> OTHER INFORMATION: primer sequence

<400> SEQUENCE: 15
cataccattg cctgattc                                                   18

<210> SEQ ID NO 16
<211> LENGTH: 26
<212> TYPE: DNA
<213> ORGANISM: artificial sequence
<220> FEATURE:
<223> OTHER INFORMATION: primer sequence

<400> SEQUENCE: 16
ggtagtttac tgaaagccaa ggaatt                                          26

<210> SEQ ID NO 17
<211> LENGTH: 26
<212> TYPE: DNA
<213> ORGANISM: artificial sequence
<220> FEATURE:
<223> OTHER INFORMATION: primer sequence

<400> SEQUENCE: 17
ttgcaaaggt tgttaattat cgaact                                          26

<210> SEQ ID NO 18
<211> LENGTH: 19
<212> TYPE: DNA
<213> ORGANISM: artificial sequence
<220> FEATURE:
<223> OTHER INFORMATION: primer sequence

<400> SEQUENCE: 18
atggcatgca tcttgacat                                                  19

<210> SEQ ID NO 19
<211> LENGTH: 23
```

<212> TYPE: DNA
<213> ORGANISM: artificial sequence
<220> FEATURE:
<223> OTHER INFORMATION: primer sequence

<400> SEQUENCE: 19
gggtactgtc ttgttggcaa gat                                              23

<210> SEQ ID NO 20
<211> LENGTH: 20
<212> TYPE: DNA
<213> ORGANISM: artificial sequence
<220> FEATURE:
<223> OTHER INFORMATION: primer sequence

<400> SEQUENCE: 20
tggttcaatg ccagctgaca                                                  20

<210> SEQ ID NO 21
<211> LENGTH: 25
<212> TYPE: DNA
<213> ORGANISM: artificial sequence
<220> FEATURE:
<223> OTHER INFORMATION: primer sequence

<400> SEQUENCE: 21
agaatgcatt aagagtattt gatgc                                            25

<210> SEQ ID NO 22
<211> LENGTH: 22
<212> TYPE: DNA
<213> ORGANISM: artificial sequence
<220> FEATURE:
<223> OTHER INFORMATION: primer sequence

<400> SEQUENCE: 22
ggacagtgga aggaggcagt ta                                               22

<210> SEQ ID NO 23
<211> LENGTH: 21
<212> TYPE: DNA
<213> ORGANISM: artificial sequence
<220> FEATURE:
<223> OTHER INFORMATION: primer sequence

<400> SEQUENCE: 23
ccatacttgc aaagggaacc c                                                21

<210> SEQ ID NO 24
<211> LENGTH: 24
<212> TYPE: DNA
<213> ORGANISM: artificial sequence
<220> FEATURE:
<223> OTHER INFORMATION: primer sequence

<400> SEQUENCE: 24
ccagatgttg ttacttttaa catg                                             24

<210> SEQ ID NO 25
<211> LENGTH: 25
<212> TYPE: DNA
<213> ORGANISM: artificial sequence
<220> FEATURE:
<223> OTHER INFORMATION: primer sequence

<400> SEQUENCE: 25
gaataatggc atgcgtcttg atatt                                          25

<210> SEQ ID NO 26
<211> LENGTH: 26
<212> TYPE: DNA
<213> ORGANISM: artificial sequence
<220> FEATURE:
<223> OTHER INFORMATION: primer sequence

<400> SEQUENCE: 26
gtaggatgca gaccaacatt tacagt                                         26

<210> SEQ ID NO 27
<211> LENGTH: 18
<212> TYPE: DNA
<213> ORGANISM: artificial sequence
<220> FEATURE:
<223> OTHER INFORMATION: primer sequence

<400> SEQUENCE: 27
cctttgcaaa ttgggaag                                                  18

<210> SEQ ID NO 28
<211> LENGTH: 27
<212> TYPE: DNA
<213> ORGANISM: artificial sequence
<220> FEATURE:
<223> OTHER INFORMATION: primer sequence

<400> SEQUENCE: 28
gtactcatgg tagtttactg aaagcca                                        27

<210> SEQ ID NO 29
<211> LENGTH: 21
<212> TYPE: DNA
<213> ORGANISM: artificial sequence
<220> FEATURE:
<223> OTHER INFORMATION: primer sequence

<400> SEQUENCE: 29
gcatccatta cccttcccaa t                                              21

<210> SEQ ID NO 30
<211> LENGTH: 26
<212> TYPE: DNA
<213> ORGANISM: artificial sequence
<220> FEATURE:
<223> OTHER INFORMATION: primer sequence

<400> SEQUENCE: 30
atcttgacat tgttttattc agttcg                                         26

<210> SEQ ID NO 31
<211> LENGTH: 22
<212> TYPE: DNA
<213> ORGANISM: artificial sequence
<220> FEATURE:
<223> OTHER INFORMATION: primer sequence

<400> SEQUENCE: 31
gttcctgcaa aggtgaaatt cc                                             22

<210> SEQ ID NO 32
<211> LENGTH: 24
<212> TYPE: DNA
<213> ORGANISM: artificial sequence -continued

```
<220> FEATURE:
<223> OTHER INFORMATION: primer sequence

<400> SEQUENCE: 32
gaaagattgc ttcatcaaag catc                                          24

<210> SEQ ID NO 33
<211> LENGTH: 20
<212> TYPE: DNA
<213> ORGANISM: artificial sequence
<220> FEATURE:
<223> OTHER INFORMATION: primer sequence

<400> SEQUENCE: 33
ggtatcgcta tgtacatatg                                               20

<210> SEQ ID NO 34
<211> LENGTH: 23
<212> TYPE: DNA
<213> ORGANISM: artificial sequence
<220> FEATURE:
<223> OTHER INFORMATION: primer sequence

<400> SEQUENCE: 34
ataacgtgcc ttggagtatt tgg                                           23

<210> SEQ ID NO 35
<211> LENGTH: 22
<212> TYPE: DNA
<213> ORGANISM: artificial sequence
<220> FEATURE:
<223> OTHER INFORMATION: primer sequence

<400> SEQUENCE: 35
tggagtgaag cagatgattt gc                                            22

<210> SEQ ID NO 36
<211> LENGTH: 18
<212> TYPE: DNA
<213> ORGANISM: artificial sequence
<220> FEATURE:
<223> OTHER INFORMATION: primer sequence

<400> SEQUENCE: 36
ttgcatccat cttgttgc                                                 18
```